(12) United States Patent
Croce et al.

(10) Patent No.: US 9,249,468 B2
(45) Date of Patent: Feb. 2, 2016

(54) METHODS AND MATERIALS RELATED TO OVARIAN CANCER

(71) Applicant: The Ohio State University, Columbus, OH (US)

(72) Inventors: Carlo M. Croce, Columbus, OH (US); Andrea Vecchione, Rome (IT)

(73) Assignee: The Ohio State University, Columbus, OH (US)

( * ) Notice: Subject to any disclaimer, the term of this patent is extended or adjusted under 35 U.S.C. 154(b) by 147 days.

(21) Appl. No.: 13/651,679

(22) Filed: Oct. 15, 2012

(65) Prior Publication Data

US 2013/0096022 A1    Apr. 18, 2013

Related U.S. Application Data

(60) Provisional application No. 61/675,449, filed on Jul. 25, 2012, provisional application No. 61/547,109, filed on Oct. 14, 2011.

(51) Int. Cl.
| | | |
|---|---|---|
| *C12Q 1/68* | (2006.01) | |
| *C40B 30/04* | (2006.01) | |
| *C40B 40/06* | (2006.01) | |

(52) U.S. Cl.
CPC ........ *C12Q 1/6886* (2013.01); *C12Q 2600/106* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. | |
| 4,196,265 A | 4/1980 | Koprowski et al. | |
| 4,608,337 A | 8/1986 | Croce | |
| 4,693,975 A | 9/1987 | Kozbor et al. | |
| 4,701,409 A | 10/1987 | Croce | |
| 5,015,568 A | 5/1991 | Tsujimoto et al. | |
| 5,149,628 A | 9/1992 | Croce | |
| 5,198,338 A | 3/1993 | Croce | |
| 5,202,429 A | 4/1993 | Tsujimoto et al. | |
| 5,459,251 A | 10/1995 | Tsujimoto et al. | |
| 5,506,106 A | 4/1996 | Croce et al. | |
| 5,506,344 A | 4/1996 | Tsujimoto et al. | |
| 5,523,393 A | 6/1996 | Tsujimoto et al. | |
| 5,567,586 A | 10/1996 | Croce | |
| 5,595,869 A | 1/1997 | Tsujimoto et al. | |
| 5,633,135 A | 5/1997 | Croce et al. | |
| 5,633,136 A | 5/1997 | Croce et al. | |
| 5,674,682 A | 10/1997 | Croce et al. | |
| 5,688,649 A | 11/1997 | Croce et al. | |
| 5,695,944 A | 12/1997 | Croce et al. | |
| 5,928,884 A | 7/1999 | Croce et al. | |
| 5,939,258 A | 8/1999 | Croce et al. | |
| 5,985,598 A | 11/1999 | Russo et al. | |
| 6,040,140 A | 3/2000 | Croce et al. | |
| 6,130,201 A | 10/2000 | Croce et al. | |
| 6,187,536 B1 | 2/2001 | Weinberg et al. | |
| 6,242,212 B1 | 6/2001 | Croce et al. | |
| 6,255,293 B1 | 7/2001 | Kimchi | |
| 6,258,541 B1 | 7/2001 | Chapkin et al. | |
| 6,774,217 B1 | 8/2004 | Croce et al. | |
| 6,924,414 B2 | 8/2005 | Croce et al. | |
| 7,060,811 B2 | 6/2006 | Aldaz et al. | |
| 7,141,417 B1 | 11/2006 | Croce et al. | |
| 7,175,995 B1 | 2/2007 | Russo et al. | |
| 7,217,568 B2 | 5/2007 | Jamieson et al. | |
| 7,220,834 B2 | 5/2007 | Croce et al. | |
| 7,232,806 B2 | 6/2007 | Tuschl et al. | |
| 7,390,792 B2 | 6/2008 | Srivastava et al. | |
| 7,455,995 B2 | 11/2008 | Tanner et al. | |
| 7,585,969 B2 | 9/2009 | Stoffel et al. | |
| 7,592,441 B2 | 9/2009 | Bentwich et al. | |
| 7,618,814 B2 | 11/2009 | Bentwich et al. | |
| 7,642,348 B2 | 1/2010 | Bentwich et al. | |
| 7,667,090 B2 | 2/2010 | Croce | |
| 7,670,840 B2 | 3/2010 | Croce et al. | |
| 7,709,616 B2 | 5/2010 | Bentwich et al. | |
| 7,723,030 B2 | 5/2010 | Croce et al. | |
| 7,723,035 B2 | 5/2010 | Croce et al. | |
| 7,728,189 B2 | 6/2010 | Croce | |
| 7,749,715 B2 | 7/2010 | Russo et al. | |
| 7,777,005 B2 | 8/2010 | Croce et al. | |
| 7,811,759 B2 | 10/2010 | Han | |
| 7,888,010 B2 | 2/2011 | Brown et al. | |
| 7,919,245 B2 | 4/2011 | Brown et al. | |
| 8,084,199 B2 | 12/2011 | Croce et al. | |
| 8,361,710 B2 | 1/2013 | Croce et al. | |
| 8,691,232 B2 | 4/2014 | Derynck et al. | |
| 8,709,732 B2 | 4/2014 | Lo et al. | |
| 8,728,745 B2 | 5/2014 | Martin et al. | |
| 2005/0013247 A | 1/2001 | Sipola et al. | |
| 2001/0026796 A1 | 10/2001 | Croce et al. | |
| 2002/0086331 A1 | 7/2002 | Croce et al. | |
| 2002/0116726 A1 | 8/2002 | Croce et al. | |
| 2002/0132290 A1 | 9/2002 | Frazer | |

(Continued)

FOREIGN PATENT DOCUMENTS

| | | |
|---|---|---|
| AU | 2007/243475 B2 | 5/2013 |
| CA | 2533701 A1 | 2/2005 |

(Continued)

OTHER PUBLICATIONS

Tockman et al (Cancer Res., 1992, 52:2711s-2718s).*

(Continued)

*Primary Examiner* — Catherine S Hibbert

(74) *Attorney, Agent, or Firm* — MacMillan, Sobanski & Todd, LLC

(57) ABSTRACT

Described herein are methods for diagnosing ovarian cancer. In particular, certain microRNAs are useful to the response to chemotherapy of ovarian cancer patients.

9 Claims, 20 Drawing Sheets

(18 of 20 Drawing Sheet(s) Filed in Color)

(56) References Cited

U.S. PATENT DOCUMENTS

| | | |
|---|---|---|
| 2003/0143646 A1 | 7/2003 | Laskey et al. |
| 2003/0206958 A1 | 11/2003 | Cattaneo et al. |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0116321 A1 | 6/2006 | Robbins et al. |
| 2006/0121085 A1 | 6/2006 | Warren et al. |
| 2006/0127895 A1 | 6/2006 | Sabapathy |
| 2006/0134639 A1 | 6/2006 | Huffel et al. |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0199233 A1 | 9/2006 | Dahlberg et al. |
| 2006/0247448 A1 | 11/2006 | Boivin et al. |
| 2006/0292616 A1 | 12/2006 | Neely et al. |
| 2007/0015841 A1 | 1/2007 | Tawa et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023149 A1 | 1/2009 | Knudsen et al. |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0220589 A1 | 9/2009 | Trieu et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0239818 A1 | 9/2009 | Cheng |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004320 A1 | 1/2010 | Elmen et al. |
| 2010/0004322 A1 | 1/2010 | Croce |
| 2010/0021734 A1 | 1/2010 | Uemoto et al. |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0151480 A1 | 6/2010 | Taylor et al. |
| 2010/0173319 A1 | 7/2010 | Croce et al. |
| 2010/0179213 A1 | 7/2010 | Patrawala et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0285471 A1 | 11/2010 | Croce et al. |
| 2010/0298151 A1* | 11/2010 | Taylor et al. .................. 506/2 |
| 2010/0298410 A1 | 11/2010 | Obad et al. |
| 2010/0305188 A1 | 12/2010 | Nakano et al. |
| 2010/0317610 A1 | 12/2010 | Croce |
| 2011/0003704 A1 | 1/2011 | Skog et al. |
| 2011/0021601 A1 | 1/2011 | Park et al. |
| 2011/0054006 A1 | 3/2011 | Slack et al. |
| 2011/0054009 A1 | 3/2011 | Croce et al. |
| 2011/0107440 A1 | 5/2011 | Pivaresi et al. |
| 2011/0136124 A1 | 6/2011 | Roa et al. |
| 2011/0166200 A1 | 7/2011 | Zhang |
| 2011/0251150 A2 | 10/2011 | Bennett et al. |
| 2011/0275534 A1 | 11/2011 | Cohn et al. |
| 2012/0309645 A1* | 12/2012 | Keller et al. .................. 506/9 |
| 2013/0287772 A1* | 10/2013 | Halbert ............... C12Q 1/6883 424/134.1 |
| 2014/0162888 A1* | 6/2014 | Kuslich ............... C12Q 1/6886 506/9 |

FOREIGN PATENT DOCUMENTS

| | | |
|---|---|---|
| CA | 2587189 A1 | 12/2006 |
| CN | 1719973 A | 1/2006 |
| CN | 101215560 B | 9/2010 |
| CN | 1282422 A | 1/2011 |
| EP | 1662259 A1 | 5/2006 |

(56) References Cited

FOREIGN PATENT DOCUMENTS

| | | |
|---|---|---|
| EP | 1676914 A1 | 7/2006 |
| EP | 1795203 A2 | 6/2007 |
| EP | 2354246 A1 | 8/2011 |
| EP | 2487240 A1 | 8/2012 |
| EP | 2481806 A3 | 10/2012 |
| FR | 2877350 A1 | 5/2006 |
| JP | 2005/503827 A | 2/2005 |
| JP | 2005/517452 A | 6/2005 |
| JP | 2005/192484 A | 7/2005 |
| JP | 2005/296014 A | 10/2005 |
| JP | 2008/086201 A | 4/2008 |
| JP | 5395439 B2 | 1/2014 |
| WO | 90/15156 A1 | 12/1990 |
| WO | 91/00364 A1 | 1/1991 |
| WO | 91/07424 A1 | 5/1991 |
| WO | 93/12136 A1 | 6/1993 |
| WO | 94/10343 A1 | 5/1994 |
| WO | 94/24308 A1 | 10/1994 |
| WO | 94/26930 A1 | 11/1994 |
| WO | 96/13514 A1 | 5/1996 |
| WO | 96/35124 A1 | 11/1996 |
| WO | 97/29119 A1 | 8/1997 |
| WO | 98/09510 A1 | 3/1998 |
| WO | 00/03685 A2 | 1/2000 |
| WO | 00/50565 A2 | 8/2000 |
| WO | 00/55169 A1 | 9/2000 |
| WO | 00/076524 A1 | 12/2000 |
| WO | 01/07914 A1 | 2/2001 |
| WO | 01/44466 A1 | 6/2001 |
| WO | 01/68666 A1 | 9/2001 |
| WO | 01/77343 A1 | 10/2001 |
| WO | 01/87958 A2 | 11/2001 |
| WO | 02/064171 A1 | 8/2002 |
| WO | 02/064172 A2 | 8/2002 |
| WO | 03/029459 A2 | 4/2003 |
| WO | 03/078662 A1 | 9/2003 |
| WO | 03/092370 A1 | 11/2003 |
| WO | 2004/033659 A2 | 4/2004 |
| WO | 2004/043387 A2 | 5/2004 |
| WO | 2004/079013 A1 | 9/2004 |
| WO | 2004/098377 A2 | 11/2004 |
| WO | 2005/013901 A3 | 2/2005 |
| WO | 2005/017711 A2 | 2/2005 |
| WO | 2005/020795 A2 | 3/2005 |
| WO | 2005/060661 A2 | 7/2005 |
| WO | 2005/078139 A2 | 8/2005 |
| WO | 2005/079397 A2 | 9/2005 |
| WO | 2005/080601 A2 | 9/2005 |
| WO | 2005/094263 A2 | 10/2005 |
| WO | 2005/103298 A2 | 11/2005 |
| WO | 2005/111211 A2 | 11/2005 |
| WO | 2005/118806 A2 | 12/2005 |
| WO | 2006/105486 A2 | 10/2006 |
| WO | 2006/108718 A1 | 10/2006 |
| WO | 2006/119266 A2 | 11/2006 |
| WO | 2006/119365 A3 | 11/2006 |
| WO | 2006/133022 A2 | 12/2006 |
| WO | 2006/137941 A2 | 12/2006 |
| WO | 2007/016548 A2 | 2/2007 |
| WO | 2007/033023 A2 | 3/2007 |
| WO | 2007/044413 A2 | 4/2007 |
| WO | 2007/073737 A1 | 7/2007 |
| WO | 2007/081680 A2 | 7/2007 |
| WO | 2007/081720 A2 | 7/2007 |
| WO | 2007/081740 A2 | 7/2007 |
| WO | 2007/084486 A2 | 7/2007 |
| WO | 2007/109236 A2 | 9/2007 |
| WO | 2007/112097 A2 | 10/2007 |
| WO | 2007/112754 A2 | 10/2007 |
| WO | 2007/115134 A2 | 10/2007 |
| WO | 2007/127190 A2 | 11/2007 |
| WO | 2008/008430 A2 | 1/2008 |
| WO | 2008/029295 A2 | 3/2008 |
| WO | 2008/036168 A2 | 3/2008 |
| WO | 2008/036776 A2 | 3/2008 |
| WO | 2008/054828 A2 | 5/2008 |
| WO | 2008/064519 A1 | 6/2008 |
| WO | 2008/068047 A1 | 6/2008 |
| WO | 2008/070082 A2 | 6/2008 |
| WO | 2008/073915 A2 | 6/2008 |
| WO | 2008/073920 A2 | 6/2008 |
| WO | 2008/094545 A2 | 8/2008 |
| WO | 2008/097277 A2 | 8/2008 |
| WO | 2008/136971 A1 | 11/2008 |
| WO | 2008/153987 A2 | 12/2008 |
| WO | 2008/157319 A1 | 12/2008 |
| WO | 2009/018303 A2 | 2/2009 |
| WO | 2009/020905 A2 | 2/2009 |
| WO | 2009/026487 A1 | 2/2009 |
| WO | 2009/033140 A1 | 3/2009 |
| WO | 2009/036236 A1 | 3/2009 |
| WO | 2009/049129 A1 | 4/2009 |
| WO | 2009/055773 A2 | 4/2009 |
| WO | 2009/064590 A2 | 5/2009 |
| WO | 2009/070653 A2 | 6/2009 |
| WO | 2009/100029 A1 | 8/2009 |
| WO | 2009/108853 A1 | 9/2009 |
| WO | 2009/108856 A2 | 9/2009 |
| WO | 2009/108860 A2 | 9/2009 |
| WO | 2009/108866 A2 | 9/2009 |
| WO | 2009/152300 A1 | 12/2009 |
| WO | 2010/012667 A1 | 2/2010 |
| WO | 2010/019694 A1 | 2/2010 |
| WO | 2010/059779 A1 | 5/2010 |
| WO | 2010/065156 A1 | 6/2010 |
| WO | 2010/099161 A1 | 9/2010 |
| WO | 2011/057304 A2 | 5/2011 |
| WO | 2011/059776 A2 | 5/2011 |
| WO | 2011/063382 A1 | 5/2011 |
| WO | 2011/119553 A2 | 9/2011 |
| WO | 2011/163116 A3 | 12/2011 |
| WO | 2012/019053 A2 | 2/2012 |
| WO | 2012/065049 A2 | 5/2012 |
| WO | 2012/097047 A1 | 7/2012 |
| WO | 2012/122239 A1 | 9/2012 |

OTHER PUBLICATIONS

Australian Examination Report No. 2, Application No. 2007314212 dated Apr. 29, 2013.
Australian Examination Report No. 3, Application No. 2007205257 dated Jan. 9, 2013.
Australian Examination Report No. 2, Application No. 2007272947 dated May 21, 2012.
Australian Examination Report No. 2, Application No. 2007205163 dated Nov. 15, 2012.
Australian Examination Report No. 1, Application No. 2008248319 dated Jul. 12, 2012.
Australian Examination Report No. 3, Application No. 2006291165 dated Sep. 12, 2012.
Australian Examination Report No. 1, Application No. 2007346101 dated Jun. 21, 2012.
Australian Examination Report No. 2, Application No. 2007205257 dated Jul. 16, 2012.
Australian Examination Report No. 1, Application No. 2007227423 dated Apr. 13, 2012.
Australian Examination Report No. 1, Application No. 2007314212 dated Aug. 28, 2012.
Australian Examination Report No. 2, Application No. 2009281969 dated Jun. 30, 2014.
Australian Examination Report No. 1, Application No. 2008262252 dated Feb. 15, 2013.
Australian Examination Report No. 1, Application No. 2009281969 dated Jan. 16, 2014.
Australian Examination Report No. 3, Application No. 2007205163 dated Mar. 28, 2013.
Australian Examination Report No. 4, Application No. 2006291165 dated Jan. 7, 2013.
Australian Examination Report No. 1, Application No. 2008316577 dated Feb. 11, 2013.

(56) References Cited

OTHER PUBLICATIONS

Australian Examination Report No. 1, Application No. 2008310704 dated Jun. 24, 2013.
Australian Examination Report No. 2, Application No. 2008248319 dated Apr. 9, 2013.
Australian Examination Report No. 2, Application No. 2008282318 dated Nov. 19, 2013.
Australian Examination Report No. 1, Application No. 2007205257 dated Oct. 24, 2011.
Australian Examination Report No. 1, Application No. 2008282318 dated Feb. 7, 2013.
Australian Examination Report No. 2, Application No. 2007227423 dated Mar. 1, 2013.
Australian Examination Report No. 1, Application No. 2008283997 dated Aug. 20, 2007.
Australian Examination Report No. 1, Application No. 2008266014 dated Jul. 6, 2012.
Australian Examination Report No. 2, Application No. 2008288806 dated Mar. 25, 2014.
Australian Examination Report No. 1, Application No. 2007205234 dated Jun. 17, 2011.
Australian Examination Report No. 1, Application No. 2007242475 dated Mar. 30, 2012.
Australian Examination Report No. 1, Application No. 2009219197 dated Sep. 19, 2013.
Australian Examination Report No. 2, Application No. 2007346101 dated May 24, 2013.
Australian Examination Report No. 2, Application No. 2006291165 dated Feb. 13, 2012.
Canadian Office Action, Application No. 2,617,581 dated Feb. 1, 2011.
Canadian Office Action, Application No. 2,621,441 dated Apr. 8, 2013.
Canadian Office Action, Application No. 2,657,030 dated Jan. 13, 2014.
Canadian Office Action, Application No. 2,811,486 dated Aug. 6, 2014.
Canadian Office Action, Application No. 2,667,617 dated Jan. 2, 2014.
Canadian Office Action, Application No. 2,646,051 dated Feb. 25, 2011.
Canadian Office Action, Application No. 2,685,840 dated Jun. 5, 2014.
Canadian Office Action, Application No. 2,621,441 dated Feb. 1, 2011.
Canadian Office Action, Application No. 2,635,616 dated Feb. 27, 2012.
Canadian Office Action, Application No. 2,617,581 dated Apr. 2, 2012.
Chinese 1st Office Action, Application No. 200780023093.8 dated Dec. 27, 2010.
Chinese 1st Office Action, Application No. 200980114564.5 dated Dec. 19, 2013.
Chinese 1st Office Action, Application No. 201080059339.9 dated Aug. 26, 2013.
Chinese 1st Office Action, Application No. 200780033066.9 dated Sep. 18, 2011.
Chinese 1st Office Action, Application No. 200980126520.4 dated Dec. 4, 2012.
Chinese 1st Office Action, Application No. 200980112966.1 dated Sep. 20, 2012.
Chinese 1st Office Action, Application No. 200980155340.9 dated Jan. 21, 2013.
Chinese 1st Office Action, Application No. 201210380806.9 dated Nov. 5, 2013.
Chinese 1st Office Action, Application No. 200880022612.3 dated Apr. 24, 2012.
Chinese 1st Office Action, Application No. 200880108625.2 dated Feb. 13, 2012.
Chinese 1st Office Action, Application No. 200880112581.0 dated Aug. 13, 2012.
Chinese 1st Office Action, Application No. 200780040146.7 dated May 25, 2011.
Chinese 1st Office Action, Application No. 200980113258.X dated Mar. 13, 2013.
Chinese 1st Office Action, Application No. 1180022637.5 dated Aug. 20, 2014.
Chinese 1st Office Action, Application No. 201110319534.7 dated Jun. 8, 2013.
Chinese 1st Office Action, Application No. 201310396056.9 dated Jul. 31, 2014.
Chinese 1st Office Action, Application No. 200780005821.2 dated Jan. 26, 2011.
Chinese 1st Office Action, Application No. 200880025276.8 dated Nov. 23, 2011.
Chinese 1st Office Action, Application No. 200880119206.9 dated May 3, 2012.
Chinese 1st Office Action, Application No. 200880112585.9 dated May 24, 2012.
Chinese 1st Office Action, Application No. 200880116343.7 dated Jan. 31, 2012.
Chinese 1st Office Action, Application No. 200780018496.3 dated Mar. 22, 2011.
Chinese 1st Office Action, Application No. 200880103023.8 dated Oct. 9, 2012.
Chinese 1st Office Action, Application No. 200880108689.2 dated Feb. 13, 2012.
Chinese 1st Office Action, Application No. 200980111708.1 dated Aug. 27, 2012.
Chinese 1st Office Action, Application No. 200780005791.5 dated Mar. 24, 2011.
Chinese 1st Office Action, Application No. 200980135456.6 dated Nov. 13, 2012.
Chinese 1st Office Action, Application No. 201210312507.1 dated Jul. 29, 2013.
Chinese 1st Office Action, Application No. 201310230787.6 dated May 19, 2014.
Chinese 2nd Office Action, Application No. 200880112581.0 dated May 10, 2013.
Chinese 2nd Office Action, Application No. 200880003736.7 dated Nov. 5, 2012.
Chinese 2nd Office Action, Application No. 200880025276.8 dated Aug. 1, 2012.
Chinese 2nd Office Action, Application No. 200980126520.4 dated Aug. 14, 2013.
Chinese 2nd Office Action, Application No. 200780005791.5 dated May 3, 2012.
Chinese 2nd Office Action, Application No. 200980135456.6 dated Aug. 1, 2013.
Chinese 2nd Office Action, Application No. 200980155340.9 dated Aug. 26, 2013.
Chinese 2nd Office Action, Application No. 200880103023.8 dated Jun. 20, 2013.
Chinese 2nd Office Action, Application No. 200680039776.8 dated Jun. 30, 2011.
Chinese 2nd Office Action, Application No. 200880022612.3 dated Oct. 29, 2012.
Chinese 2nd Office Action, Application No. 200880108689.2 dated Sep. 12, 2012.
Chinese 2nd Office Action, Application No. 200880108625.2 dated Aug. 21, 2012.
Chinese 2nd Office Action, Application No. 200880119206.9 dated Feb. 1, 2013.
Chinese 2nd Office Action, Application No. 201210380806.9 dated Jun. 23, 2014.
Chinese 2nd Office Action, Application No. 200780033066.9 dated Jun. 26, 2012.
Chinese 2nd Office Action, Application No. 200880116343.7 dated Oct. 22, 2012.
Chinese 2nd Office Action, Application No. 200780018496.3 dated Mar. 1, 2012.

(56) References Cited

OTHER PUBLICATIONS

Chinese 2nd Office Action, Application No. 200880112585.9 dated Jan. 21, 2013.
Chinese 2nd Office Action, Application No. 200780040146.7 dated Dec. 31, 2011.
Chinese 2nd Office Action, Application No. 200780023093.8 dated Dec. 9, 2011.
Chinese 2nd Office Action, Application No. 200980112966.1 dated May 9, 2013.
Chinese 2nd Office Action, Application No. 200680036598.3 dated Feb. 24, 2011.
Chinese 2nd Office Action, Application No. 201080059339.9 dated Apr. 9, 2014.
Chinese 2nd Office Action, Application No. 200980111708.1 dated May 20, 2013.
Chinese 2nd Office Action, Application No. 200780005821.2 dated Apr. 1, 2012.
Chinese 3rd Office Action, Application No. 200880108689.2 dated Apr. 1, 2013.
Chinese 3rd Office Action, Application No. 200780023093.8 dated Jul. 2, 2012.
Chinese 3rd Office Action, Application No. 200780005791.5 dated Dec. 5, 2012.
Chinese 3rd Office Action, Application No. 200880003736.7 dated Apr. 12, 2013.
Chinese 3rd Office Action, Application No. 200780005821.2 dated Nov. 5, 2012.
Chinese 3rd Office Action, Application No. 200780040146.7 dated Apr. 25, 2012.
Chinese 3rd Office Action, Application No. 200880022612.3 dated May 17, 2013.
Chinese 3rd Office Action, Application No. 200780033066.9 dated Dec. 17, 2012.
Chinese 3rd Office Action, Application No. 200880108625.2 dated Jan. 5, 2013.
Chinese 3rd Office Action, Application No. 200980111708.1 dated Nov. 4, 2013.
Chinese 3rd Office Action, Application No. 200880116343.7 dated Apr. 8, 2013.
Chinese 3rd Office Action, Application No. 200980113258.X dated Jun. 10, 2014.
Chinese 3rd Office Action, Application No. 200980126520.4 dated Feb. 18, 2014.
Chinese 3rd Office Action, Application No. 200980135456.6 dated Feb. 8, 2014.
Chinese 3rd Office Action, Application No. 200980112966.1 dated Dec. 4, 2013.
Chinese 3rd Office Action, Application No. 200880119206.9 dated Aug. 12, 2013.
Chinese 4th Office Action, Application No. 200780040146.7 dated Nov. 23, 2012.
Chinese 4th Office Action, Application No. 200780023093.8 dated Jan. 14, 2013.
Chinese 4th Office Action, Application No. 200880022612.3 dated Nov. 19, 2013.
Chinese 4th Office Action, Application No. 200780005821.2 dated May 13, 2013.
Chinese 4th Office Action, Application No. 200880116343.7 dated Jul. 10, 2013.
Chinese 5th Office Action, Application No. 200780040146.7 dated Apr. 16, 2013.
Chinese Rejection Decision, Application No. 200780033066.9 dated Jun. 13, 2013.
Chinese Rejection Decision, Application No. 200880103023.8 dated Feb. 13, 2014.
Chinese Rejection Decision, Application No. 200980135456.6 dated Aug. 26, 2014.
Chinese Rejection Decision, Application No. 200780018496.3 dated Sep. 5, 2012.
European Examination Report, Application No. 12154350.8 dated Aug. 21, 2013.
European Examination Report, Application No. 12179592.6 dated May 12, 2014.
European Examination Report, Application No. 12154347.4 dated Oct. 9, 2013.
European Examination Report, Application No. 07867402.5 dated Nov. 22, 2011.
European Examination Report, Application No. 12165748.0 dated Sep. 17, 2013.
European Examination Report, Application No. 12154337.5 dated May 19, 2014.
European Examination Report, Application No. 07753450.1 dated Jan. 12, 2009.
European Examination Report, Application No. 12179595.9 dated May 12, 2014.
European Examination Report, Application No. 12165638.3 dated Apr. 2, 2014.
European Examination Report, Application No. 12154354.0 dated Oct. 23, 2013.
European Examination Report, Application No. 12165740.7 dated Apr. 28, 2014.
European Examination Report, Application No. 09713926.5 dated Jul. 30, 2012.
European Examination Report, Application No. 12165734.0 dated Aug. 14, 2013.
European Examination Report, Application No. 12165734.0 dated Apr. 29, 2014.
European Examination Report, Application No. 09715064.3 dated Feb. 12, 2014.
European Examination Report, Application No. 12185438.4 dated Sep. 18, 2013.
European Examination Report, Application No. 08796821.0 dated Jan. 7, 2013.
European Examination Report, Application No. 08767439.6 dated Mar. 15, 2011.
European Examination Report, Application No. 08782609.5 dated Jun. 24, 2011.
European Examination Report, Application No. 08782609.5 dated May 24, 2012.
European Examination Report, Application No. 12154298.9 dated Nov. 22, 2013.
European Examination Report, Application No. 09830750.7 dated Apr. 18, 2013.
European Examination Report, Application No. 12154342.5 dated Mar. 20, 2014.
European Examination Report, Application No. 07716208.9 dated Sep. 27, 2010.
European Examination Report, Application No. 12154246.8 dated Nov. 22, 2013.
European Examination Report, Application No. 07716208.9 dated Apr. 20, 2010.
European Examination Report, Application No. 07717903.4 dated Jan. 29, 2010.
European Examination Report, Application No. 08770974.7 dated Feb. 25, 2013.
European Examination Report, Application No. 07717903.4 dated Aug. 16, 2011.
European Examination Report, Application No. 07867402.5 dated Jan. 5, 2011.
European Examination Report, Application No. 07810382.7 dated Dec. 8, 2010.
European Examination Report, Application No. 07716208.9 dated Sep. 13, 2012.
European Examination Report, Application No. 12154343.3 dated Mar. 21, 2014.
European Examination Report, Application No. 06800599.0 dated Jul. 25, 2014.
European Examination Report, Application No. 12154339.1 dated May 16, 2014.
European Examination Report, Application No. 08768266.2 dated Apr. 18, 2011.

(56) References Cited

OTHER PUBLICATIONS

European Examination Report, Application No. 07867402.5 dated Apr. 10, 2012.
European Examination Report, Application No. 12154329.2 dated May 26, 2014.
European Examination Report, Application No. 12154348.2 dated Oct. 9, 2013.
European Examination Report, Application No. 11151749.6 dated Dec. 10, 2012.
European Examination Report, Application No. 11151771.0 dated Jan. 3, 2013.
European Examination Report, Application No. 09715356.3 dated Jul. 10, 2013.
European Examination Report, Application No. 12154346.6 dated Jun. 27, 2013.
European Examination Report, Application No. 08796821.0 dated Jul. 19, 2013.
European Examination Report, Application No. 08799295.4 dated Dec. 10, 2012.
European Examination Report, Application No. 11170608.1 dated May 3, 2012.
European Examination Report, Application No. 08841700.1 dated Jun. 1, 2012.
European Examination Report, Application No. 08768266.2 dated Jul. 29, 2010.
European Examination Report, Application No. 12154341.7 dated Aug. 9, 2013.
European Examination Report, Application No. 08841700.1 dated Jun. 13, 2014.
European Examination Report, Application No. 11151769.4 dated Jan. 3, 2013.
European Examination Report, Application No. 12154304.5 dated Feb. 25, 2013.
European Examination Report, Application No. 12154327.6 dated May 26, 2014.
European Examination Report, Application No. 12154322.7 dated May 27, 2014.
European Examination Report, Application No. 11196265.0 dated Feb. 22, 2013.
European Examination Report, Application No. 09715064.3 dated Nov. 5, 2012.
European Examination Report, Application No. 13159600.9 dated May 15, 2014.
European Examination Report, Application No. 07716208.9 dated Sep. 13, 2011.
European Examination Report, Application No. 07717903.4 dated Apr. 25, 2012.
European Examination Report, Application No. 12154307.8 dated Feb. 20, 2013.
European Examination Report, Application No. 08798444.9 dated May 15, 2014.
European Examination Report, Application No. 12154321.9 dated May 26, 2014.
European Examination Report, Application No. 06814375.9 dated Oct. 14, 2011.
European Examination Report, Application No. 08799295.4 dated Nov. 18, 2011.
European Examination Report, Application No. 08767439.6 dated Dec. 2, 2011.
European Examination Report, Application No. 06800599.0 dated Nov. 25, 2011.
European Examination Report, Application No. 12154334.2 dated May 16, 2014.
European Extended Search Report, Application No. 11840508.3 dated Mar. 19, 2014.
European Extended Search Report, Application No. 12165636.7 dated Sep. 25, 2012.
European Extended Search Report, Application No. 12154353.2 dated Jan. 31, 2013.
European Extended Search Report, Application No. 11760035.3 dated Jul. 24, 2014.
European Extended Search Report, Application No. 131754731 dated Jul. 2, 2014.
European Extended Search Report, Application No. 12185446.7 dated Mar. 28, 2013.
European Extended Search Report, Application No. 07867402.5 dated Nov. 24, 2009.
European Extended Search Report, Application No. 12154352.4 dated Jan. 28, 2013.
European Extended Search Report, Application No. 12154343.3 dated Jul. 10, 2012.
European Extended Search Report, Application No. 12165748.0 dated Jan. 11, 2013.
European Extended Search Report, Application No. 12165740.7 dated Jan. 11, 2013.
European Extended Search Report, Application No. 12165734.0 dated Jan. 11, 2013.
European Extended Search Report, Application No. 12154351.6 dated Jan. 31, 2013.
European Extended Search Report, Application. No. 12154246.8 dated Jun. 4, 2012.
European Extended Search Report, Application No. 08767439.6 dated May 12, 2010.
European Extended Search Report, Application No. 12154354.0 dated Jan. 28, 2013.
European Extended Search Report, Application No. 12179595.9 dated Jan. 23, 2013.
European Extended Search Report, Application No. 12154349.0 dated Jan. 25, 2013.
European Extended Search Report, Application No. 12154350.8 dated Jan. 25, 2013.
European Extended Search Report, Application No. 12154301.1 dated Jan. 11, 2013.
European Extended Search Report, Application No. 12154300.3 dated Dec. 7, 2012.
European Extended Search Report, Application No. 12755097.8 dated Aug. 4, 2014.
European Extended Search Report, Application No. 10832355.1 dated May 13, 2014.
European Extended Search Report, Application No. 12185438.4 dated Mar. 28, 2013.
European Extended Search Report, Application No. 07776079.1 dated Sep. 6, 2011.
European Extended Search Report, Application No. 13175161.2 dated Sep. 24, 2013.
European Extended Search Report, Application No. 13159600.9 dated Sep. 19, 2013.
European Extended Search Report, Application No. 12179592.6 dated Jan. 21, 2013.
European Search Report, Application No. 12165636.7 dated Jun. 8, 2012.
European Search Report, Application No. 11196250.2 dated Apr. 24, 2012.
European Search Report, Application No. 11196253.6 dated Apr. 24, 2012.
European Search Report, Application No. 06825457.2 dated Sep. 16, 2009.
European Search Report, Application No. 07872618.9 dated Jul. 5, 2010.
European Search Report, Application No. 07716208.9 dated Nov. 10, 2009.
European Search Report, Application No. 07717734.3 dated Nov. 9, 2009.
European Search Report, Application No. 11151769.4 dated Aug. 2, 2011.
European Search Report, Application No. 07717903.4 dated Oct. 23, 2009.
European Search Report, Application No. 12154298.9 dated Jun. 4, 2012.
European Search Report, Application No. 11196190.0 dated Apr. 24, 2012.

(56) References Cited

OTHER PUBLICATIONS

European Search Report, Application No. 06800599.0 dated Oct. 19, 2009.
European Search Report, Application No. 08768266.2 dated Jul. 1, 2010.
European Search Report, Application No. 07717903.4 dated Nov. 10, 2009.
European Search Report, Application No. 11151749.6 dated Aug. 2, 2011.
European Search Report, Application No. 07867402.5 dated Mar. 16, 2010.
European Search Report, Application No. 06814375.9 dated Oct. 8, 2009.
European Search Report, Application No. 12154304.5 dated Jun. 26, 2012.
European Search Report, Application No. 12165638.3 dated Jun. 12, 2012.
European Search Report, Application No. 08782609.5 dated Oct. 28, 2010.
European Search Report, Application No. 08713330.2 dated Jul. 22, 2011.
European Search Report, Application No. 09715064.3 dated May 24, 2011.
European Search Report, Application No. 08798444.9 dated Dec. 16, 2010.
European Search Report, Application No. 09713926.5 dated Jul. 21, 2011.
European Search Report, Application No. 08799295.4 dated Nov. 9, 2010.
European Search Report, Application No. 09714868.8 dated Aug. 1, 2011.
European Search Report, Application No. 08841700.1 dated Jun. 2, 2010.
European Search Report, Application No. 08796821.0 dated Aug. 4, 2010.
European Search Report, Application No. 11170608.1 dated Aug. 29, 2011.
European Search Report, Application No. 08770974.4 dated Oct. 21, 2011.
European Search Report, Application No. 11196256.9 dated Feb. 28, 2012.
European Search Report, Application No. 12154321.9 dated Jul. 20, 2012.
European Search Report, Application No. 08841700.1 dated Jan. 4, 2011.
European Search Report, Application No. 11196254.4 dated Feb. 28, 2012.
European Search Report, Application No. 11196264.3 dated Feb. 28, 2012.
European Search Report, Application No. 11196261.9 dated Feb. 28, 2012.
European Search Report, Application No. 11196262.7 dated Feb. 28, 2012.
European Search Report, Application No. 07810382.7 dated Sep. 14, 2009.
European Search Report, Application No. 11151771.0 dated Aug. 2, 2011.
European Search Report, Application No. 11196265.0 dated Mar. 5, 2012.
European Search Report, Application No. 11151772.8 dated Aug. 2, 2011.
European Search Report, Application No. 12154348.2 dated Oct. 9, 2012.
European Search Report, Application No. 09763590.8 dated Aug. 29, 2011.
European Search Report, Application No. 12154352.4 dated Oct. 12, 2012.
European Search Report, Application No. 12154347.4 dated Sep. 27, 2012.
European Search Report, Application No. 12154354.0 dated Oct. 12, 2012.
European Search Report, Application No. 07867402.5 dated Dec. 11, 2009.
European Search Report, Application No. 12185440.0 dated Apr. 12, 2013.
European Search Report, Application No. 12154337.5 dated Oct. 9, 2012.
European Search Report, Application No. 12154327.6 dated Sep. 19, 2012.
European Search Report, Application No. 12154344.1 dated Sep. 19, 2012.
European Search Report, Application No. 12154350.8 dated Sep. 27, 2012.
European Search Report, Application No. 12154345.8 dated Sep. 19, 2012.
European Search Report, Application No. 12154346.6 dated Oct. 23, 2012.
European Search Report, Application No. 08838376.5 dated Mar. 4, 2011.
European Search Report, Application No. 12154349.0 dated Sep. 27, 2012.
European Search Report, Application No. 09807241.6 dated Dec. 6, 2012.
European Search Report, Application No. 12154351.6 dated Oct. 15, 2012.
European Search Report, Application No. 12154353.2 dated Oct. 15, 2012.
European Search Report, Application No. 12154339.1 dated Oct. 9, 2012.
European Search Report, Application No. 12154300.3 dated Aug. 20, 2012.
European Search Report, Application No. 12154300.3 dated Jan. 7, 2013.
European Search Report, Application No. 12154307.8 dated Jun. 26, 2012.
European Search Report, Application No. 09715356.3 dated Jul. 12, 2012.
European Search Report, Application No. 12154341.7 dated Oct. 25, 2012.
European Search Report, Application No. 12154342.5 dated Jul. 6, 2012.
European Search Report, Application No. 09830750.7 dated Aug. 27, 2012.
European Search Report, Application No. 12165734.0 dated Aug. 27, 2012.
European Search Report, Application No. 12154322.7 dated Aug. 29, 2012.
European Search Report, Application No. 12154301.1 dated Aug. 22, 2012.
European Search Report, Application No. 12154334.2 dated Sep. 21, 2012.
European Search Report, Application No. 12154332.6 dated Sep. 21, 2012.
European Search Report, Application No. 12154329.2 dated Sep. 19, 2012.
European Search Report, Application No. 12165748.0 dated Aug. 23, 2012.
European Search Report, Application No. 12154326.8 dated Sep. 6, 2012.
European Search Report, Application No. 12165740.7 dated Aug. 27, 2012.
Japanese Notification of Reasons for Rejection, Application No. 2010-506300 dated Apr. 16, 2013.
Japanese Notification of Reasons for Rejection, Application No. 2010-522058 dated Aug. 1, 2014.
Japanese Notification of Reasons for Rejection, Application No. 2009-529212 dated Oct. 17, 2012.
Japanese Notification of Reasons for Rejection, Application No. 2010-512377 dated Jun. 4, 2013.
Japanese Notification of Reasons for Rejection, Application No. 2010-511218 dated Jun. 3, 2013.

(56) References Cited

OTHER PUBLICATIONS

Japanese Notification of Reasons for Rejection, Application No. 2009-535366 dated Dec. 21, 2012.
Japanese Notification of Reasons for Rejection, Application No. 2008-549532 dated Sep. 27, 2013.
Japanese Notification of Reasons for Rejection, Application No. 2010-548904 dated Apr. 1, 2014.
Japanese Notification of Reasons for Rejection, Appliction No. 2011-539528 dated Oct. 25, 2013.
Japanese Notification of Reasons for Rejection, Application No. 2010-548899 dated Oct. 8, 2013.
Japanese Notification of Reasons for Rejection, Application No. 2009-529212 dated Jul. 19, 2013.
Japanese Notification of Reasons for Rejection, Application No. 2010-548907 dated Sep. 2, 2013.
Japanese Notification of Reasons for Rejection, Application No. 2010-548904 dated Sep. 2, 2013.
Japanese Notification of Reasons for Rejection, Application No. 2010-524221 dated Jun. 19, 2013.
Japanese Notification of Reasons for Rejection, Application No. 2010-522058 dated Aug. 13, 2013.
Japanese Notification of Reasons for Rejection, Application No. 2010-511218 dated Mar. 13, 2014.
Japanese Notification of Reasons for Rejection, Application No. 2010-519269 dated Jul. 12, 2013.
Japanese Notification of Reasons for Rejection, Application No. 2010-529072 dated Jul. 30, 2013.
Japanese Notification of Reasons for Rejection, Application No. 2012-183280 dated Mar. 18, 2014.
Japanese Notification of Reasons for Rejection, Application No. 2008-525107 dated Jan. 4, 2012.
Japanese Notification of Reasons for Rejection, Application No. 2010-519269 dated Jun. 23, 2014.
Japanese Notification of Reasons for Rejection, Application No. 2010-529072 dated Jun. 4, 2014.
Japanese Notification of Reasons for Rejection, Application No. 2013-081761 dated May 20, 2014.
Japanese Notification of Reasons for Rejection, Application No. 2009-519525 dated Nov. 1, 2012.
Japanese Notification of Reasons for Rejection, Application No. 2009-548281 dated Sep. 3, 2013.
Japanese Notification of Reasons for Rejection, Application No. 2008-549549 dated Feb. 22, 2012.
Japanese Notification of Reasons for Rejection, Application No. 2008-549532 dated Feb. 24, 2012.
Japanese Notification of Reasons for Rejection, Application No. 2009-519525 dated Jul. 9, 2012.
Japanese Notification of Reasons for Rejection, Application No. 2008-532200 dated Jan. 30, 2012.
Japanese Notification of Reasons for Rejection, Application No. 2008-525107 dated Oct. 19, 2012.
Japanese Notification of Reasons for Rejection, Application No. 2010-531311 dated Sep. 2, 2013.
Japanese Notification of Reasons for Rejection, Application No. 2010-506300 dated Mar. 12, 2014.
Japanese Notification of Reasons for Rejection, Application No. 2011-523144 dated Feb. 6, 2014.
Japanese Notification of Reasons for Rejection, Application No. 2009-501495 dated Jun. 11, 2013.
Japanese Notification of Reasons for Rejection, Application No. 2008-549555 dated Dec. 12, 2012.
Japanese Notification of Reasons for Rejection, Application No. 2012-284018 dated May 21, 2014.
Japanese Notification of Reasons for Rejection, Application No. 2009-501495 dated Jul. 27, 2012.
Japanese Notification of Reasons for Rejection, Application No. 2008-549555 dated Feb. 24, 2012.
Office Action issued in U.S. Appl. No. 12/160,034, filed Jul. 3, 2008, mailing date Jun. 7, 2010.
Office Action issued in U.S. Appl. No. 12/083,067, filed Jun. 20, 2008, mailing date Jul. 8, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,061, filed Jul. 3, 2008, mailing date Mar. 12, 2010.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.
Office Action issued in U.S. Appl. No. 13/405,543, filed Feb. 27, 2012, mailed Jul. 7, 2014.
Office Action issued in U.S. Appl. No. 12/598,270, filed Nov. 16, 2009, mailed Jun. 9, 2014.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
PCT International Preliminary Report on Patentability, PCT/US2007/006824 filed Mar. 19, 2007, dated Sep. 23, 2008.
PCT International Preliminary Report on Patentability, PCT/US2007/000024 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2006/035100 filed Sep. 11, 2006, dated Mar. 18, 2008.
PCT International Preliminary Report on Patentability, PCT/US2007/000103 filed Jan. 3, 2007, dated Jul. 8, 2008.
PCT International Preliminary Report on Patentability, PCT/US2008/081294 filed Oct. 27, 2008, dated Apr. 27, 2010.
PCT International Preliminary Report on Patentability, PCT/US2007/015892 filed Jul. 12, 2007, dated Jan. 13, 2009.
PCT International Preliminary Report on Patentability, PCT/US2006/038824 filed Oct. 4, 2006, dated Apr. 9, 2008.
PCT International Preliminary Report on Patentability, PCT/US2008/079482 filed Oct. 10, 2008, dated Apr. 13, 2010.
PCT International Preliminary Report on Patentability, PCT/US2008/007196 filed Jun. 9, 2008, dated Dec. 11, 2009.
PCT International Preliminary Report on Patentability, PCT/US2009/035470 filed Feb. 27, 2009, dated Aug. 31, 2010.
PCT International Preliminary Report on Patentability, PCT/US2008/073964 filed Aug. 22, 2008, dated Feb. 24, 2010.
PCT International Preliminary Report on Patentability, PCT/US2009/065072 filed Nov. 19, 2009, dated Jun. 3, 2011.
PCT International Preliminary Report on Patentability, PCT/US2011/034451 filed Apr. 29, 2011, dated Nov. 15, 2012.
PCT International Preliminary Report on Patentability, PCT/US2010/025173 filed Feb. 24, 2010, dated Sep. 9, 2011.
PCT International Preliminary Report on Patentability, PCT/US2006/029889 filed Jul. 31, 2006, dated Feb. 5, 2008.
PCT International Preliminary Report on Patentability, PCT/US2009/53586 filed Aug. 12, 2009, dated Feb. 24, 2011.
PCT International Preliminary Report on Patentability, PCT/US2010/057758 filed Nov. 23, 2010, dated Jun. 7, 2012.
PCT International Preliminary Report on Patentability, PCT/US2012/068736, filed Dec. 10, 2012, dated Jun. 19, 2014.
PCT International Preliminary Report on Patentability, PCT/US2009/035463 filed Feb. 27, 2009, dated Aug. 31, 2010.
PCT International Preliminary Report on Patentability, PCT/US2007/020215 filed Sep. 17, 2007, dated Mar. 24, 2009.
PCT International Preliminary Report on Patentability, PCT/US2009/035458 filed Feb. 27, 2009, dated Aug. 31, 2010.
PCT International Preliminary Report on Patentability, PCT/US2007/009910 filed Apr. 24, 2007, dated Oct. 28, 2008.
PCT International Preliminary Report on Patentability, PCT/US2008/075565 filed Sep. 8, 2008, dated Mar. 9, 2010.
PCT International Preliminary Report on Patentability, PCT/US2008/071532 filed Jul. 30, 2008, dated Feb. 2, 2010.
PCT International Preliminary Report on Patentability, PCT/US2008/001157 filed Jan. 29, 2008, dated Aug. 4, 2009.

(56) References Cited

OTHER PUBLICATIONS

PCT International Preliminary Report on Patentability, PCT/US2007/023660 filed Nov. 1, 2007, dated May 5, 2009.
PCT International Preliminary Report on Patentability, PCT/US2009/038214 filed Mar. 25, 2009, dated Jun. 16, 2011.
PCT International Preliminary Report on Patentability, PCT/US2009/035482 filed Feb. 27, 2009, dated Aug. 31, 2010.
PCT International Preliminary Report on Patentability, PCT/US2008/072081 filed Aug. 4, 2008, dated Feb. 9, 2010.
PCT International Preliminary Report on Patentability, PCT/US2008/066870 filed Jun. 13, 2008, dated Dec. 17, 2009.
PCT International Preliminary Report on Patentability, PCT/US2008/005503 filed Apr. 29, 2008, dated Nov. 3, 2009.
PCT International Search Report and the Written Opinion, PCT/US2011/060349 filed Nov. 11, 2011, dated Feb. 10, 2012.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/75565 filed Sep. 8, 2008, dated Dec. 9, 2008.
PCT International Search Report and the Written Opinion, PCT/US2008/05503 filed Apr. 29, 2008, dated Sep. 25, 2008.
PCT International Search Report and the Written Opinion, PCT/US2008/81294 filed Oct. 27, 2008, dated Mar. 26, 2009.
PCT International Search Report and the Written Opinion, PCT/US2009/46999 filed Jun. 11, 2009, dated Nov. 23, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/53586 filed Aug. 12, 2009, dated Oct. 28, 2009.
PCT International Search Report and the Written Opinion, PCT/US2008/79482 filed Oct. 10, 2008, dated Dec. 22, 2008.
PCT International Search Report and the Written Opinion, PCT/US2007/15892 filed Jul. 12, 2007, dated Sep. 30, 2008.
PCT International Search Report and the Written Opinion, PCT/US2012/28016 filed Mar. 7, 2012, dated Aug. 3, 2012.
PCT International Search Report and the Written Opinion, PCT/US2012/020911 filed Jan. 11, 2012, dated Apr. 25, 2012.
PCT International Search Report and the Written Opinion, PCT/US2011/60838 filed Nov. 15, 2011, dated Mar. 21, 2012.
PCT International Search Report and the Written Opinion, PCT/US2012/060225 filed Oct. 15, 2012, dated Jan. 7, 2013.
PCT International Search Report and the Written Opinion, PCT/US2012/67651 filed Dec. 3, 2012, dated May 13, 2013.
PCT International Search Report and the Written Opinion, PCT/US2013/22492 filed Jan. 22, 2013, dated May 20, 2013.
PCT International Search Report and the Written Opinion, PCT/US2012/68736 filed Dec. 10, 2012, dated Apr. 8, 2013.
PCT International Search Report and the Written Opinion, PCT/US2012/69484 filed Dec. 13, 2012, dated Apr. 29, 2013.
PCT International Search Report and the Written Opinion, PCT/US2011/29348 filed Mar. 22, 2011, dated Jun. 3, 2011.
PCT International Search Report and the Written Opinion, PCT/US2011/41046 filed Jun. 20, 2011, dated Mar. 5, 2012.
PCT International Search Report and the Written Opinion, PCT/US2010/025173 filed Feb. 24, 2010, dated Jul. 6, 2010.
PCT International Search Report and the Written Opinion, PCT/US2012/62853 filed Oct. 31, 2012, dated Mar. 14, 2013.
PCT International Search Report and the Written Opinion, PCT/US2008/73964 filed Aug. 22, 2008, dated Dec. 24, 2008.
PCT International Search Report and the Written Opinion, PCT/US2008/01157 filed Jan. 29, 2008, dated Aug. 7, 2008.
PCT International Search Report and the Written Opinion, PCT/US2007/00159 filed Jan. 3, 2007, dated Apr. 11, 2008.
PCT International Search Report and the Written Opinion, PCT/US2007/00103 filed Jan. 3, 2007, dated Dec. 3, 2007.
PCT International Search Report and the Written Opinion, PCT/US2006/29889 filed Jul. 31, 2006, dated Jul. 10, 2007.
PCT International Search Report, PCT/US2007/006824 filed Mar. 19, 2007, dated May 14, 2008.
PCT International Search Report and the Written Opinion, PCT/US2008/84821 filed Nov. 26, 2008, dated Feb. 17, 2009.
PCT International Search Report and the Written Opinion, PCT/US2006/38824 filed Oct. 4, 2006, dated Aug. 9, 2007.
PCT International Search Report and the Written Opinion, PCT/US2006/35100 filed Sep. 11, 2006, dated Sep. 5, 2007.
PCT International Search Report and the Written Opinion, PCT/US2007/00024 filed Jan. 3, 2007, dated Nov. 5, 2007.
PCT International Search Report and the Written Opinion, PCT/US2007/006824 filed Mar. 19, 2007, dated Mar. 3, 2008.
PCT International Search Report and the Written Opinion, PCT/US2007/09910 filed Apr. 24, 2007, dated Feb. 13, 2008.
PCT International Search Report and the Written Opinion, PCT/US2007/23660 filed Nov. 1, 2007, dated Sep. 16, 2008.
PCT International Search Report and the Written Opinion, PCT/US2007/20215 filed Sep. 17, 2007, dated Jul. 25, 2008.
PCT International Search Report and the Written Opinion, PCT/US2009/65072 filed Nov. 19, 2009, dated Mar. 3, 2010.
PCT Written Opinion, PCT/US2009/051942 filed Jul. 28, 2009, dated Jan. 26, 2010.
Ahmad et al., "Distant Metastases of Nasopharyngeal Carcinoma: A Study of 256 Male Patients", Journal of Surgical Oncology, 1986, vol. 33, pp. 194-197.
Aiba, "Pathology of the Breast Carcinoma from the Viewpoint of the Proliferative Activity and Grade of Malignancy", JPN J Cancer Clinical, 2000, vol. 46, No. 5, pp. 475-481.
Akahoshi et al., "Myeloproliferative Disorders Terminating in Acute Megakaryoblastic Leukemia with Chromosome 3q26 Abnormality", Cancer, 1987, vol. 60, pp. 2654-2661.
Akao et al., "let-7 MicroRNA Functions as a Potential Growth Suppressor in Human Colon Cancer Cells", Biological & Pharmaceutical Bulletin, 2006, vol. 29, No. 5, pp. 903-906.
Alberts et al., "Molecular Biology of the Cell", 3rd Edition, 1994, p. 465.
Alvarez-Secord et al., "Maspin Expression in Epithelial Ovarian Cancer and Associations with Poor Prognosis: A Gynecologic Oncology Group Study", Gynecologic Oncology, 2006, vol. 101, pp. 390-397.
Ambros et al., "A Uniform System for MicroRNA Annotation", RNA, 2003, vol. 9, pp. 277-279.
Ambros, "MicroRNA Pathways in Flies and Worms: Growth, Death, Fat, Stress, and Timing", Cell, 2003, vol. 113, pp. 673-676.
Ambs et al., "Genomic Profiling of MicroRNA and Messenger RNA Reveals Deregulated MicroRNA Expression in Prostate Cancer", Cancer Research, 2008, vol. 68, No. 15, pp. 6162-6170.
Andriani et al., "Increased Sensitivity to Cisplatin in Non-Small Cell Lung Cancer Cell Line after FHIT Gene Trnasfer", Neoplasia, 2006, vol. 8, No. 1, pp. 9-17.
Aqeilan et al., "Targeted Deletion of WWOX Reveals a Tumor Suppressor Function", Proceedings of the National Academy of Sciences (PNAS), 2007, vol. 104, No. 10, pp. 3949-3954.
Arata et al., "Cdk2-dependent and -independent Pathways in E2F-mediated S Phase Induction", The Jouranal of Biological Chemistry, 2000, vol. 275, No. 9, pp. 6337-6345.
Asangani et al., "MicroRNA-21 (miR-21) post-transcriptionally downregulates tumor suppressor Pdcd4 and stimulates invasion, intravasation and metastasis in colorectal cancer", Oncogene, 2008, vol. 27, pp. 2128-2136.

(56) References Cited

OTHER PUBLICATIONS

Attwooll et al., "The E2F family: specific functions and overlapping interests", The EMBO Journal, 2004, vol. 23, pp. 4709-4716.
Baira et al., "Ultraconserved Elements: Genomics, Function and Disease", RNA Biology, 2008, vol. 5, No. 3, pp. 132-134.
Bakkus et al., "MicroRNA Expression Analysis in Multiple Myeloma Plasma Cells and Cell Lines by a Quantitative Real-Time PCR Approach", Blood, 2007, vol. 110, Abstract 2472.
Bandres et al., "Identification by Real-Time PCR of 13 Mature MicroRNAs Differentially Expressed in Colorectal Cancer and Non-Tumoral Tissues", Molecular Cancer, 2006, vol. 5, No. 29, pp. 1-10.
Bao et al., "Anti-Tumor Activity of a Novel Compound—CDF is Mediated by Regulating miR-21, miR-200, and PTEN in Pancreatic Caner", PLoS One, 2011, vol. 6, No. 3, pp. 1-12.
Barad et al., "MicroRNA Expression Detected by Oligonucleotide Microarrays: System Establishment and Expression Profiling in Human Tissues", Genome Research, 2004, vol. 14, pp. 2846-2494.
Bartel, "MicroRNAs: Genomics, Biogenesis, Mechanism, and Function", Cell, 2004, vol. 116, pp. 281-297.
Bartel, "MicroRNAs: Target Recognition and Regulatory Functions", Cell, 2009, vol. 136, pp. 215-233.
Basu et al., "MicroRNA-375 and MicroRNA-221:Potential Noncoding RNAs Associated with Antiproliferative Activity of Benzyl Isothiocyanate in Pancreatic Cancer", Genes & Cancer, 2011, vol. 2, No. 2, pp. 108-119.
Baudhuin et al., "Use of Microsatellite Instability and Immunohistochemistry Testing for the Identification of Individuals at Risk for Lynch Syndrome", Fam. Cancer, 2005, vol. 4, No. 3, pp. 255-265, Abstract Only.
Bednarek et al., "WWOX, the FRA16D Gene, Behaves as a Suppressor of Tumor Growth", Cancer Research, 2001, vol. 61, pp. 8068-8073.
Bejerano et al., "Computational Screening of Conserved Genomic DNA", Nature Methods, 2005, vol. 2, No. 7, pp. 535-545.
Bejerano et al., "Ultraconserved Elements in the Human Genome", Science, 2004, vol. 304, pp. 1321-1325, Electronic Supplement Data.
Bejerano et al., "Ultraconserved Elements in the Human Genome", Science, 2004, vol. 304, pp. 1321-1325.
Belinsky et al., "Inhibition of DNA Methylation and Histone Deacetylation Prevents Murine Lung Cancer", Cancer Research, 2003, vol. 63, pp. 7089-7093.
Bell, "Origins and Molecular Pathology of Ovarian Cancer", Modern Pathology, 2005, vol. 18, pp. S19-S32.
Bendoraite et al., "Regulation of miR-200 family microRNAs and ZEB transcription factors in ovarian cancer: evidence supporting a mesothelial-to-epithelial transition", Gynecologic Oncology, 2010, vol. 116, No. 1, pp. 117-125.
Bichi et al., "Human Chronic Lymphocytic Leukemia Modeled in Mouse by Targeted TCL1 Expression", Proceedings of the National Academy of Sciences (PNAS), 2002, vol. 99, No. 10, pp. 6955-6960.
Bloomston et al., "Identification of Molecular Markers Specific for Pancreatic Neuroendocrine Tumors by Genetic Profiling of Core Biopsies", Annals of Surgical Oncology, 2004, vol. 11, No. 4, pp. 413-419.
Bloomston et al., "MicroRNA Expression Patterns to Differentiate Pancreatic Adenocarcinoma from Normal Pancreas and Chronic Pancreatitis", Journal of the American Medical Association (JAMA), 2007, vol. 297, No. 17, pp. 1901-1908.
Blow et al., "Replication licensing—defining the proliferative state?", TRENDS in Cell Biology, 2002, vol. 12, No. 2, pp. 72-78.
Blum et al., "Clinical Response and miR-29b Predictive Significance in Older AML Patients Treated With a 10-Day Schedule of Decitabine", Proceedings of the National Academy of Sciences (PNAS), 2010, vol. 107, No. 16, pp. 7473-7478.
Boland et al., "Lynch Syndrome: Form, Function, Proteins, and Basketball", Gastroenterology, 2005, vol. 129, No. 2, pp. 751-755.
Bonci et al., "'Advanced' Generation Lentiviruses as Efficient Vectors for Cardiomyocyte Gene Transduction in vitro and in vivo", Gene Therapy, 2003, vol. 10, pp. 630-636.
Boominathan, "The Tumor Suppressors p53, p63, and p73 are Regulators of MicroRNA Processing Complex", PLoS One, 2010, vol. 5, No. 5, pp. 1-13.
Braun et al., "p53-Responsive MicroRNAs 192 and 215 are Capable of Inducing Cell Cycle Arrest", Cancer Research, 2008, vol. 68, No. 24, pp. 10094-10104.
Brueckner et al., "The Human let-7a-3 Locus Contains an Epigenetically Regulated MicroRNA Gene with Oncogenic Function", Cancer Research, 2007, vol. 67, No. 4, pp. 1419-1423.
Budhu et al., "Prediction of venous metastases, recurrence, and prognosis irhepatocellular carcinoma based on a unique immune response signature of the liver microenvironment", Cancer Cell, 2006, vol. 10, pp. 99-111.
Budhu et al., "A Unique Metastasis-Related MicroRNA Expression Signature is a Prognostic Indicator of Survival and Recurrence in Hepatocellular Carcinoma", Hepatology, 2007, vol. 46, No. 4, Supplement 1, Abstract # 1249, p. 791A.
Budhu et al., "Identification of Metastasis-Related MicroRNAs in Hepatocellular Carcinoma", Hepatology, 2008, vol. 47, No. 3, pp. 897-907.
Butz et al., "Down-Regulation of Wee1 Kinase by a Specific Subset of microRNA in Human Sporadic Pituitary Adenomas", Journal of Clinical Endocrinology and Metabolism, 2010, vol. 95, No. 10, pp. E181-E191.
Byori to Rinsho, Pathology and Clinical Medicine, 2006, vol. 24, No. 2, pp. 167-172, Japanese Document.
Caldas et al., "Sizing Up miRNAs as Cancer Genes", Nature Medicine, 2005, vol. 11, No. 7, pp. 712-714.
Calin et al., "A MicroRNA Signature Associated with Prognosis and Progression in Chronic Lymphocytic Leukemia", The New England Journal of Medicine, 2005, vol. 353, pp. 1793-1801.
Calin et al., "Chromosomal Rearrangements and microRNAs: A New Cancer Link with Clinical Implications", The Journal of Clinical Investigation, 2007, vol. 117, No. 8, pp. 2059-2066.
Calin et al., "Frequent Deletions and Down-Regulation of MicroRNA Genes miR15 and miR16 at 13q14 in Chronic Lymphocytic Leukemia", Proceedings of the National Academy of Sciences (PNAS), 2002, vol. 99, No. 24, pp. 15524-15529.
Calin et al., "Human microRNA Genes are Frequently Located at Fragile Sites and Genomic Regions Involved in Cancers", Proceedings of the National Academy of Sciences (PNAS), 2004, vol. 101, No. 9, pp. 2999-3004.
Calin et al., "MicroRNA Signatures in Human Cancers", Nature Reviews Cancer, 2006, vol. 6, pp. 857-866.
Calin et al., "MicroRNA Profiling Reveals Distinct Signatures in B Cell Chronic Lymphocytic Leukemias", Proceedings of the National Academy of Sciences (PNAS), 2004, vol. 101, No. 32, pp. 11755-11760.
Calin et al., "MiR-15a and MiR-16-1 Cluster Functions in Human Leukemia", Proceedings of the National Academy of Sciences (PNAS), 2008, vol. 105, No. 13, pp. 5166-5171.
Calin et al., "Ultraconserved Regions Encoding ncRNAs are Altered in Human Leukemias and Carcinomas", Cancer Cell, 2007, vol. 12, pp. 215-229.
Cannistra, "Cancer of the Ovary", The New England Journal of Medicine, 2004, vol. 351, pp. 2519-2529.
Castoldi et al., "A Sensitive Array for microRNA Expression Profiling (miChip) Based on Locked Nucleic Acids (LNA)", RNA, 2006, vol. 12, pp. 913-920.
Chambers et al., "Dissemination and Growth of Cancer Cells in Metastatic Sites", Nature Reviews Cancer, 2002, vol. 2, pp. 563-572.
Chan et al., "Concordant and Discordant Regulation of Target Genes by miR-31 and Its Isoforms", PLoS One, 2013, vol. 8, No. 3, pp. 1-11.
Chan et al., "MicroRNA-21 is an Antiapoptotic Factor in Human Glioblastoma Cells", Cancer Research, 2005, vol. 65, No. 14, pp. 6029-6033.
Chang et al., "Transactivation of miR-34a by p53 Broadly Influences Gene Expression and Promotes Apoptosis", Molecular Cell, 2007, vol. 26, pp. 745-752.
Chang et al., "Molecular Mechanisms Underlying WOX1 Activation During Apoptotic and Stress Responses", Biochemical Pharmacology, 2003, vol. 66, pp. 1347-1354.

(56) References Cited

OTHER PUBLICATIONS

Chang et al., "Widespread MicroRNA Repression by Myc Contributes to Tumorigenesis", Nature Genetics, 2008, vol. 40, No. 1, pp. 43-50.
Chen et al., "Downregulation of miR-221/222 sensitizes glioma cells to tempzolomide by regulating apoptosis independently of p53 status", Onocolgy Reports, 2012, vol. 27, pp. 854-860.
Chen et al., "Expanded Polyglutamine-Binding Peptoid as a Novel Therapeutic Agent for Treatment of Huntington's Disease", Chemistry & Biology, 2011, vol. 18, pp. 1113-1125.
Chen et al., "Real-time quantification of microRNAs by stem-loop RT-PCR", Nucleic Acids Research, 2005, vol. 33, No. 20, pp. 1-9.
Chen et al., "MicroRNAs as Regulators of Mammalian Hematopoiesis", Seminars in Immunology, 2005, vol. 17, pp. 155-165.
Cheng et al., "Antisense Inhibition of Human miRNAs and Indications for an Involvement of miRNA in Cell Growth and Apoptosis", Nucleic Acids Research, 2005, vol. 33, No. 4, pp. 1290-1297.
Chim et al., "Detection and Characterization of Placental MicroRNAs in Maternal Plasma", Clinical Chemistry, 2008, vol. 54, No. 3, pp. 482-490.
Cho, "OncomiRs: The Discovery and Progress of MicroRNAs in Cancers", Molecular Cancer, 2007, vol. 6, No. 60, pp. 1-7.
Chun-Zhi et al., "MicroRNA-221 and microRNA-222 regulate gastric carcinoma cell proliferation and radioresistance by targeting PTEN", BMC Cancer, 2010, vol. 10, No. 367, pp. 1-10.
Ciafre et al., "Extensive Modulation of a Set of microRNAs in Primary Glioblastoma", Biochemical and Biophysical Research Communications, 2005, vol. 334, pp. 1351-1358.
Cillo et al., "The critical issue of hepatocellular carcinoma prognostic classification: which is the best tool available?", Journal of Hepatology, 2004, vol. 40, pp. 124-131.
Cimmino et al., "miR-15 and miR-16 Induce Apoptosis by Targeting BCL2", Proceedings of the National Academy of Sciences (PNAS), 2005, vol. 102, No. 39, pp. 13944-13949.
Cimmino et al., Corrections to "miR-15 and miR-16 Induce Apoptosis by Targeting BCL2", Proceedings of the National Academy of Sciences (PNAS), 2006, vol. 103, No. 7, pp. 2464-2465.
Costinean et al., "Pre-B Cell Proliferation and Lymphoblastic Leukemia/ High-Grade Lymphoma in Eμ-miR155 Transgenic Mice", Proceedings of the National Academy of Sciences (PNAS), 2006, vol. 103, No. 18, pp. 7024-7029.
Cowgill et al., "The genetics of pancreatic cancer" The American Journal of Surgery, 2003, vol. 186, pp. 279-286.
Croce et al., "miRNAs, Cancer, and Stem Cell Division", Cell, 2005, pp. 6-7.
Croce et al., "Role of FHIT in Human Cancer", Journal of Clinical Oncology, 1999, vol. 17, No. 5, pp. 1618-1624.
Croce, "Causes and Consequences of MicroRNA Dysregulation in Cancer", Nature Reviews Genetics, 2009, vol. 10, pp. 704-714.
Croce, "Oncogenes and Cancer", The New England Journal of Medicine, 2008, vol. 358, pp. 502-511.
Cui et al., "MicroRNAs that Underlie Ovarian Cancer Development and Response to Chemotherapy", American Association for Cancer Research (AACR), 98th Annual Meeting, 2007, Abstract #4514.
Dahiya et al., "MicroRNA Expression and Identification of Putative miRNA Targets in Ovarian Cancer", PloS ONE, 2008, vol. 3, No. 6, pp. 1-11.
Dalmay et al., "MicroRNAs and the Hallmarks of Cancer", Oncogene, 2006, vol. 25, pp. 6170-6175.
Davies et al., "AZD6244 (ARRY-142886), a Potent Inhibitor of Mitogen-activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs", Molecular Cancer Therapeutics, 2007, vol. 6, No. 8, pp. 2209-2219.
Davies et al., "Insights into the Multistep Transformation of MGUS to Myeloma Using Microarray Expression Analysis", Blood, 2003, vol. 102, No. 13, pp. 4504-4511.

De Caestecker et al., "Role of Transforming Growth Factor-β Signaling in Cancer", Journal of the National Cancer Institute, 2000, vol. 92, No. 17, pp. 133-1402.
Debernardi et al., "MicroRNA miR-181a Correlates with Morphological Sub-Class of Acute Myeloid Leukemia and the Expression of its Target Genes in Global Genome-Wide Analysis", Leukemia, 2007, vol. 21, pp. 912-916.
Delott et al., "CDX2 Is a Useful Marker of Intestinal-Type Differentiation", Archives of Pathology & Laboratory Medicine, 2005, vol. 129, pp. 1100-1105.
Diccianni et al., "MicroRNA profiles of childhood T cell acute lymphoblastic leukemia", Proceedings of the American Association for Cancer Research (AACR), Meeting Abstracts, 2006, Abstract #124.
Dignam et al., "Accurate transcription initiation by RNA polymerase II in a soluble extract from isolated mammalian nuclei", Nucleic Acids Research, 1983, vol. 11, No. 5, pp. 1475-1489.
Dohner et al., "Genomic Aberrations and Survival in Chronic Lymphocytic Leukemia", The New England Journal of Medicine, 2000, vol. 343, No. 26, pp. 1910-1916.
Druck, "FHIT (Fragile Histidine Triad)", Atlas of Genetics and Cytogenetics in Oncology and Haematology, 2006, vol. 2, pp. 171-178.
Ehrich et al., "Quantitative High-Throughput Analysis of DNA Methylation Patterns by Base-Specific Cleavage and Mass Spectrometry", Proceedings of the National Academy of Sciences (PNAS), 2005, vol. 102, No. 44, pp. 15785-15790.
Eiriksdottir et al., "Mapping Loss of Heterozygosity at Chromosome 13q: Loss at 13q12-q13 is Associated with Breast Tumour Progression and Poor Prognosis", European Journal of Cancer, 1998, vol. 34, No. 13, pp. 2076-2081.
Eis et al., "Accumulation of miR-155 and BIC RNA in Human B Cell Lymphomas", Proceedings of the National Academy of Sciences (PNAS), 2005, vol. 102, No. 10, pp. 3627-3632.
Esquela-Kerscher et al., "Oncomirs—MicroRNAs with a Role in Cancer", Nature Reviews Cancer, 2006, vol. 6, pp. 259-269.
Eychene et al., "A New MAFia in Cancer", Nature Reviews Cancer, 2008, vol. 8, pp. 683-693.
Fabbri et al., "MicroRNAs", The Cancer Journal, 2008, vol. 14, No. 1, pp. 1-6.
Fabbri et al., "MicroRNA-29 Family Reverts Aberrant Methylation in Lung Cancer by Targeting DNA Methyltransferases 3A and 3B", Proceedings of the National Academy of Sciences (PNAS), 2007, vol. 104, No. 40, pp. 15805-15810.
Fabbri et al., "WWOX Gene Restoration Prevents Lung Cancer Growth In Vitro and In Vivo", Proceedings of the National Academy of Sciences (PNAS), 2005, vol. 102, No. 43, pp. 15611-15616.
Faguet, "Chronic Lymphocytic Leukemia: An Updated Review", Journal of Clinical Oncology, 1994, vol. 12, No. 9, pp. 1974-1990.
Faraoni et al., "miR-155 gene: A typical multifunctional microRNA", Biochimica et Biophysica Acta, 2009, vol. 1792, pp. 497-505.
Farazi et al., "MicroRNA Sequence and Expression Analysis in Breast Tumors by Deep Sequencing", Cancer Research, 2011, vol. 71, No. 13, pp. 4443-4453.
Felli et al., "MicroRNAs 221 and 222 Inhibit Normal Erythropoiesis and Erythroleukemic Cell Growth via Kit Receptor Down-Modulation", Proceedings of the National Academy of Sciences (PNAS), 2005, vol. 102, No. 50, pp. 18081-18086.
Feng et al., "Elevated Serum-Circulating RNA in Patients with Conventional Renal Cell Cancer", Anticancer Research, 2008, vol. 28, pp. 321-326.
Flavin et al., "MicroRNA Gene Expression Profiling in Human Ovarian and Primary Peritoneal Serous Carcinomas", United States and Canadian Academy of Pathology (USCAP), 96th Annual Meeting, 2007, Abstract #897.
Fong et al., "Muir-Torre-Like Syndrome in FHIT-Deficient Mice", Proceedings of the National Academy of Sciences (PNAS), 2000, vol. 97, No. 9, pp. 4742-4747.
Ford, "Using Synthetic miRNA Mimics for Diverting Cell Fate: A Possibility of miRNA-base Therapeutics?", Leukemia Research, 2006, vol. 30, pp. 511-513.

(56) References Cited

OTHER PUBLICATIONS

Fornari et al., "MiR-221 controls CDKN1C/p57 and CDKN1B/p27 expression in human hepatocellular carcinoma", Oncogene, 2008, vol. 27, pp. 5651-5661.
Fox et al., "A Single Amino Acid Substitution Makes ERK2 Susceptible to Pyridinyl Imidazole Inhibitors of p38 MAP Kinase", Protein Science, 1998, vol. 7, pp. 2249-2255.
Fujita et al., "miR-21 Gene Expression Triggered by AP-1 is Sustained Through a Double-Negative Feedback Mechanism", Journal of Molecular Biology, 2008, vol. 378, No. 3, pp. 492-504, Abstract Only.
Fulci et al., "Quantitative Technologies Establish a Novel MicroRNA Profile of Chronic Lymphocytic Leukemia", Blood, 2007, vol. 109, No. 11, pp. 4944-4951.
Gailiun, "Single microRNA Causes Cancer in Transgenic Mice", Research Communications, The Ohio State University, 2006, pp. 1-3.
Gang et al., "Expression of Programmed Cell Death 4 and Its Clinicopathological Significance in Human Pancreatic Cancer", Acta Academae Medicinae Sinicae, 2005, vol. 27, No. 5, p. 597, Abstract Only.
Garcea et al., "Molecular prognostic markers in pancreatic cancer: A systematic review", European Journal of Cancer, 2005, vol. 41, pp. 2213-2236.
Garofalo et al., "miR-221&222 Regulate TRAIL Resistance and Enhance Tumorigenicity through PTEN and TIMP3 Downregulation", Cancer Cell, 2009, vol. 16, pp. 498-509.
Garofalo et al., "MiR-221&222 enchance migration and invasiveness of NSCLC and hepatocarcinoma cells by targeting PTEN tumor suppressor", American Association for Cancer Research (AACR), Annual Meeting, 2009, Abstract #1319.
Garofalo et al., "miR221/222 in Cancer: Their Role in Tumor Progression and Response to Therapy", Current Molecular Medicine, 2012, vol. 12, No. 1, pp. 27-33.
Garofalo et al., "MicroRNA Signatures of TRAIL Resistance in Human Non-Small Cell Lung Cancer", Oncogene, 2008, vol. 27, pp. 3845-3855.
Garzon et al., "MicroRNA Expression and Function in Cancer", TRENDS in Molecular Medicine, 2006, vol. 12, No. 12, pp. 580-587.
Garzon et al., "MicroRNA signatures associated with cytogenetics and prognosis in acute myeloid leukemia", Blood, 2008, vol. 111, No. 6, pp. 3183-3189.
Garzon et al., "MicroRNA Signatures Associated with Cytogenetics and Outcome in Acute Myeloid Leukemia", American Society of Hematology (ASH), Annual Meeting Abstracts, Part 1, 2006, vol. 108, No. 11, p. 49a, Abstract #151.
Garzon et al., "MicroRNA Signatures Associated with Cytogenetics and Prognosis in Acute Myeloid Leukemia", Blood, 2006, vol. 108, Abstract #151.
Garzon et al., "MicroRNA Fingerprints During Human Megakaryocytopoiesis", Proceedings of the National Academy of Sciences (PNAS), 2006, vol. 103, No. 13, pp. 5078-5083.
Garzon, et al., "MicroRNA 29b Functions in Acute Myeloid Leukemia", Blood, 2009, vol. 114, No. 26, pp. 5331-5341.
Ghaneh et al., "Molecular prognostic markers in pancreatic cancer", Journal of Hepato-Biliary Pancreatic Surgery, 2002, vol. 9, pp. 1-11.
Ghoshal et al., "Up-regulation of oncogenic microRNAs and down-regulation of their tumor suppressor targets play a casual role in the initiation of hepatocarcinogenesis in mice fed choline-deficient and amino acid defined diet", American Association for Cancer Research (AACR), 99th Annual Meeting, 2008, Abstract #5033.
Gironella et al., "Tumor protein 53-induced nuclear protein 1 expression is repressed by miR-155, and its restoration inhibits pancreatic tumor development", Proceedings of The National Academy of Sciences (PNAS), 2007, vol. 104, No. 41, pp. 16170-16175.
Godlewski et al., "Targeting of the Bmi-1 Oncogene/Stem Cell Renewal Factor by MicroRNA-128 Inhibits Glioma Proliferation and Self-Renewal", Cancer Research, 2008, vol. 68, No. 22, pp. 9125-9130.

Goel et al., "A Novel Mechanism for Aspirin Mediated Growth Inhibition of Human Colon Cancer Cells", Clinical Cancer Research, 2003, vol. 9, pp. 383-390.
Goel et al., "Recent insights into the pathogenesis of colorectal cancer", Current Opinion in Gastroenterology, 2010, vol. 26, pp. 47-52.
Gottardo, et al., Micro-RNAs profiling in kidney and bladder cancers, Proc. Amer. Assoc. Cancer Res., 2005, vol. 46.
Gourley et al., "WWOX Gene Expression Abolishes Ovarian Cancer Tumorigenicity In vivo and Decreases Attachment to Fibronectin via Integrin α3", Cancer Research, 2009, vol. 69, No. 11, pp. 4835-4842.
Greenbaum et al., "Comparing Protein Abundance and mRNA Expression Levels on a Genomic Scale", Genome Biology, 2003, vol. 4, No. 9, pp. 117.1-117.8.
Gregory et al., "MicroRNA Biogenesis and Cancer", Cancer Research, 2005, vol. 65, No. 9, pp. 3509-3512.
Gregory et al., "The Microprocessor complex mediates the genesis of microRNAs", Nature, 2004, vol. 432, pp. 235-240.
Greither et al., "Elevated Expression of microRNAs 155, 203, 210 and 222 in Pancreatic Tumors is Assocaited with Poorer Survival", International Journal of Cancer, 2010, vol. 126, pp. 73-80.
Grier et al., "The Pathophysiology of HOX Genes and Their Role in Cancer", Journal of Pathology, 2005, vol. 205, pp. 154-171.
Griffiths-Jones et al., "miRBase: Tools for microRNA Genomics", Nucleic Acids Research, 2008, vol. 36, pp. D154-D158.
Griffiths-Jones et al., "miRBase: microRNA Sequences, Targets and Gene Nomenclature", Nucleic Acids Research, 2006, vol. 34, pp. D140-D144.
Griffiths-Jones, "The microRNA Registry", Nucleic Acids Research, 2004, vol. 32, pp. D109-D111.
Gu et al., "The t(4;11) Chromosome Translocation of Human Acute Leukemias Fuses the ALL-7 Gene, Related to *Drosophila trithorax*, to the AF-4 Gene", Cell, 1992, vol. 71, pp. 701-708.
Guenther et al., "Global and Hox-specific roles for the MLL1 methyltransferase", Proceedings of the National Academy of Sciences (PNAS), 2005, vol. 102, No. 24, pp. 8603-8608.
Guerrette et al., "Interactions of Human hMSH2 with hMSH3 and hMSH2 with hMSH6: Examination of Mutations Found in Hereditary Nonpolyposis Colorectal Cancer", Molecular and Cellular Biology, 1998, vol. 18, No. 11, pp. 6616-6623.
Guimaraes-Sternberg et al., "MicroRNA Modulation of Megakaryoblast Fate Involves Cholinergic Signaling", Leukemia Research, 2006, vol. 30, pp. 583-595.
Guweidhi et al. "Enhanced Expression of 14-3-3sigma in Pancreatic Cancer and its Role in Cell Cycle Regulation and Apoptosis", Carcinogenesis, 2004, vol. 25, No. 9, pp. 1575-1585.
Habbe et al., "MicroRNA miR-155 is a biomarker of early pancreatic neoplasia", Cancer Biology & Therapy, 2009, vol. 8, No. 4, pp. 340-346.
Han et al., "The Drosha-DGCR8 Complex in Primary microRNA Processing", Genes & Development, 2004, vol. 18, pp. 3016-3027.
Havelange et al., "MicroRNAs: New Players in Acute Myeloid Leukemia", British Journal of Cancer, 2009, vol. 101, pp. 743-748.
Hayashita et al., "A Polycistronic MicroRNA Cluster, miR-17-92, is Overexpressed in Human Lung Cancers and Enhances Cell Proliferation", Cancer Research, 2005, vol. 65, No. 21, pp. 9628-9632.
He et al., "A MicroRNA Polycistron as a Potential Human Oncogene", Nature, 2005, vol. 435, pp. 828-833.
He et al., "MicroRNA and Esophageal Carcinoma", Journal of Nanjing Medical University, 2007, vol. 21, No. 4, pp. 201-206.
He et al., "The Role of microRNA Genes in Papillary Thyroid Carcinoma," Proceedings of the National Academy of Sciences (PNAS), 2005, vol. 102, No. 52, pp. 19075-19080.
Herling et al., "TCL1 Shows a Regulated Expression Pattern in Chronic Lymphocytic Leukemia that Correlates with Molecular Subtypes and Proliferative State", Leukemia, 2006, vol. 20, pp. 280-285.
Hezel et al., "Genetics and biology of pancreatic ductal adenocarcinoma", Genes & Development, 2006, vol. 20, pp. 1218-1249.
Hiromura et al., "Identification of Nerve Growth Factor—Responsive Element of the TCL1 Promoter as a Novel Negative Regulatory Element", The Journal of Biological Chemistry, 2006, vol. 281, No. 38, pp. 27753-27764.

(56) References Cited

OTHER PUBLICATIONS

Hitchins, "Inheritance of Epigenetic Aberrations (Constitutional Epimutations) in Cancer Susceptibility", Advances In Genetics, 2010, vol. 70, pp. 202-243.

Hu et al., "A miR-200 microRNA cluster as prognostic marker in advanced ovarian cancer", Gynecologic Oncology, 2009, vol. 114, pp. 457-464.

Huang et al., "Evaluation of predictive value of CLIP, Okuda, TNM and JIS staging systems for hepatocellular carcinoma patients undergoing surgery", Journal of Gastroenterology and Hepatology, 2005, vol. 20, pp. 765-771.

Huang et al., "Microarray Analysis of microRNA Expression in Hepatocellular Carcinoma and Non-Tumorous Tissues Without Viral Hepatitis", Journal of Gastroenterology and Hepatology, 2008, vol. 23, pp. 87-94.

Hudlebusch et al., "Expression of HOXA Genes in Patients with Multiple Myeloma", Leukemia & Lymphoma, 2004, vol. 45, No. 6, pp. 1215-1217.

Hutvagner et al., "A microRNA in a Multiple Turnover RNAi Enzyme Complex", Science, 2002, vol. 297, pp. 2056-2060.

Iizuka et al., "Oligonucleotide microarray for prediction of early intrahepatic recurrence of hepatocellular carcinoma after curative resection", The Lancet, 2003, vol. 361, pp. 923-929.

Iliopoulos et al., "Fragile Genes as Biomarkers: Epigenetic Control of WWOX and FHIT in Lung, Breast and Bladder Cancer", Oncogene, 2005, vol. 24, pp. 1625-1633.

Iliopoulos et al., "Inhibition of Breast Cancer Cell Growth In vitro and In vivo: Effect of Restoration of WWOX Expression", Clinical Cancer Research, 2007, vol. 13, No. 1, pp. 268-274.

Iorio et al., "Causes and Consequences of microRNA Dysregulation", Cancer Journal, 2012, vol. 18, No. 3, pp. 215-222.

Iorio et al., "MicroRNA dysregulation in cancer: diagnostics, monitoring and therapeutics. A comprehensive review", EMBO Molecular Medicine, 2012, vol. 4, pp. 143-159.

Iorio et al., "MicroRNAs in Cancer: Small Molecules With a Hugh Impact", Journal of Clinical Oncology, 2009, vol. 27, No. 34, pp. 5848-5856.

Iorio et al., "MicroRNA Involvement in Human Cancer", Advance Access, 2012, pp. 1126-1133.

Iorio et al., "MicroRNA Gene Expression Deregulation in Human Breast Cancer", Cancer Research, 2005, vol. 65, No. 16, pp. 7065-7070.

Iorio et al., "MicroRNA Signatures in Human Ovarian Cancer", Cancer Research, 2007, vol. 67, No. 18, pp. 8699-8707.

Ishii et al., "Effect of Adenoviral Transduction of the Fragile Histidine Triad Gene into Esophageal Cancer Cells", Cancer Research, 2001, vol. 61, pp. 1578-1584.

Ivanovska et al., "MicroRNAs in the miR-106b Family Regulate p21/CDKN1A and Promote Cell Cycle Progression", Molecular and Cellular Biology, 2008, vol. 28, No. 7, pp. 2167-2174.

Izzotti et al., "Relationships of microRNA Expression in Mouse Lung with Age and Exposure to Cigarette Smoke and Light", The FASEB Journal, 2009, vol. 23, pp. 3243-3250.

Jacobs et al., "Prevalence Screening for Ovarian Cancer in Postmenopausal Women by CA 125 Measurement and Ultrasonography", BMJ, 1993, vol. 306, pp. 1030-1034.

Jacobs et al., "Progress and Challenges in Screening for Early Detection of Ovarian Cancer", Molecular & Cellular Proteomics, 2004, vol. 3, pp. 355-366.

Janis, "Ephrin-A Binding and EphA Receptor Expression Delineate the Matrix Compartment of the Striatum", The Journal of Neuroscience, 1999, vol. 19, No. 12, pp. 4962-4971.

Jannot et al., "Tumour-related mircoRNAs Functions in Caenorhabditis elegans", Oncogene, 2006, vol. 25, pp. 6197-6201.

Jansen et al., "Epidermal Expression of the Translation Inhibitor Programmed Cell Death 4 Suppresses Tumorigenesis", Cancer Research, 2005, vol. 65, No. 14, pp. 6034-6041.

Jazbutyte et al., "MicroNRA-21: From Cancer to Cardiovascular Disease", Current Drug Targets, 2010, vol. 11, No. 8, pp. 926-935, Abstract Only.

Jemal et al., "Cancer Statistics, 2007", CA: A Cancer Journal for Clinicians, 2007, vol. 57, No. 1, pp. 43-66.

Jemal et al., "Cancer Statistics, 2008", CA: A Cancer Journal for Clinicians, 2008, vol. 58, No. 2, pp. 71-96.

Ji et al., "Induction of Apoptosis and Inhibition of Tumorigenicity and Tumor Growth by Adenovirus Vector-mediated Fragile Histidine Triad (FHIT) Gene Overexpression", Cancer Research, 1999, vol. 59, pp. 3333-3339.

Ji et al., "MicroRNA Expression, Survival, and Response to Interferon in Liver Cancer", The New England Journal of Medicine, 2009, vol. 361, No. 15, pp. 1437-1447.

Ji et al., "New Kids on the Block: Diagnostic and Prognostic MicroRNAs in Hepatocellular Carcinoma", Cancer Biology & Therapy, 2009, vol. 8, No. 16, pp. 1-8.

Jiang et al., "MicroRNA-155 Functions as an OncomiR in Breast Cancer by Trageting the Suppressor of Cytokine Signaling 1 Gene", Cancer Research, 2010, vol. 70, pp. 3119-3127.

Jiang et al., "Association of MicroRNA Expression in Hepatocellular Carcinomas with Hepatitis Infection, Cirrhosis, and Patient Survival", Clinical Cancer Research, 2008, vol. 14, No. 2, pp. 419-427.

Jiang et al., "Real-Time Expression Profiling of MicroRNA Precursors in Human Cancer Cell Lines", Nucleic Acids Research, 2005, vol. 33, No. 17, pp. 5394-5403.

Johansson et al., "Hematologic malignancies with t(4;11)(q21;q23)—a cytogenetic, morphologic, immunophenotypic and clinical study of 183 cases", Leukemia, 1998, vol. 12, pp. 779-787.

John et al., "Human MicroRNA Targets", PLoS Biology, 2004, vol. 2, No. 11, pp. 1862-1879.

Johnson et al., "RAS is Regulated by the let-7 MicroRNA Family", Cell, 2005, vol. 120, pp. 635-647, Supplemental Data.

Johnson et al., "RAS is Regulated by the let-7 MicroRNA Family", Cell, 2005, vol. 120, pp. 635-647.

Johnson, "Treatment of Chronic Lymphocytic Leukemia by Total Body Irradiation Alone and Combined With Chemotherapy", International Journal of Radiation Oncology • Biology • Physics, 1979, vol. 5, No. 2, pp. 159-164.

Jover et al., "The efficacy of adjuvant chemotherapy with 5-fluorouracil in colorectal cancer depends on the mismatch repair status", European Journal of Cancer, 2009, vol. 45, pp. 365-373.

Kan et al., "Elevated Levels of Circulating microRNA-200 Family Members Correlate with Serous Epithelial Ovarian Cancer", BMC Cancer, 2012, vol. 12, No. 627, pp. 1-9.

Kane et al., "Methylation of the hMLH1 Promoter Correlates with Lack of Expression of hMLH1 in Sporadic Colon Tumors and Mismatch Repair-defective Human Tumor Cell Lines", Cancer Research, 1997, vol. 57, pp. 808-811.

Kawasaki et al., "MicroRNA-196 Inhibits HOXB8 Expression in Myeloid Differentiation of HL60 Cells", Nucleic Acids Symposium Series, 2004, vol. 48, pp. 211-212.

Kelly et al., "CT53518, A Novel Selective FLT3 Antagonist for the Treatment of Acute Myelogenous Leukemia (AML)", Cancer Cell, 2002, vol. 1, pp. 421-432.

Kim et al., "FHIT Protein Enhances Paclitaxel-Induced Apoptosis in Lung Cancer Cells", International Journal of Cancer, 2006, vol. 118, pp. 1692-1698.

Kim et al., "Processing of intronic microRNAs", The EMBO Journal, 2007, vol. 26, No. 3, pp. 775-783.

Kim et al., "Elevated mRNA Levels of DNA Methyltransferase-1 as an Independent Prognostic Factor in Primary Nonsmall Cell Lung Cancer", Cancer, 2006, vol. 107, No. 5, pp. 1042-1049.

Kim, "MicroRNA Biogenesis: Coordinated Cropping and Dicing", Nature Reviews Molecular Cell Biology, 2005, vol. 6, pp. 376-385.

Kluiver et al., "Lack of BIC and MicroRNA miR-155 Expression in Primary Cases of Burkitt Lymphoma", Genes, Chromosomes & Cancer, 2006, vol. 45, pp. 147-153.

Kluiver et al., "BIC and miR-155 are highly expressed in Hodgkin, primary mediastinal and diffuse large B cell lymphomas", Journal of Pathology, 2005, vol. 207, pp. 243-249.

Kotoula et al., "In Situ Detection of microRNAs 146b, 221 and 222 in Human Carcinoma Tissues Reveals Tumor-Type Specific Expression Patterns", American Association for Cancer Research (AACR), 98th Annual Meeting, 2007, Abstract #1780.

(56) References Cited

OTHER PUBLICATIONS

Koturbash et al., "Role of Epigenetic Effectors in Maintenance of the Long-Term Persistent Bystander Effect in Spleen In vivo", Carcinogenesis, 2007, vol. 28, No. 8, pp. 1831-1838.
Kozomara et al., "miRBase: Integrating MicroRNA Annotation and Deep-Sequencing Data", Nucleic Acids Research, 2011, vol. 39, pp. D152-D157.
Krek et al., "Combinatorial MicroRNA Target Predictions", Nature Genetics, 2005, vol. 37, No. 5, pp. 495-500.
Kudo et al., "Prognostic staging system for hepatocellular carcinoma (CLIP score): its value and limitations, and a proposal for a new staging system, the Japan Integrated Staging Score (JIS score)", Journal of Gastroenterol, 2003, vol. 38, pp. 207-215.
Kulshreshtha et al., "A MicroRNA Signature of Hypoxia", Molecular and Cellular Biology, 2007, vol. 27, No. 5, pp. 1859-1867.
Kuroki et al., "Genetic Alterations of The Tumor Suppressor Gene WWOX in Esophageal Squamous Cell Carcinoma", Cancer Research, 2002, vol. 62, pp. 2258-2260.
Kutay et al., "Downregulation of miR-122 in the Rodent and Human Hepatocellular Carcinomas", Journal of Cellular Biochemistry, 2006, vol. 99, pp. 671-678.
Lacombe et al., "Efficient knockdown of MMR proteins in human CRC cells using chained microRNA contructs", American Association for Cancer Research (AACR), 100th Annual Meeting, 2009, Abstract #1291.
Lagos-Quintana et al., "Identification of Tissue-Specific MicroRNAs from Mouse", Current Biology, 2002, vol. 12, pp. 735-739.
Lagos-Quintana et al., "Identification of Novel Genes Coding for Small Expressed RNAs", Science, 2001, vol. 294, pp. 853-858.
Lagos-Quintana et al., "New MicroRNAs From Mouse to Human", RNA, 2003, vol. 9, No. 2, pp. 175-179.
Lall et al., "A Genome-Wide Map of Conserved MicroRNA Targets in C. elegans", Current Biology, 2006, vol. 16, pp. 460-471.
Landgraf et al., "A Mammalian MicroRNA Expression Atlas Based on Small RNA Library Sequencing", Cell, 2007, vol. 129, pp. 1401-1414.
Landi et al., "Gene Expression Signature of Cigarette Smoking and Its Role in Lung Adenocarcinoma Development and Survival", PLoS ONE, 2008, vol. 3, No. 2, pp. 1-8.
Landthaler et al., "The Human DiGeorge Syndrome Critical Region Gene 8 and Its D. melanogaster Homolog are Required for miRNA Biogenesis", Current Biology, 2004, vol. 14, pp. 2162-2167.
Lanza et al., "mRNA/microRNA Gene Expression Profile in Microsatellite Unstable Colorectal Cancer", Molecular Cancer, 2007, vol. 6, No. 54, pp. 1-11.
Lau et al., "An Abundant Class of Tiny RNAs With Probable Regulatory Roles in Caenorhabditis elegans", Science, 2001, vol. 294, pp. 858-862.
Lawrie C. H. "MicroRNAs and Haematology: Small Molecules, Big Function", British Journal of Haematology, 2007, vol. 137, pp. 503-512.
Lawrie et al., "Detection of Elevated Levels of Tumour-Associated MicroRNAs in Serum of Patients with Diffuse Large B-Cell Lymphoma", British Journal of Haematology, 2008, vol. 141, pp. 672-675.
Lawrie, "MicroRNA, Expression in Lymphoma", Expert Opinion on Biological Therapy, 2007, vol. 7, No. 9, pp. 1363-1374.
Lecellier et al., "A Cellular MicroRNA mediates Antiviral Defense in Human Cells", Science, 2005, vol. 308, pp. 557-560.
Lee et al., "An Extensive Class of Small RNAs in Caenorhabditis Elegans", Science, 2001, vol. 294, pp. 862-864.
Lee et al., "MicroRNA maturation: stepwise processing and subcellular localization", The EMBO Journal, 2002, vol. 21, No. 17, pp. 4663-4670.
Lee et al., "MicroRNAs: Small but Potent Onogenes or Tumor Suppressors", Current Opinion in Investigational Drugs, 2006, vol. 7, No. 6, pp. 560-564.
Lee et al., "Expression Profiling Identifies MicroRNA Signature in Pancreatic Cancer", International Journal of Cancer, 2006, vol. 120, pp. 1046-1054.
Lee, "Expression and Function of MicroRNA in Human Cancel", Dissertation, The Ohio State University, 2008.
Levitt et al., "Dissociation of corticothalamic and thalamocortical axon targeting by an ephA7-mediated mechanism", International Journal of Developmental Neuroscience, 2006, vol. 24, p. 489 Abstract #S40.
Levy et al., "Staging of hepatocellular carcinoma: assessment of the CLIP, Okuda, and Child-Pugh staging systems in a cohort of 257 patients in Toronto", Gut, 2002, vol. 50, pp. 881-885.
Lewis et al., "Conserved Seed Pairing, Often Flanked by Adenosines, Indicates that Thousands of Human Genes are MicroRNA Targets", Cell, 2005, vol. 120, pp. 15-20.
Lewis et al., "Prediction of Mammalian MicroRNA Targets", Cell, 2003, vol. 115, pp. 787-798.
Li et al., "Bioinformatic Discovery of microRNA Precursors from Human ESTs and Introns", BMC Genomics, 2006, vol. 7, No. 164, pp. 1-11.
Li et al., "DNA mismatch repair (MMR)-dependent 5-fluorouracil cytotoxicity and the potential for new therapeutic targets", British Journal of Pharmacology, 2009, vol. 158, pp. 679-692.
Li et al., "Expression of serum miR-221 in human heptocellular carcinoma and its prognostic significance", Biochemical and Biophysical Research Communications, 2011, vol. 406, pp. 70-73.
Li et al., "Inhibition of PRL-3 Gene Expression in Gastric Cancer Cell Line SGC7901 via MicroRNA Suppressed Reduces Peritoneal Metastasis", Biochemical and Biophysical Research Communications, 2006, vol. 384, pp. 229-237.
Li et al., "miR-181a is an Intrinsic Modulator of T Cell Sensitivity and Selection", Cell, 2007, vol. 129, pp. 147-161.
Lin et al., "Alteration of DNA methyltransferases contributes to 5'CpG methylation and poor prognosis in lung cancer", Lung Cancer, 2007, vol. 55, pp. 205-213.
Lipp, "MicroRNAs Inform Cancer Research: Alterations in the Expression of miRNA Genes Contribute to Pathogenesis on Broad Basis", Genetic Engineering & Biotechnology News, 2009, pp. 38-39.
Liu et al., "Characterization of in vitro and in vivo hypomethylating effects of decitabine in acute myeloid leukemia by a rapid, specific and sensitive LC-MS/MS method", Nucleic Acids Research, 2007, vol. 35, No. 5, pp. 1-8.
Liu et al., "Increased Expression of MicroRNA-221 in Gastric Cancer and Its Clinical Significance", The Journal of International Medical Research, 2012, vol. 40, pp. 467-474.
Liu et al., "Tissue Inhibitor of Metalloroteinase-1 Protects Human Breast Epithelial Cells From Extrinsic Cell Death: A Potential Oncogenic Activity of Tissue Inhibitor of Metalloproteninase-1", Cancer Research, vol. 65, No. 3, pp. 898-906.
Liu et al., "An Oligonucleotide Microchip for Genome-Wide MicroRNA Profiling in Human and Mouse Tissues", Proceedings of the National Academy of Sciences (PNAS), 2004, vol. 101, No. 26, pp. 9740-9744.
Loffler et al., "Interleukin-6-Dependent Survival of Multiple Myeloma Cells Involves the Stat3-Mediated Induction of MicroRNA-21 Through a Highly Conserved Enhancer", Blood, 2007, vol. 110, No. 4, pp. 1330-1333.
Lu et al., "MicroRNA Expression Profiles Classify Human Cancers", Nature, 2005, vol. 435, pp. 834-838.
Lujambio et al., "A MicroRNA DNA Methylation Signature for Human Cancer Metastasis", Proceedings of the National Academy of Sciences (PNAS), 2008, vol. 105, No. 36, pp. 13556-13561.
Ma et al., "MicroRNAs in NF-kB signaling", Journal of Molecular Cell Biology, 2011, vol. 3, pp. 159-166.
Ma et al., "Expression of Programmed Cell Death 4 and Its Clinicopathological Significance in Human Pancreatic Cancer", Medline, 2005, pp. 597-600, Abstract Only.
Mack, "MicroRNA Gets Down to Business", Nature Biotechnology, 2007, vol. 25, No. 6, pp. 631-638.
Maiseyeu et al., "Gadolinium Containing Phosphatidylserine Liposomes for Molecular Imaging of Atherosclerosis", Journal of Lipid Research, 2010, pp. 1-9.
Marchetti et al., "EGFR Mutations in Non-Small-Cell Lung Cancer: Analysis of a Large Series of Cases and Development of a Rapid and Sensitive Method for Diagnostic Screening with Potential Implica-

(56) References Cited

OTHER PUBLICATIONS tions on Pharmacologic Treatment", Journal of Clinical Oncology, 2005, vol. 23, No. 4, pp. 857-865.
Marcucci et al., "MicroRNA Expression in Cytogenetically Normal Acute Myeloid Leukemia", The New England Journal of Medicince, 2008, vol. 358, No. 18, pp. 1919-1928.
Marsit et al., "MicroRNA Responses to Cellular Stress", Cancer Research, 2006, vol. 66, No. 22, pp. 10843-10848.
Martin et al., "MicroRNA-155 Regulates Human Angiotensin II Type 1 Receptor Expression in Fibroblasts", The Journal of Biological Chemistry, 2006, vol. 281, No. 27, pp. 18277-18284.
Mascellani et al., "Using miRNA Expression Data for the Study of Human Cancer", Minerva Biotec, 2008, vol. 20, No. 1, pp. 23-30.
Masri et al., "MicroRNA Expression Analysis in Multiple Myeloma", Blood, 2005, vol. 106, Abstract #1554.
Mattie et al., "Optimized High-Throughput MicroRNA Expression Profiling Provides Novel Biomarker Assessment of Clinical Prostate and Breast Cancer Biopsies", Molecular Cancer, 2006, vol. 5, No. 24, pp. 1-14.
Mazurek et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, 2007, vol. 282, No. 29, pp. 21337-21348.
McManus, "MicroRNAs and Cancer", Seminars in Cancer Biology, 2003, vol. 13, pp. 253-258.
Medina et al., "MicroRNAs 221 and 222 Bypass Quiescence and Compromise Cell Survival", Cancer Research, 2008, vol. 68, No. 8, pp. 2773-2780.
Medina et al., "OncomiR Addiction in an In Vivo Model of microRNA-21-Induced Pre-B-Cell Lymphoma", Nature, 2010, vol. 467, pp. 86-91.
Medina et al., "OncomiR Addicton in an in vivo Model of MicroRNA-21-Induced Pre-B-Cell Lymphoma", Nature, 2010, vol. 467, p. 1-22, Supplementary Information.
Megraw et al., "miRGen: A Database for the Study of Animal MicroRNA Genomic Organization and Function", Nucleic Acids Research, 2007, vol. 35, pp. D149-D155.
Mendell, "miRiad Roles for the miR-17-92 Cluster in Development and Disease", Cell, 2008, vol. 133, pp. 217-222.
Meng et al., "MicroRNA-21 Regulates Expression of the PTEN Tumor Suppressor Gene in Human Hepatocellular Cancer", Gastroenterology, 2007, vol. 133, pp. 647-658.
Meng et al., "Involvement of Human Micro-RNA in Growth and Response to Chemotherapy in Human Cholangiocarcinoma Cell Lines", Gastroenterology, 2006, vol. 130, pp. 2113-2129.
Mercatelli et al., "The Inhibition of the Highly Expressed Mir-221 and Mir-222 Impairs the Growth of Prostate Carcinoma Xenografts in Mice", PLoS ONE, 2008, vol. 3, No. 12, pp. 1-10.
Metzler et al., "High Expression of Precursor MicroRNA-155/BIC RNA in Children with Burkitt Lymphoma", Genes, Chromosomes & Cancer, 2004, vol. 39, pp. 167-169.
Mi et al., "MicroRNA Expression Signatures Accurately Discriminate Acute Lymphoblastic Leukemia from Acute Myeloid Leukemia", Proceedings of the National Academy of Sciences (PNAS), 2007, vol. 104, No. 50, pp. 19971-19976.
Michael et al., "Reduced Accumulation of Specific MicroRNAs in Colorectal Neoplasia", Molecular Cancer Research, 2003, vol. 1, pp. 882-891.
Miller et al., "Concurrent Chronic Lymphocytic Leukemia Cutis and Acute Myelogenous Leukemia Cutis in a Patient with Untreated CLL", The American Journal of Dermatopathology, 2001, vol. 23, No. 4, pp. 334-340.
Mishra et al., "Cancer Biomarkers: Are We Ready for the Prime Time?", Cancers, 2010, vol. 2, pp. 190-208.
Mitchell et al., "Circulating microRNAs as Stable Blood-Based Markers for Cancer Detection", Proceedings of the National Academy of Sciences (PNAS), 2008, vol. 105, No. 30, pp. 10513-10518.
Mitrovic et al., "Cancer Gene Therapy", Archive of Oncology, 2005, vol. 13, No. 1, pp. 23-26.

Mizusawa et al., "Differentiation phenotypes of pancreatic islet β- and α-cells are closely related with homeotic genes and a group of differentially expressed genes", Gene, 2004, vol. 331, pp. 53-63.
Mountzios et al., "Mechanisms of Disease: Signal Transduction in Lung Carcinogenesis—A Comparison of Smokers and Never-Smokers", Nature Clinical Practice Oncology, 2008, vol. 5, No. 10, pp. 610-618.
Mueller et al., "Comprehensive Molecular Analysis of Mismatch Repair Gene Defects in Suspected Lynch Syndrome (Hereditary Nonpoluposis Colorectal Cancer) Cases", Cancer Research, 2009, vol. 69, No. 17, pp. 7053-7061.
Murakami et al., "Comprehensive Analysis of microRNA Expression Patterns in Hepatocellular Carcinoma and Non-Tumorous Tissues", Oncogene, 2006, vol. 25, pp. 2537-2545.
Naegeli et al., "Novel Mechanisms of Ovarian Cancer Growth Inhibition, via MicroRNA Downregulation and Oxidative Damage, by a Ratioanlly Designed Histone Deacetylase Inhibitor", American Association for Cancer Research (AACR), 98th Annual Meeting, 2007, Abstract #2475.
Nakajima et al., "Non-Coding MicroRNAs hsa-let-7g and hsa-miR-181b are Associated with Chemoresponse to S-1 in Colon Cancer", Cancer Genomics & Proteomics, 2006, vol. 3, pp. 317-324.
Nakamura et al., "All-1 Is a Histone Methyltransferase that Assembles a Supercomplex of Proteins Involved in Transcriptional Regulation", Molecular Cell, 2002, vol. 10, pp. 1119-1128.
Nakanishi et al., "ALL1 Fusion Proteins Induce Deregulation of EphA7 and ERK Phosphorylation in Human Acute Leukemias", Proceedings of the National Academy of Sciences (PNAS), 2007, vol. 104, No. 36, pp. 14442-14447.
Nam et al., "MicroRNA Expression Profiles in Serous Ovarian Carcinoma", Clinical Cancer Research, 2008, vol. 14, No. 9, pp. 2690-2695.
Nana-Sinkam et al., "Clinical Applications for microRNAs in Cancer", Nature, 2013, vol. 93, No. 1, pp. 98-104.
Nazarov et al., "Interplay of microRNAs, transcription factors and target genes: linking dynamic expression changes to function", Nucleic Acids Research, 2013, vol. 41, No. 5, pp. 2817-2831.
Negrini et al., "MicroRNAs in Human Cancer: From Research to Therapy", Journal of Cell Science, 2007, vol. 120, No. 11, pp. 1833-1840.
Nicoloso et al., "MicroRNAs—The Micro Steering Wheel of Tumour Metastases", Nature Reviews Cancer, 2009, vol. 9, pp. 293-302.
Nippon, Journal of the Japanese Society, 1993, vol. 82, pp. 1053-1057.
Nurden, "Qualitative Disorders of Platelets and Megakaryocytes", Journal of Thrombosis and Haemostasis, 2005, vol. 3, pp. 1773-1782.
O'Connell et al., "Inositol Phosphatase SHIP1 is a Primary Target of miR-155", Proceedings of the National Academy of Sciences (PNAS), 2009, vol. 106, No. 17, pp. 7113-7118.
O'Donnell et al., "c-Myc-regulated microRNAs modulate E2F1 expression", Nature, 2005, vol. 435, pp. 839-843.
Okada et al., "MicroRNAs in Immune Regulation—Opportunities for Cancer Immunotherapy", The International Journal of Biochemistry & Cell Biology, 2010, vol. 42, pp. 1256-1261.
Okuda et al., "Natural History of Hepatocellular Carcinoma and Prognosis in Relation to Treatment", Cancer, 1985, vol. 56, No. 4, pp. 918-928.
Olivier et al., "CA125 and Transvaginal Ultrasound Monitoring in High-Risk Women Cannot Prevent the Diagnosis of Advanced Ovarian Cancer", Gynecologic Oncology, 2006, vol. 100, pp. 20-26.
Palamarchuk et al., "Akt Phosphorylates Tal1 Oncoprotein and Inhibits Its Repressor Activity", Cancer Research, 2005, vol. 65, No. 11, pp. 4515-4519.
Pallante et al., "MicroRNA deregulation in human thyroid papillary carcinomas", Endocrine-Related Cancer, 2006, vol. 13, pp. 497-508.
Pan et al., "Non-Steroidal Anti-Inflammatory Drugs Suppress the ERK Signaling Pathway via Block of Ras/c-Raf Interaction and Activation of MAP Kinase Phosphatases", Cellular Signaling, 2008, vol. 20, pp. 1134-1141.
Panarelli et al., "MicroRNA Expression Aids the Preoperative Diagnosis of Pancreatic Ductal Adenocarcinoma", Pancreas, 2012, vol. 41, No. 5, pp. 685-690.

(56) References Cited

OTHER PUBLICATIONS

Papageorgiou et al., "Interferon-α Induces TRAIL Expression and Cell Death Via an IRF-1-Dependent Mechanism in Human Bladder Cancer Cells", Cancer Biology & Therapy, 2007, vol. 6, No. 6, pp. 872-879.
Park et al., "Antisense inhibition of microRNA-21 or-221 arrests cell cycle, induces apoptosis, and sensitizes the effects of gemcitabine in pancreatic adenocarcinoma", Pancreas, 2009, vol. 38, No. 7, Abstract Only.
Park et al., "miR-221 Silencing Blocks Hepatocellular Carcinoma and Promotes Survival", Cancer Research, 2011, vol. 71, No. 24, pp. 7608-7616.
Parkin, et al., "Global Cancer Statistics, 2002", CA: A Cancer Journal for Clinicians, 2005, vol. 55, pp. 74-108.
Partha et al., "Early Detection of Ovarian Cancer," Biomarkers in Medicine, 2008, vol. 2, No. 3, pp. 291-303.
Pasche et al., "TβR-I(6A) is a Candidate Tumor Susceptibility Allele", Cancer Research, 1999, vol. 59, pp. 5678-5682.
Pasquinelli et al., "MicroRNAs: a developing story", Current Opinion in Genetics & Development, 2005, vol. 15, pp. 200-205.
Pathi et al., "GT-094, a NO-NSAID, Inhibits Colon Cancer Cell Growth by Activation of a Reaction Oxygen Species—MircoRNA-27a: ZBTB10-Specificity Protein Pathway", Molecular Cancer Research, 2011, vol. 9, pp. 195-202.
Pawelczyk et al., "Expression in *Escherichia coli* and Simple Purification of Human Fhit Protein", Protein Expression and Purification, 2000, vol. 18, No. 3, pp. 320-326.
Pedersen et al., "Onco-miR-155 targets SHIP1 to promote TNFα-dependent growth of B cell lymphomas", EMBO Molecular Medicine, 2009, vol. 1, pp. 288-295.
Pedersen et al., "Interferon Modulation of Cellular MicroRNAs as an Antiviral Mechanism", Nature, 2007, vol. 449, pp. 919-922.
Pekarsky et al., "Animal Models for Chronic Lymphocytic Leumekia", Journal of Cellular Biochemistry, 2007, vol. 100, pp. 1109-1118.
Pekarsky et al., "Tcl1 Functions as a Transcriptional Regulator and is Directly Involved in the Pathogenesis of CLL", Proceedings of the National Academy of Sciences (PNAS), 2008, vol. 105, No. 50, pp. 19643-19648.
Pekarsky et al., "Tcl1 Expression in Chronic Lymphocytic Leukemia is Regulated by miR-29 and miR-181", Cancer Research, 2006, vol. 66, No. 24, pp. 11590-11593.
Pekarsky et al., "Tcl1 Enhances Akt Kinase Activity and Mediates Its Nuclear Translocation", Proceedings of the National Academy of Sciences (PNAS), 2000, vol. 97, No. 7, pp. 3028-3033.
Petrocca et al., "MicroRNAs Deregulation in Gastric Cancer", American Association for Cancer Research (AACR), Meeting Abstracts, 2006, Abstract #5690.
Petrocca et al., "E2F1-Regulated MicroRNAs Impair TGFβ-Dependent Cell-Cycle Arrest and Apoptosis in Gastric Cancer", Cancer Cell, 2008, vol. 13, pp. 272-286.
Pichiorri et al., "Downregulation of p53-Inducible microRNAs 192, 194, and 215 Impairs the p53/MDM2 Autoregulatory Loop in Multiple Myeloma Development", Cancer Cell, 2010, vol. 18, pp. 367-381.
Pichiorri et al., "MicroRNA Signatures in Multiple Myeloma", American Association for Cancer Research (AACR), 99th Annual Meeting, 2008, Abstract #5047.
Pichiorri et al., "MicroRNAs Regulate Critical Genes Associated with Multiple Myeloma Pathogenesis", Proceedings of the National Academy of Sciences (PNAS), 2008, vol. 105, No. 35, pp. 12885-12890.
Pineau et al., "miR-221 Overexpression Contributes to Liver Tumorigenesis", Proceedings of the National Academy of Sciences (PNAS), 2010, vol. 107, No. 1, pp. 264-269.
Poliseno et al., "MicroRNAs modulate the angiogenic properties of HUVECs", Blood, 2006, vol. 108, No. 9, pp. 3068-3071.
Porkka et al., "MicroRNA Expression Profiling in Prostate Cancer", Cancer Research, 2007, vol. 67, No. 13, pp. 6130-6135.
Pouponnot et al., "Cell Context Reveals a Dual Role for Maf in Oncogenesis", Oncogene, 2006, vol. 25, pp. 1299-1310.
Poy et al., "A pancreatic islet-specific microRNA regulates insulin secretion", Nature, 2004, vol. 432, pp. 226-230.
Prueitt et al., "Expression of MicroRNAs and Protein-Coding Genes Associated with Perineural Invasion in Prostate Cancer", The Prostate, 2008, vol. 68, pp. 1152-1164.
Pruitt et al., "NCBI Reference Sequence (RefSeq): A Curated Non-Redundant Sequence Database of Genomes, Transcripts and Proteins", Nucleic Acids Research, 2005, vol. 33, pp. D501-D504.
Pu et al., "Circulating miR-221 directly amplified from plasma is a potential diagnostic and prognostic marker of colorectal cancer and is correlated with p53 expression", Journal of Gastroenterology and Hepatology, 2010, vol. 25, pp. 1674-1680.
Qin et al., "A Role for the WWOX Gene in Prostate Cancer", Cancer Research, 2006, vol. 66, No. 13, pp. 6477-6481.
Ramkissoon et al., "Hematopoietic-Specific microRNA Expression in Human Cells", Leukemia Research, 2006, vol. 30, pp. 643-647.
Ren et al., "Co-delivery of as-miR-21 and 5-FU by Poly (amidoamine) Dendrimer Attenuates Human Glioma Cell Growth in Vitro", Journal of Biomaterials Science, 2010, vol. 21, pp. 303-314.
Resnick et al., "The detection of differentially expressed microRNAs from the serum of ovarian cancer patients using a novel real-time PCR platform", Gynecologic Oncology, 2009, vol. 112, pp. 55-59.
Ribas et al., "The Transcriptional Regulation of miR-21, its Multiple Transcripts, and Their Implication in Prostate Cancer", Cell Cycle, 2010, vol. 9, No. 5, pp. 923-929.
Rockerfeller University, "For Different Species, Different Functions for Embryonic MircoRNAs", Science Daily, 2009, Retrieved Nov. 8, 2013 from Web address: http://www.sciencedaily.com/release/2009/05/090522171001.htm.
Roldo et al., "MicroRNA Expression Abnormalities in Pancreatic Endocrine and Acinar Tumors Are Associated With Distinctive Pathologic Feature and Clinical Behavior", Journal of Clinical Oncology, 2006, vol. 24, No. 29, pp. 4677-4684.
Rosa et al., "The miR-430/427/302 Family Controls Mesendodermal Fate Specification via Species-Specific Target Selection", Developmental Cell, 2009, vol. 16, pp. 517-527.
Rossi et al., "MicroRNA Fingerprinting of CLL Patients with Chromosome 17p Deletion Identify a miR-21 Score that Stratifies Early Survival", Blood, 2010, vol. 116, No. 6, pp. 945-952.
Rossi, et al., "Modification of MiR gene expression pattern in human colon cancer cells following exposure to 5-fluorouracil in vitro", Pharmacological Research, 2007, vol. 56, No. 3, pp. 248-253.
Rozovskaia et al., "Expression Profiles of Acute Lymphoblastic and Myeloblastic Leukemias with ALL-1 Rearrangements", Proceedings of the National Academy of Sciences (PNAS), 2003, vol. 100, No. 13, pp. 7853-7858.
Ryu et al., "Aberrant MicroRNA-155 Expression is an Early Event in the Multistep Progression of Pancreatic Adenocarcinoma", Pancreatology, 2010, vol. 10, pp. 66-73.
Sah et al., "Translation Inhibitors Sensitize Prostate Cancer Cells to Apoptosis Induced by Tumor Necrosis Factor-related Apoptosis-inducing Ligand (TRAIL) by Activating c-Jun N-terminal Kinase", The Journal of Biological Chemistry, 2003, vol. 278, pp. 20593-20602.
Saini et al., "Annotation of Mammalian Primary microRNAs", BioMed Central Genomics, 2008, vol. 9, No. 564, pp. 1-19.
Saito et al., "Specific Activation of microRNA-127 with Downregulation of the Proto-Oncogene BCL6 by Chromatin-Modifying Drugs in Human Cancer Cells", Cancer Cell, 2006, vol. 9, pp. 435-443.
Salovaara et al., "Population-Based Molecular Detection of Hereditary Nonpolyposis Colorectal Cancer", Journal of Clinical Oncology, 2000, vol. 18, No. 11, pp. 2193-2200.
Santanam et al., "Chronic Lymphocytic Leukemia Modeled in Mouse by Targeted miR-29 Expression", Proceedings of the National Academy of Sciences (PNAS), 2010, vol. 107, No. 27, pp. 12210-12215.
Sarver et al., "Human Colon Cancer Profiles Show Differential microRNA Expression Depending on Mismatch Repair Status and are Characteristic of Undifferentiated Proliferative States", BioMed Central Cancer, 2009, vol. 9, No. 401, pp. 1-15.

(56) References Cited

OTHER PUBLICATIONS

Sasaki, et al., "Coordinated Expression of ncRNAs and HOX mRNAs in the Human HOXA Locus", Biochemical and Biophysical Research Communications, 2007, vol. 357, pp. 724-730.
Schagen et al., "Genetic Targeting of Adenovirus Vectors Using a Reovirus σ1-Based Attachment Protein", Molecular Therapy, 2006, vol. 13, No. 5, pp. 997-1005.
Schetter et al., "Association of Inflammation-Related and microRNA Gene Expression with Cancer Specific Mortality of Colon Adenocarcinoma", Clinical Cancer Research, 2009, vol. 15, No. 18, pp. 5878-5887.
Schetter et al., "MicroRNA Expression Profiles Associated With Prognosis and Therapeutic Outcome in Colon Adenocarcinoma", Journal of the American Medical Association (JAMA,) 2008, vol. 299, No. 4, pp. 425-436.
Schmittgen et al., "A High-Throughput Method to Monitor the Expression of MicroRNA Precursors", Nucleic Acids Research, 2004, vol. 32, No. 4, pp. 1-10.
Schrump et al.,"Targeting the Epigenome for the Treatment and Prevention of Lung Cancer", Seminars in Oncology, 2005, vol. 32, pp. 488-502.
Seike et al., "MiR-21 is an EGFR-Regulated Anti-Apoptotic Factor in Lung Cancer in Never-Smokers", Proceedings of the National Academy of Sciences (PNAS), 2009, vol. 106, No. 29, pp. 12085-12090.
Seike et al., "MiR-21 is an EGFR-Regulated Anti-Apoptotic Factor in Lung Cancer in Never-Smokers", Proceedings of the National Academy of Sciences (PNAS), 2009, vol. 106, No. 29, pp. 12085-12090, Supporting Information.
Seike, "MicroRNA Expression Profiles in Lung Cancer Cooperated with Drug Sensitivity to EGFR Tyrosine Kinase Inhibitor", Journal of Nippon Medical School, 2009, vol. 76, No. 5, pp. 275-276.
Selvendiran et al., "NCX-4016 a Nitro-derivative of Aspirin, Inhibits EGFR and STAT3 signaling and modulates bcl-2 Proteins in Cisplatin Resistant Human Ovarian Cancer Cells and Xenografts", Cell Cycle, 2008, vol. 7, No. 1, pp. 81-88.
Seth, "Vector-Mediated Cancer Gene Therapy", Cancer Biology & Therapy, 2005, vol. 4, No. 5, pp. 512-517.
Sevinsky et al., "Extracellular Signal-Regulated Kinase Induces the Megakaryocyte GPIIb/CD41 Gene Through MafB/Kreisler", Molecular and Cellular Biology, 2004, vol. 24, No. 10, pp. 4534-4545.
Sharma et al., "Development of Inhalational Agents for Oncologic Use", Journal of Clinical Oncology, 2001, vol. 19, No. 6, pp. 1839-1847, Abstract Only.
Shen et al., "Novel genetic variants in miR-191 gene and familial ovarian cancer", BMC Cancer, 2010, vol. 10, No. 47, pp. 1-8.
Shen et al., "A Novel Polymorphism in Human Cytosine DNA-Methyltransferase-3B Promoter is Associated with an Increased Risk of Lung Cancer", Cancer Research, 2002, vol. 62, pp. 4992-4995.
Shih et al., "Exosomal microRNAs Step into the Biomarker Arena", Gynecologic Oncology, 2008, vol. 110, pp. 1-2.
Skalsky et al., "Kaposi's Sarcoma-Associated Herpesvirus Encodes an Ortholog of miR-155", Journal of Virology, 2007, vol. 81, No. 23, pp. 12836-12845.
Slaby et al., "Altered Expression of miR-21, miR-31, miR-143 and miR-145 is Related to Clinicopathologic Features of Colorectal Cancer", Oncology, 2007, vol. 72, pp. 397-402.
Slack, "Big Roles for Small RNAs", Nature, 2010, vol. 463, p. 616.
Sonoki et al., "Insertion of microRNA-125b-1, A Human Homologue of lin-4, into a Rearranged Immunoglobulin Heavy Chain Gene Locus in a Patient with Precursor B-cell Acute Lymphoblastic Leukemia", Leukemia, 2005, vol. 19, pp. 2009-2010.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Stenvang et al., "The utility of LNA in microRNA-based cancer diagnostics and therapeutics", Seminars in Cancer Biology, 2008, vol. 18, pp. 89-102.
Suarez-Saiz et al., "MicroRNA Expression Profiling in Acute Myelogenous Leukemia", Canada Blood, 2004, p. 320A, Abstract #1131.
Sugito et al., "RNASEN regulates Cell Proliferation and Affects Survival in Esophageal Cancer Patients", Clinical Cancer Research, 2006, vol. 12, No. 24, pp. 7322-7328.
Suh et al., "Human embryonic stem cells express a unique set of microRNAs", Developmental Biology, 2004, vol. 270, pp. 488-498.
Sun et al., "Analysis of microRNA Expression Patterns in Hepatocellular Carcinoma and Non-Tumorous Tissues by Liquichip Assay", Chinese Journal of Experimental Surgery, 2006, vol. 23, No. 8, p. 945-947.
Sun et al., "MicroRNA-221 inhibits CDKN1C/p57 expression in human colorectal carcinoma", Acta Pharmacologica Sinica, 2011, vol. 32, pp. 375-384.
Suzuki et al., "RNA Interference-Mediated Knockdown of DNA Methyltransferase 1 Leads to Promoter Demethylation and Gene Re-Expression in Human Lung and Breast Cancer Cells", Cancer Research, 2004, vol. 64, pp. 3137-3143.
Szymanski et al., "A new frontier for molecular medicine: Noncoding RNAs", Biochimica et Biophysica Acta, 2005, vol. 1756, pp. 65-75.
Taccioli et al., "Ucbase & miRfunc: A Database of Ultraconserved Sequences and MicroRNA Function", Nucleic Acids Research, 2009, vol. 37, pp. D41-D48.
Takamizawa et al., "Reduced Expression of the let-7 MicroRNAs in Human Lung Cancers in Association with Shortened Postoperative Survival", Cancer Research, 2004, vol. 64, pp. 3753-3756.
Tam,"The Emergent Role of MicroRNAs in Molecular Diagnostics of Cancer", Journal of Molecular Diagnostics, 2008, vol. 10, No. 5, pp. 411-414.
Tang et al., "A Simple Array Platform for microRNA Analysis and its Application in Mouse Tissues", RNA Journal, 2007, vol. 13, pp. 1-20.
Tanner et al., "BAALC, the human member of a novel mammalian neuroectoderm gene lineage, is implicated in hematopoiesis and acute leukemia", Proceedings of the National Academy of Sciences (PNAS), 2001, vol. 98, No. 24, pp. 13901-13906.
Tanzer etal., "Molecular Evolution of a MicroRNA Cluster", Journal of Molecular Biology, 2004, vol. 339, pp. 327-335.
Tatsuya et al., "Oncogenic All1 fusion proteins target Drosha-mediated microRNA processing", Proceedings of the National Academy of Sciences (PNAS), 2007, vol. 104, No. 26, pp. 10980-10985.
Tavazoie et al., "Endogenous Human mircoRNAs that Suppress Breast Cancer Metastasis", Nature, 2008, vol. 451, pp. 147-152.
Taylor et al., "MicroRNA Signatures of Tumor-Derived Exosomes as Diagnostic Biomarkers of Ovarian Cancer", Gynecologic Oncology, 2008, vol. 110, pp. 13-21.
Teachey et al., "Mammalian target of rapamycin inhibitors and their potential role in therapy in leukemia and other haematogical malignancies", British Journal of Haematology, 2009, vol. 145, pp. 569-580.
Teng et al., "Shhh! Silencing by microRNA-155," Philosophical Transactions of The Royal Society B, 2009, vol. 364, pp. 631-637.
Thomson et al., "A Custon Microarray Platform for Analysis of MicroRNA Gene Expression", Nature Methods, 2004, vol. 1, No. 1, pp. 1-7, Supplementary Data.
Thomson et al., "Extensive post-transcriptional regulation of microRNAs and its implications for cancer", Genes and Development, 2006, vol. 20, pp. 2202-2207.
Thomson et al., "A Custom Microarray Platform for Analysis of MicroRNA Gene Expression", Nature Methods, 2004, vol. 1, No. 1, pp. 1-7.
Thorgeirsson et al., "Functional Genomics of Hepatocellular Carcinoma", Hepatology, 2006, vol. 43, No. 2, Supplement 1, pp. S145-S150.
Thorgeirsson et al., "Molecular pathogenesis of human hepatocellular carcinoma", Nature Genetics, 2002, vol. 31, pp. 339-346.
Tibshirani et al., "Diagnosis of multiple cancer types by shrunken centroids of gene expression", Proceedings of the National Academy of Sciences (PNAS), 2002, vol. 99, No. 10, pp. 6567-6572.
Tili et al., "Expression and Function of micro RNAs in Immune Cells During Normal or Disease State", International Journal of Medicine Sciences, 2008, vol. 5, No. 2, pp. 73-79.

(56) References Cited

OTHER PUBLICATIONS

Tili et al., "Mutator Activity Induced by microRNA-155 (miR-155) Links Inflammation and Cancer", Proceedings of the National Academy of Sciences (PNAS), 2011, vol. 108, No. 12, pp. 4908-4913.
Tkachuk et al., "Involvement of a Homolog of *Drosophila trithorax* by 11q23 Chromosomal Translocations in Acute Leukemias", Cell, 1992, vol. 71, pp. 691-700.
Tockman et al., "Considerations in Bringing a Cancer Biomarker to Clinical Application", Cancer Research, 1992, vol. 52, pp. 2711s-2718s.
Tokarz et al., "The Role of microRNA in metastatic colorectal cancer and its significance in cancer prognosis and treatment", ACTA Biochimica Polonica, 2012, vol. 59, No. 4, pp. 467-474.
Trapasso et al., "Fhit Interaction with Ferredoxin Reductase Triggers Generation of Reactive Oxygen Species and Apoptosis of Cancer Cells", The Journal of Biological Chemistry, 2008, vol. 283, No. 20, pp. 13736-13744.
Tricoli et al., "MicroRNA: Potential for Cancer Detection, Diagnosis, and Prognosis", Cancer Research, 2007, vol. 67, No. 10, pp. 4553-4555.
Tsunoda et al., "Oncogenic KRAS regulates miR-200c and miR-221/222 in a 3D-specific manner in colorectal cancer cells", Anticancer Research, 2011, vol. 31, No. 7, pp. 2453-2459, Abstract Only.
Tusher et al., "Significance analysis of microarrays applied to the ionizing radiation response", Proceedings of the National Academy of Sciences (PNAS), 2001, vol. 98, No. 9, pp. 5116-5121.
Ueda et al., "Relation Between microRNA Expression and Progression and Prognosis of Gastric Cancer: A microRNA Expression Analysis", The Lancet—Oncology, 2009, pp. 1-11.
Uil et al., "Generation of an Adenoviral Vector Containing an Addition of a Heterologous Ligand to the Serotpe 3 Fiber Knob", Cancer Gene Therapy, 2003, vol. 10, pp. 121-124.
Ulivi et al., "p16INK4A and CDH13 Hypermethylation in Tumor and Serum of Non-Small Cell Lung Cancer Patients", Journal of Cellular Physiolpogy, 2006, vol. 206, pp. 611-615.
Valeri et al., "MicroRNA-21 induces resistance to 5-fluorouracil by down-regulating human DNA MutS homolog 2 (hMSH2)", Proceedings of the National Academy of Sciences (PNAS), 2010, vol. 107, No. 49, pp. 21098-21103.
Valeri et al., "Pathogenetic and Clinical Relevance of microRNAs in Colorectal Cancer," Cancer Genomics Proteomics, 2009, vol. 6, No. 4, pp. 195-204, Abstract Only.
Valeri et al., "Epigenetics, miRNAs, and Human Cancer: A New Chapter in Human Gene Regulation", Mamm Genome, 2009, vol. 20, pp. 573-580.
Valeri et al., "Modulation of Mismatch Repair and Genomic Stability by miR-155", Proceedings of the National Academy of Sciences (PNAS), 2010, vol. 107, No. 15, pp. 6982-6987.
Van Den Eynde et al., "Is Tailored Adjuvant Treatment for Colon Cancer Possible?", Clinical Colorectal Cancer, 2010, vol. 9, No. 1, pp. 15-21.
Varnholt et al., "MicroRNA Gene Expression Profile of Hepatitis C Virus-Associated Hepatocellular Carcinoma", Hepatology, 2008, vol. 47, No. 4, pp. 1223-1232.
Varotti et al., "Comparison between the fifth and sixth editions of the AJCC/UICC TNM staging systems for hepatocellular carcinoma: multicentric study on 393 cirrhotic resected patients", European Journal of Surgical Oncology, 2005, vol. 31, pp. 760-767.
Vassilev, "Small-Molecule Antagonists of p53-MDM2 Binding", Cell Cycle, 2004, vol. 3, No. 4, pp. 419-421.
Vatolin et al., "A Novel Method to Detect Functional MicroRNA Targets", Journal of Molecular Biology, 2006, vol. 358, pp. 983-996.
Verschuur, "Acute Megakaryoblastic Leukemia", Orphanet Encyclopedia, 2004, pp. 1-5.
Virgilio et al., "Identification of the TCL1 Gene Involved in T-cell Malignancies," Proceedings of the National Academy of Sciences (PNAS), 1994, vol. 91, pp. 12530-12534.
Visone et al., "MiRNAs and Cancer", The American Journal of Pathology, 2009, vol. 174, No. 4, pp. 1131-1138.

Volinia et al., "Breast cancer signatures for invasiveness and prognosis defined by deep sequencing of microRNA", Proceedings of the National Academy of Sciences (PNAS), 2012, vol. 109, No. 8, pp. 3024-3029.
Volinia et al., "Prognostic microRNA/mRNA signature from the integrated analysis of patients with invasive breast cancer", Proceedings of the National Academy of Sciences (PNAS), 2013, Early Edition, pp. 1-5.
Volinia et al., "A MicroRNA Expression Signature of Human Solid Tumors Defines Cancer Gene Targets", Proceedings of the National Academy of Sciences (PNAS), 2006, vol. 103, No. 7, pp. 2257-2261.
Volinia et al., "Reprogramming of miRNA Networks in Cancer and Leukemia", Genome Research, 2010, vol. 20, pp. 589-599.
Wang et al., "Association Between CpG Island Methylation of the WWOX Gene and Its Expression in Breast Cancers", Tumor Biology, 2009, vol. 30, pp. 8-14.
Wang et al., "Ontogeny and Oncogenesis Balance the Transcriptional Profile of Renal Cell Cancer", Cancer Research, 2004, vol. 64, pp. 7279-7287.
Watson et al., "MicroRNA Expression Profiles in Barrett's Oesophagus", RACS Annual Scientific Congress, 2007, p. A45, Abstract #HP24.
Weidhaas, "Using microRNAs to Understand Cancer Biology", The Lancet—Oncology, 2009, p. 1.
Wiemer, "The Role of MicroRNAs in Cancer: No Small Matter", European Journal of Cancer, 2007, vol. 43, pp. 1529-1544.
Wijermans, "Low Dose Azanucleosides for High Risk (s)MDS and AML", Haematologica Reports, 2006, vol. 2, No. 15, pp. 74-76.
Wildi et al., "Critical evaluation of the different staging systems for hepatocellular carcinoma", British Journal of Surgery, 2004, vol. 91, pp. 400-408.
Wu et al., "Lenalidomide Enhances natural Killer Cell and Monocyte-Mediated Antibody-Dependent Cellular Cytotoxicity of Rituximab-Treated CD20+ Tumor Cells", Clinical Cancer Research, 2008, vol. 14, No. 14, pp. 4650-4657.
Wu et al., "Micro-RNA: A New Kind of Gene Regulators", Agricultural Sciences in China, 2006, vol. 5, No. 1, pp. 77-80.
Xi et al., "Prognostic Values of microRNAs in Colorectal Cancer", Biomarker Insights, 2006, vol. 1, pp. 113-121.
Yamamichi et al., "Locked Nucleic Acid In situ Hybridization Analysis of miR-21 Expression during Colorectal Cancer Development", Clinical Cancer Research, 2009, vol. 15, No. 12, pp. 4009-4016.
Yamashita et al., "Activation of Hepatic Stem Cell Marker EpCAM by Wnt-β-Catenin Signaling in Hepatocellular Carcinoma", Cancer Research, 2007, vol. 67, No. 22, pp. 10831-10839.
Yamashita et al., "EpCAM and α-Fetoprotein Expression Defines Novel Prognostic Subtypes of Hepatocellular Carcinoma", Cancer Research, 2008, vol. 68, No. 5, pp. 1451-1461.
Yanaihara et al., "Unique MicroRNA Molecular Profiles in Lung Cancer Diagnosis and Prognosis", Cancer Cell, 2006, vol. 9, pp. 189-198.
Yang et al., "Analysis of Sequence Variations in 59 MicroRNAs in Hepatocellular Carcinomas", Mutation Research, 2008, vol. 638, pp. 205-209.
Ye et al., "Predicting hepatitis B virus-positive metastatic hepatocellular carcinomas using gene expression profiling and supervised machine learning", Nature Medicine, 2003, vol. 9, No. 4, pp. 416-423.
Yekta et al., "MicroRNA-Directed Cleavage of HOXB8 mRNA", Science, 2004, vol. 304, pp. 594-596.
Yendamuri et al., "WW Domain Containing Oxidoreductase Gene Expression is Altered in Non-Small Cell Lung Cancer", Cancer Research, 2003, vol. 63, pp. 878-881.
Yi et al., "Exportin-5 mediates the nuclear export of pre-microRNAs and short hairpin RNAs", Genes & Development, 2003, vol. 17, pp. 3011-3016.
Yoo et al., "Epigenetic therapy of cancer: past, present and future", Nature Reviews Drug Discovery, 2006, vol. 5, pp. 37-50.
Yoon et al., "Prediction of Regulatory Modules Comprising MicroRNAs and Target Genes", Bioinformatics Genes and Genomes, 2005, vol. 21, Supplement 2, pp. ii93-ii100.
Yu et al., "Context-Dependent Bidirectional Regulation of the MutS Homolog 2 by Transforming Growth Factor β Contributes to

(56) References Cited

OTHER PUBLICATIONS

Chemoresistance in Breast Cancer Cells", Molecular Cancer Research, 2010, vol. 8, No. 12, pp. 1633-1642.

Yu et al., "Human microRNA clusters: Genomic organization and expression profile in leukemia cell lines", Biochemical and Biophysical Research Communications, 2006, vol. 349, pp. 59-68.

Yu et al., "Protein Phosphatase 2A, a Negative Regulator of the ERK Signaling Pathway, is Activated by Tyrosine Phosphorylation of Putative HLA Class II-Associated Protein I (PHAPI)/pp32 in Response to the Antiproliferative Lectin, Jacalin", The Journal of Biological Chemisty, 2004, vol. 279, No. 40, pp. 41377-41383.

Yuki et al., "Growth and Spread of Hepatocellular Carcinoma", Cancer, 1990, vol. 66, No. 10, pp. 2174-2179.

Zaman et al., "Current status and implications of microRNAs in ovarian cancer diagnosis and therapy", Jouranl of Ovarian Research, 2012, vol. 5, No. 44, pp. 1-11.

Zawacka-Pankau et al., "Expression and Simple One-Step Purification of Fragile Histidine Triad (Fhit) Tumor Suppressor Mutant Forms in *Escherichia coli* and their Interaction with Protoporphyrin IX", Biotechnology Letters, 2007, vol. 29, pp. 877-883.

Zeng et al., "Recognition and Cleavage of Primary microRNA Precursors by the Nuclear Processing Enzyme Drosha", The EMBO Journal, 2005, vol. 24, pp. 138-148.

Zhang et al., "Genomic and Epigenetic Alterations Deregulate microRNA Expression in Human Epithelial Ovarian Cancer", Proceedings of the National Academy of Sciences (PNAS), 2008, vol. 105, No. 19, pp. 7004-7009, Supporting Information.

Zhang et al., "In Vitro Study on effect of up-regulation of PETN expression by knowck-down of miR-221 and miR-222 in lung cancer cell line A549 cells on radiosensitization", Proceedings of the 5th Chinese Academic Conference on Tumors, 2008, p. 317.

Zhang et al., "Inhibitory effect of knocking down microRNA-221 and microRNA-222 on glioma cell growth in vitro and in vivo", Chinese Journal of Oncology, 2009, vol. 31, No. 10, pp. 721-726, Abstract Only.

Zhang et al., "Genomic and Epigenetic Alterations Deregulate microRNA Expression in Human Epithelial Ovarian Cancer", Proceedings of the National Academy of Sciences (PNAS), 2008, vol. 105, No. 19, pp. 7004-7009.

Zhang et al., "microRNAs Exhibit High Frequency Genomic Alterations in Human Cancer", Proceedings of the National Academy of Sciences (PNAS), 2006, vol. 103, No. 24, pp. 9136-9141.

Zhang et al., "Three Biomarkers Identified from Serum Proteomic Analysis for the Detection of Early Stage Ovarian Cancer", Cancer Research, 2004, vol. 64, pp. 5882-5890.

Zhang, "In vitro study on effect of up-regulation of TIMP3 expression by antisense miR-221 and miR-222 on inhibition of invasiveness of glioblastoma cell U251", The 8th Conference and Symposium Proceedings, China Genetic Association, 2004-2008, p. 139.

Zhao et al., "p53 Mediates the Negative Regulation of MDM2 by Orphan Receptor TR3", The EMBO Journal, 2006, vol. 25, pp. 5703-5715.

Zhou et al., "Binding of NF-kappaB p65 subunit to the promoter elements is involved in LPS-induced transactivation of miRNA genes in human biliary epithelial cells", Nucleic Acids Research, 2010, vol. 38, No. 10, pp. 3222-3232.

Zhu et al., "MicroRNA-21 Targets the Tumor Suppressor Gene Tropomyosin 1 (TPM 1)", The Journal of Biological Chemistry, 2007, vol. 282, No. 19, pp. 14328-14336.

\* cited by examiner

| miRNAs | Non Responders (3,4) vs Responders (1,2) (RQ) | (P-Value) |
|---|---|---|
| hsa-miR-592 | 3.0236 | 0.0003 |
| hsa-miR-484 | 0.5668 | 0.0027 |
| hsa-miR-217 | 0.5149 | 0.0054 |
| hsa-miR-642 | 0.465 | 0.0058 |
| hsa-miR-302d | 0.5223 | 0.0126 |
| hsa-miR-491 | 0.6721 | 0.0133 |
| hsa-miR-483-3p | 0.3787 | 0.0159 |
| hsa-miR-653 | 0.5583 | 0.018 |
| hsa-miR-181a | 0.6965 | 0.0223 |
| hsa-miR-671-3p | 0.6756 | 0.0244 |
| hsa-miR-19a | 1.4148 | 0.0285 |
| hsa-miR-744 | 0.7389 | 0.0412 |

Fig. 1C

| miRNAs | Non Responders (3,4) vs Responders (1,2) (RQ) | (P-Value) |
|---|---|---|
| hsa-miR484 | 0.5339 | 0.0007 |
| hsa-miR-642 | 0.3458 | 0.041 |
| hsa-miR-217 | 0.5097 | 0.0467 |

Fig. 1D

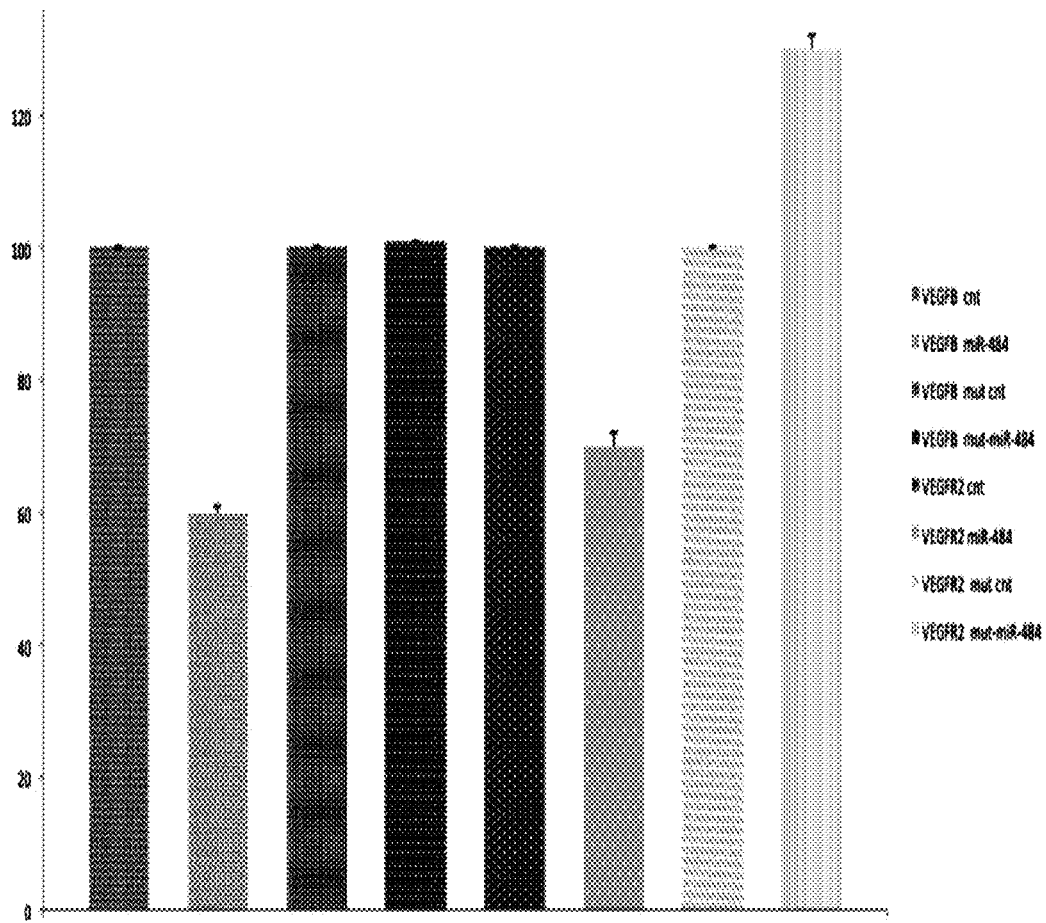
Fig. 3C
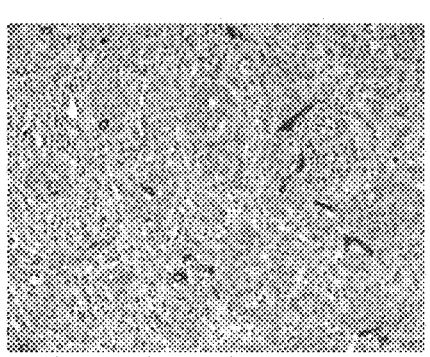 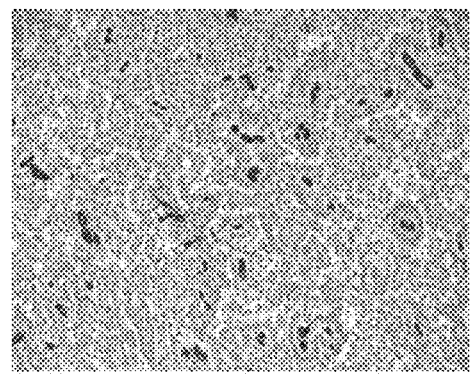
Fig. 4A  Fig. 4B

| Cell lines | miR-484 | CBDCA |
|---|---|---|
| IGROV | 0.27 | 5μg/ml |
| MDAH2774 | 0.32 | 40μg/ml |
| OVCAR8 | 0.13 | 10μg/ml |
| TOV112D | 0.28 | 15μg/ml |
| TOV21G | 0.18 | 10μg/ml |
| SK-OV3 | 0.31 | 50μg/ml |

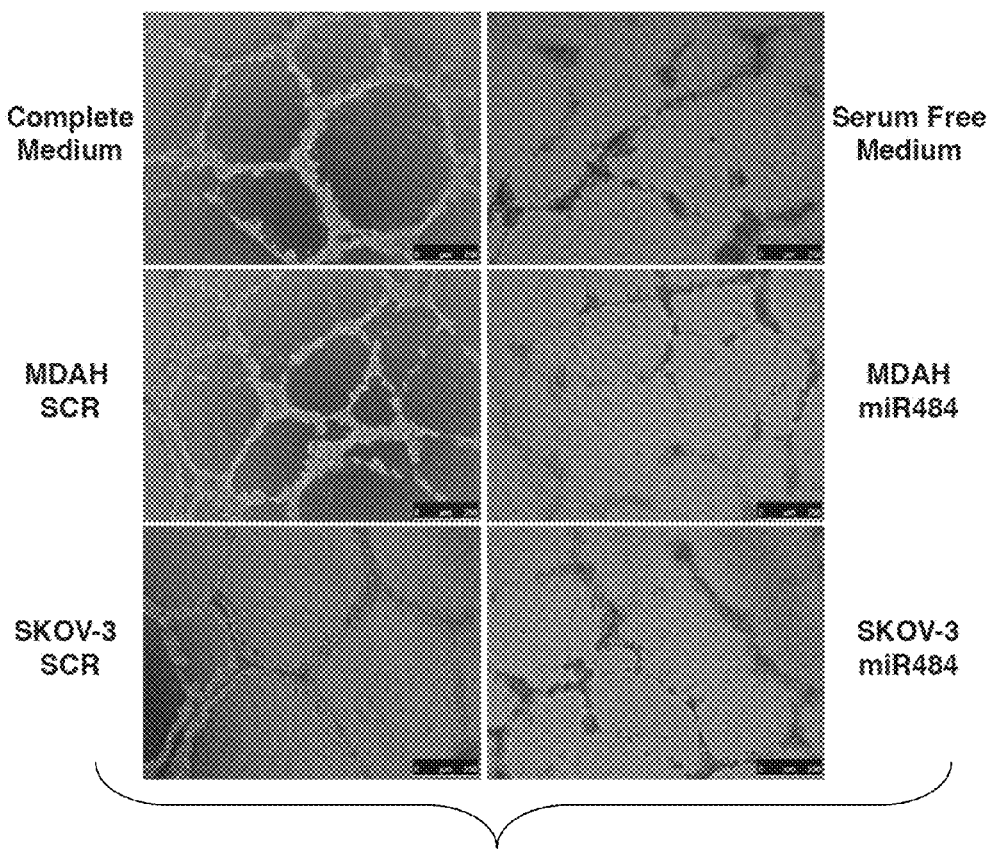

Fig. 7

| Baseline Characteristic of the 198 patients[#] with invasive serous ovarian carcinoma | Training Set (86pts) | Validation Set (112pts) |
|---|---|---|
| Characteristic | Value | Value |
| Age-yr | | |
|    Mean | 58 | 55 |
|    Range | 19-83 | 24-80 |
| Tumor Grade-no. (%) | | |
|    Low (1-2) | 20(23) | 18(15) |
|    High (3) | 66(77) | 94(85) |
| Tumor Stage-no. (%) | | |
|    I or II | 18(21) | 7(6) |
|    III or IV | 69(79) | 105(94) |
| Surgery Outcome-no. (%)* | | |
|    Optimal | 25(29) | 55(49) |
|    Suboptimal | 40(46) | 28(25) |
|    No Surgery | 21(25) | 29(26) |
| Response to chemotherapy no. (%)[+] | | |
|    Complete Response (CR) | 36(42) | 48(43) |
|    Partial response (PR) | 12(14) | 26(23) |
|    Stable Disease (SD) | 10(12) | 7(6) |
|    Progressive disease (PD) | 28(32) | 32(28) |

Fig. 8

| miRs | R vs. NR *<br>(Training Set) | R vs. NR*<br>(Validation Set) | Fold change |
|---|---|---|---|
| hsa-miR-484 | 0.000020105 | 0.001491375 | 1.324370929 |
| hsa-miR-193b | 0.000286734 | 0.719549542 | -1.070043322 |
| hsa-miR-422a | 0.000822871 | 0.854415379 | 1.030469801 |
| hsa-miR-374b. | 0.000823011 | 0.314578566 | -1.337324492 |
| hsa-miR-217 | 0.001620392 | 0.050611918 | 1.501812967 |
| hsa-miR-604 | 0.001869982 | 0.104765382 | -1.247350105 |
| hsa-miR-644 | 0.002431036 | 0.178471546 | -1.214548053 |
| hsa-miR-296.5p | 0.002582532 | 0.007587132 | -1.651727854 |
| hsa-miR-124 | 0.003109761 | 0.213853059 | -1.600521004 |
| hsa-miR-296.3p | 0.004141362 | 0.051726453 | -1.457937181 |
| hsa-miR-378. | 0.00634093 | 0.20643007 | 1.143691489 |
| hsa-miR-550 | 0.007909655 | 0.212295553 | 1.284239759 |
| hsa-miR-518e | 0.00816281 | 0.034440732 | -1.421747299 |
| hsa-miR-545. | 0.010468175 | 0.261685792 | 1.173170162 |
| hsa-miR-374a. | 0.011107408 | 0.48682279 | 1.224685644 |
| hsa-miR-491.5p | 0.011546449 | 0.783782167 | 1.023302769 |

Sixteen differentially expressed miRs distinguishing R from NR serous carcinomas. Out of the sixteen miRs initially identified, three miRs (in bold) were differentially expressed in the two groups and statistically significant, with two being down-regulated (miR-296-5p and miR-518e) and one being up-regulated (miR-484) in R tumors.

Fig. 9

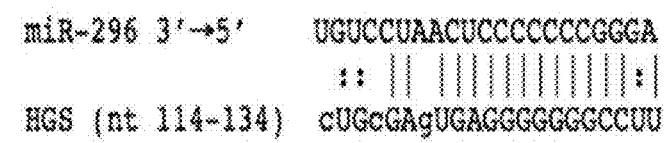

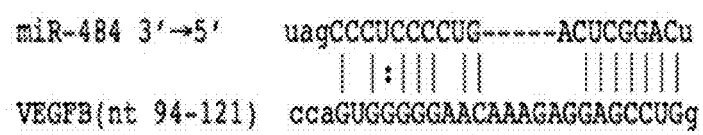

METHODS AND MATERIALS RELATED TO OVARIAN CANCER

CROSS REFERENCE TO RELATED APPLICATIONS

This application claims the benefit of U.S. Provisional Patent Application Ser. No. 61/547,109, filed Oct. 14, 2011, and U.S. Provisional Patent Application Ser. No. 61/675,449, filed Jul. 25, 2012, the disclosures of which are expressly incorporated herein by reference for all purposes.

STATEMENT REGARDING FEDERALLY SPONSORED RESEARCH

This invention was made with U.S. Government support under Grant Number U01CA152758 awarded by the National Institutes for Health (NIH/EDRN). The U.S. government has certain rights in the invention.

STATEMENT REGARDING THE SEQUENCE LISTING

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_53324_SEQ_LIST_2012-030.txt, created on Oct. 11, 2012 and is 3,287 bytes in size.

FIELD OF THE INVENTION

This application is in the field of medicine, particularly oncology. The invention is also in the field of molecular biology, particularly microRNAs.

BACKGROUND OF THE INVENTION

Ovarian cancer is the leading cause of gynecological cancer related-death in the developed world. Although progress has been made in its treatment by improved debulking surgery and the introduction of platinum-taxane regimens, the overall 5-year survival is only 29% in advanced stage disease, mostly due to diagnosis at an advance stage and to intrinsic and acquired resistance to platinum based chemotherapy. Identifying molecular markers of ovarian cancer chemoresistance is therefore of crucial importance. Successful translation of findings at the molecular level will lead to individualized treatment regimens, improved chemotherapeutic response rates and avoidance of unnecessary treatments.

In particular, epithelial ovarian cancer is the most common gynecologic malignancy; is highly aggressive and causes almost 125,000 deaths yearly. Despite advances in detection and cytotoxic therapies a very low percentage of patients with advance stage disease survive five years after the initial diagnosis. The high mortality of this disease is mainly due to resistance to the available therapies.

MicroRNAs (miRs) are a class of small non-coding RNAs, which modulate gene expression causing translational repression, mRNA cleavage, or destabilization. They are involved in numerous physiological cellular processes. Most importantly, accumulating evidence indicates that many miRs are aberrantly expressed in human cancers and their expression profiles can classify stage, subtype and prognosis of some cancers.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1D.

FIG. 1A. Analysis of training set using TLDA cards. Significant miRs are shown.

FIG. 1B. Centroid analysis of the identified miRs. In green down-regulated miRs, in red up-regulated miRs.

FIG. 1C. Significant miRs in the training set redefined in two-classes: Non responders (Stable disease and progressive disease) and in Responders (Complete responders and partial responders).

FIG. 1D. Significant miRs in the training set.

FIG. 2A. Tumor volume of mice injected in the right flank with MDAH-2274 control cells and in the left flank with MDAH-2274 overexpressing miR-484. The size of the tumors the day of the beginning of the CBDCA+Tax treatment (Left graph) and their increase after 21 days of treatment (Right graph) is shown.

FIG. 2B. In vivo imaging of nude mice injected in the right flank with SKOV-3 control cells and in the left flank with SKOV-3 overexpressing miR-484. Images were taken immediately before the start of the treatment (left panels) and after 21 days of CBDCA+Tax treatment.

FIG. 2C. Quantification of in vivo EGFP fluorescence of the experiment described in B at day 0 (left graph) and after 7, 14 and 21 days of treatment (right graph).

FIG. 2D. Effects of intratumoral injection of lentivirus expressing control (scr) or miR-484 in the presence of CBDCA+Tax treatment. The significant differences are reported in each graph as evaluated by nonparametric t-Test. Differences were considered significant when <0.05.

FIGS. 3A-3C.

FIG. 3A. Left panel: Alignment of potential miRs-484 binding sites in the 3'UTR of VEGFB, showing VEGFB UTR (SEQ ID NO: 12; hsa-miR-484 in the 3' to 5' order (SEQ ID NO: 11); and, VEGFR Mut (SEQ ID NO: 13). Middle panel: Western blot analysis of VEGFB after transfection of miR-484 in 293 cells. Right panel: Densitometric ratio between the expression of Tubulin, and VEGFB.

FIG. 3B. Left panel: Alignment of potential miRs-484 binding sites in the 3'UTR of VEGFR2 showing VEGFR2 UTR (SEQ ID NO: 14; hsa-miR-484 in the 3' to 5' order (SEQ ID NO: 11); and, VEGFR2 Mut (SEQ ID NO: 15). Middle panel: Western blot analysis of VEGFR2 after transfection of miR-484 in HUVEC cells. Right panel: Densitometric ratio between the expression of Tubulin, and VEGFR2.

FIG. 3C. Luciferase assay (from left to right) of vectors containing the 3'UTR of the wild-type VEGFB mRNA transfected with scramble miR (VEGFB cnt) or with miR-484 (VEGFB-miR-484), vectors containing the mutated miR-484 binding site transfected with scramble miR (VEGFB-mut cnt) or with miR-484 (VEGFB-mut-miR-484), vectors containing the 3'UTR of the wild-type VEGFR2 mRNA transfected with scramble miR (VEGFR2 cnt) or with miR-484 (VEGFR2-miR-484) and vectors containing the mutated miR-484 binding site transfected with scramble miR (VEGFR2-mut cnt) or with miR-484 (VEGFR2-mut-miR-484).

FIGS. 4A-4D.

FIGS. 4A-4B. CD34 staining of responders (FIG. 4A) and non-responders (FIG. 4B) tumors, showing a higher vascular density with pronounced microvessel formation in the latter.

FIG. 4C. Tumor vessels count in mice xenograft tumors transduced with miR-484 or control in SK-OV3 or MDAH2774 cells.

FIG. 4D. Regression analysis of miR-484 and vessels number.

FIGS. 5A-5B. Expression of miR-484 in ovarian cancer derived cell lines after stable transfection (FIG. 5A) and in CM medium derived from the same cell lines (FIG. 5B) is shown.

FIG. 5C. Levels of miR-484 in HUVEC cells co-cultured with ovarian cancer derived cell lines.

FIG. 5D. Confocal microscopy image of co-cultured SK-OV3 cells transfected with miR-484-FITC-conjugated (Green) and HUVEC stained with CD31 antibody-Texas Red-conjugated (Red).

FIG. 5E. Right panel: Western Blot analysis of VEGFR2 expression in HUVEC cells cultured in CM from SK-OV3 cells stable transfected with miR-484 or EGFP. Left panel: Densitometric ratio between the expression of Tubulin, and VEGFR2.

FIG. 6A. Expression of miRs 296 and 484 in EOC.

FIG. 6B. Table shows the normalized expression levels of miR-296, 484 in the indicated ovarian cancer cell lines and their IC value for CBDCA treatment evaluated as described in the methods section.

FIGS. 6C-6D. Effects of miR-484 and miR-296 expression on the in vitro sensitivity of MDAH-2274 (FIG. 6C) and SKOV-3 (FIG. 6D) cells to CBDCA (upper panels) and Taxol (lower panels) treatments.

FIG. 7. Images of HUVEC incubated on 3D Matrigel Matrix for 20 hours in the presence of the indicated Conditioned Medium (CM) or controls. As shown, CM from SKOV-3 and MDAH2774 transduced miR-484 cells reduces the ability of HUVEC to properly form and maintain tube-like structures in 3D when compared to CM form control cells.

FIG. 8. Table showing patient data of invasive serous carcinoma of the ovary, data on clinical outcome.

FIG. 9. miR expression signature in Responser vs. Refractory ovarian carcinomas.

FIGS. 10A-10D.

FIG. 10A. Alignment of potential miRs—296 (SEQ ID NO: 9) and 484 (SEQ ID NO: 11) binding sites in the 3'UTR of the HGS (SEQ ID NO: 10) and VEGFB (SEQ ID NO: 12), respectively.

FIG. 10B. Expression of miRs 296 and 484 after transfection in 293 cells is shown.

FIG. 10C. Left panels, Western blot analysis of HGS, VEGFB and Tubulin after transfection of miRs—296 and 484 in 293 cells, Right panels, densitometric ratio between the expression of Tubulin, HGS and VEGFB.

FIG. 10D. Luciferase assay vectors containing the 3'UTR of the wild-type HGS mRNA transfected with scramble miR (HGS cnt) or with miR-296 (HGS-miR 296) and vectors containing the mutated miR 296 binding site transfected with scramble miR(HGSmut cnt) or with miR-296 (HGSmut-miR 296).

FIG. 11A. Tumor vessels count in 30 cases (15 NR and 15 R) of human serous ovarian carcinoma.

FIG. 11B. Tumor vessels count in mice xenograft tumors transduced with miR 484 or control in SKOV-3 or MDAH2774 cells.

FIG. 11C. CD34 staining of NR (left panel) and R (right panel) tumors, showing a higher vascular density with pronounced microvessel formation in the former.

SUMMARY OF THE INVENTION

Figure 1A:
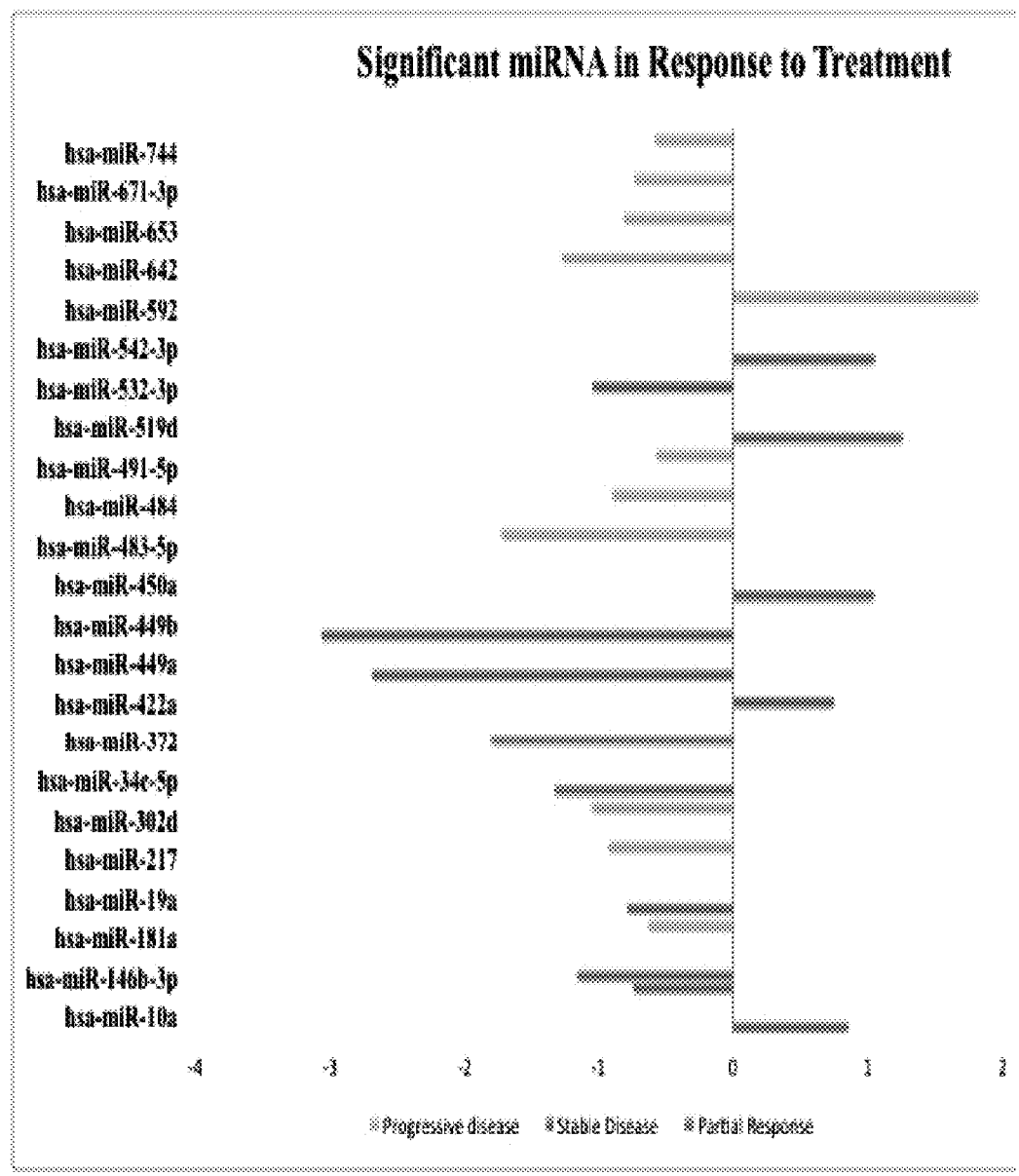

In a first aspect, described herein is a method of diagnosing ovarian cancer that is resistant to chemotherapeutic intervention in a subject, comprising:

a) identifying miR-484, miR-642 and/or miR-217 expression levels in a sample from the subject, as compared to control expression levels, and b) diagnosing chemoresistant ovarian cancer in the subject if the subject has decreased miR-484, miR-642 and/or miR-217 expression levels compared to the control expression levels, or c) diagnosing no chemoresistant ovarian cancer in the subject if the subject does not have decreased miR-484, miR-642 and/or miR-217 expression levels compared to the control expression levels.

In certain embodiments, the method further includes identifying expression levels of: miR-592, miR-302d, miR-491, miR-483-5p, miR-653, miR-181a, miR-671-3p, miR-19a and/or miR-744, as compared to control expression levels.

In certain embodiments, the method includes identifying expression levels of: miR-296-5p and/or miR-518e, as compared to control expression levels.

In certain embodiments, the method comprises identifying the levels of: miR-484, miR-642 and miR-217.

In certain embodiments, the chemotherapeutic intervention comprises administration of one or more of: a platinum-based drug, carboplatin (Paraplatin®), cisplatin (Platinol®), a taxane, paclitaxel (Taxol®), docetaxel (Taxotere®), gemcitabine (Gemzar®), doxorubicin (Adriamycin®, Doxil®), etoposide (Vepesid®), vinorelbine (Navelbine®), xabepilone (Ixempra®), an epithelone drug, bevacizumab (Avastin®) and/or phenoxodiol.

In certain embodiments, the method includes:

1) reverse transcribing miR-484, miR-642 and/or miR-217 RNA from the sample obtained from the subject to provide a signature of target oligodeoxynucleotides;

2) hybridizing the target oligodeoxynucleotides to a microarray comprising miR-484, miR-642 and/or miR-217 miRNA-specific probe oligonucleotides to provide a hybridization profile for the test sample; and 3) comparing the profile of step (2) to control.

In certain embodiments, the method includes comparing the sample hybridization profile to a hybridization profile generated from a control sample.

In certain embodiments, the method includes comparing the sample hybridization profile to a database, statistics, or table of miR levels associated with non-cancerous samples.

In certain embodiments, the ovarian cancer is serous epithelial ovarian carcinoma.

In certain embodiments, decreased miR-484 expression compared to control confirms chemoresistant ovarian cancer diagnosis.

In another aspect, described herein is a method of determining whether a human subject has a poor survival prognosis for an ovarian cancer, comprising:

a) measuring the level of a miR gene product signature in a sample of ovarian tissue from the human subject, the miR gene product signature consisting of miR gene products: miR-484, mir-642 and/or miR-217; and b) determining the poor survival prognosis of the human subject when a decrease in the levels one or more of the miR gene products in the sample, relative to corresponding levels of miR gene products in a control sample of cancer-free ovarian tissue, is indicative of the human subject having a poor survival prognosis for ovarian cancer.

In certain embodiments, the method includes:

1) reverse transcribing miR-484, miR-642 and/or miR-217 RNA from the sample to provide a signature of target oligodeoxynucleotides;

2) hybridizing the target oligodeoxynucleotides to a microarray comprising miR-484, miR-642 and/or miR-217 miRNA-specific probe oligonucleotides to provide a hybridization profile for the test sample; and 3) comparing the profile of step (2) to control.

In certain embodiments, the step of determining the survival prognosis of the subject distinguishes serous ovarian cancer from other ovarian cancers.

In certain embodiments, the step of determining the survival prognosis of the subject predicts response to chemotherapeutic intervention.

In certain embodiments, a signature set of miR-484, miR-642 and/or miR-217 hybridize to one or more probes that are specific for miR-484, miR-642 and/or miR-217, respectively, and the presence of a decrease in the levels of miR-484, miR-642 and/or miR-217, relative to the control sample, is indicative of poor response to chemotherapeutic invention, a prognosis of poor survival in human patients, and/or the presence of serous ovarian cancer.

In another aspect, described herein a method for determining a chemoresistant ovarian cancer is a subject, the method comprising:

a) detecting a miRNA expression profile of a sample from the subject, b) comparing the miRNA profile of the sample to a miRNA expression profile of a control sample comprised of non-cancerous ovarian cells, and c) determining chemoresistant ovarian cancer where the miRNA expression profile comprises a statistically significant change in the expression of one or more of: hsa-miR-484, hsa-miR-642 and/or hsa-miR-217 in the sample.

In certain embodiments, the statistically significant change is a decrease in the expression level of miR-484.

In certain embodiments, the microRNA signature comprises at least: hsa-miR-484, hsa-miR-642 and hsa-miR-217.

In another aspect, described herein is a method for the assessment of a clinical condition of a patient comprising the steps:

a) providing a biological sample from the patient, b) determining expression levels a predetermined signature of miRNAs in the sample to obtain a miRNA expression profile, the predetermined signature of miRNAs comprising at least: hsa-miR-484, hsa-miR-642 and/or hsa-miR-217, c) comparing the miRNA expression profile of step (b) with one or more reference miRNA expression profiles characteristic for different diseases including ovarian cancer, and d) assessing the clinical condition of the patient based on the comparison of step (c).

In certain embodiments, the reference miRNA expression profiles are obtained from a database found on one or more of: an internet database, a centralized database or a decentralized database.

In certain embodiments, the determination comprises qualitative, quantitative or semiquantitative determination of the predetermined signature of miRNAs.

In certain embodiments, the determination comprises nucleic acid hybridization, nucleic acid amplification, polymerase extension, sequencing, mass spectroscopy or any combination thereof.

In another aspect, described herein is a kit for the assessment of a clinical condition of a patient comprising:

a) biomarkers for determining a predetermined signature of miRNAs in a biological sample from a patient, the predetermined signature of miRNAs comprising at least one of: hsa-miR-484, hsa-miR-642 and/or hsa-miR-217, and b) a plurality of miRNA reference expression profiles characteristic for different diseases including ovarian cancer.

In certain embodiments, the miRNA reference expression profiles are laid down in a database, such as an internet database, a centralized or a decentralized database.

In another aspect, described herein is a kit for diagnosing ovarian cancer in a patient comprising:

a) a capture reagent comprising one or more detectors specific for at least one ovarian cancer diagnostic biomarker, wherein at least a first ovarian cancer biomarker is a miR-484 biomarker, b) a detection reagent, and c) instructions for using the kit to diagnose a patient as having ovarian cancer when the expression levels of the miR-484 diagnostic biomarker in a biological sample from the patient is lower than the expression level of the same biomarkers in a control subject without ovarian cancer.

In certain embodiments, the kit further includes one or more additional ovarian cancer diagnostic biomarkers selected from miR-642 and miR-217 biomarkers. In certain embodiments, the kit further includes one or more additional ovarian cancer diagnostic biomarkers selected from: hsa-miR-592, hsa-miR-484, hsa-miR-217, hsa-miR-642, hsa-miR-302d, hsa-miR-491, hsa-miR-483-5p, hsa-miR-653, hsa-miR-181a, hsa-miR-671-3p, hsa-miR-19a and/or hsa-miR-744.

In another aspect, described herein is a set of oligo- or polynucleotides for diagnosing ovarian cancer comprising the sequences of a set of miRNAs selected from: miR-484, miR-642 and miR-217, and/or the complements thereof.

In another aspect, described herein is a method for diagnosing ovarian cancer in a patient comprising:

a) detecting expression levels of at least one diagnostic biomarker in a biological sample from the patient, wherein at least a first diagnostic biomarker is a miR-484 biomarker, and b) diagnosing the patient as having ovarian cancer when the expression level of at least the mir-484 diagnostic biomarker in the patient sample is lower than normal expression levels of the same biomarker derived from a biological sample from a control subject without ovarian cancer.

In certain embodiments, the method further includes detecting expression levels of one or more additional ovarian cancer diagnostic biomarkers selected from miR-642 and miR-217 biomarkers. In certain embodiments, the method further includes detecting expression levels of one or more additional ovarian cancer diagnostic biomarkers selected from: hsa-miR-592, hsa-miR-484, hsa-miR-217, hsa-miR-642, hsa-miR-302d, hsa-miR-491, hsa-miR-483-5p, hsa-miR-653, hsa-miR-181a, hsa-miR-671-3p, hsa-miR-19a and/or hsa-miR-744.

In certain embodiments, the method comprises the steps of:

a) obtaining the sample, wherein the sample comprises an ovarian cell;

b) amplifying at least one miRNA in the miRNA expression profile from the sample;

c) determining the miRNA expression profile of the sample; and d) comparing the miRNA expression profile of the sample to a control miRNA signature comprising: miR-484, miR-642 and/or miR-271, wherein replication of the control miRNA signature within the miRNA expression profile sample indicates that the sample comprises ovarian cancer cells resistant to chemotherapeutic treatment.

Also described herein are devices to diagnose ovarian cancer. The ovarian cancer diagnostic device can comprises:

a) a capture reagent comprising one or more detectors specific for at least miR-484, miR-642 and/or miR-217 diagnostic biomarkers, and b) detecting reagents for detecting an expression level of the at least the diagnostic biomarkers in a biological sample from the patient, wherein the patient is diagnosed as having ovarian cancer when the expression levels of the at least one of the diagnostic biomarkers in the patient biological sample is lower than the expression levels in a control subject without ovarian cancer.

The capture reagent of the devices can be an organic or inorganic chemical, biomolecule, or any fragment, homolog, analog, conjugate, or derivative thereof that specifically interacts with the diagnostic biomarkers. In certain embodiments, the capture reagent is a protein and/or an antibody, and may be immobilized on a solid support.

Also described herein is a diagnostic biomarker panel that differentiates between ovarian cancer patients which may be responsive to treatment with a chemotherapeutic agent versus patients with a chemoresistant ovarian cancer, which would not benefit from treatment with a chemotherapeutic agent.

The diagnostic biomarker panel can generally include at least chemoresistant ovarian cancer diagnostic biomarkers for differentiating these two types of patients, and/or identifying patients with a highest risk for a poor prognostic outcome and/or poor response to currently available chemotherapeutic intervention. Identifying patient at risk for such poor prognosis will lead to more specific, aggressive therapies for these subpopulations of ovarian cancer patients.

In particular embodiments, a combination of biomarkers results greatly increases the accuracy of the diagnosis.

In another broad aspect, described herein is a method of diagnosing serous ovarian cancer related to chemoresistance in a subject, comprising:

a) identifying the relative miR-484, miR-642 and/or miR-217 expression compared to control, and b) diagnosing serous ovarian cancer related to chemoresistance in the subject if the subject has decreased miR-484, miR-642 and/or miR-217 expression compared to control, or c) diagnosing no serous ovarian cancer related to chemoresistance in the subject if the subject does not have decreased miR-484, miR-642 and/or miR-217 expression compared to control.

In certain embodiments, the method includes identifying the relative miR-expression, as compared to a control, where step a) further includes identifying one or more additional miRs listed in FIG. 1C: miR-592, miR-302d, miR-491, miR-483-5p, miR-653, miR-181a, miR-671-3p, miR-19a and miR-744. In certain embodiments, the method includes identifying the relative miR-518e and/or 296-5p expression compared to control.

In certain embodiments, the method includes designing a treatment plan based on the diagnosis. In certain embodiments, the method includes administration of a treatment based on the diagnosis. In certain embodiments, the method includes administering an anti-angiogenic treatment in the event that an ovarian cancer is diagnosed. In certain embodiments, the method includes determining prognosis based on the diagnosis.

In another broad aspect, there is provided herein a method to increase drug sensitivity in a patient with epithelial ovarian cancer, comprising increasing levels of miR-484 in epithelial ovarian cancer cells of a patient with epithelial ovarian cancer.

In certain embodiments, the miR is increased via a device selected from the group consisting of: gene therapy, small molecule, or biologic.

In another broad aspect, there is provided herein a method to suppress epithelial ovarian cancer-related angiogenesis, comprising increasing levels of miR in epithelial ovarian cancer cells of a patient with epithelial ovarian cancer.

In certain embodiments, the miR is increased via a device selected from the group consisting of: gene therapy, small molecule, or biologic.

In certain embodiments, the method includes determining the survival prognosis of the subject distinguishes serous ovarian cancer from other ovarian cancers.

In certain embodiments, the method includes determining the survival prognosis of the subject predicts response to chemotherapeutic intervention.

In certain embodiments, the signature of miR-484, miR-642 and miR-217 hybridize to probes that are specific for miR-484, miR-642 and miR-217, respectively, and the presence of a decrease in the levels of miR-484, miR-642 and miR-217, relative to the control sample, is indicative of poor response to chemotherapeutic invention, a prognosis of poor survival in human patients, and/or the presence of serous ovarian cancer.

In another broad aspect, there is provided herein a method of determining the presence of a chemoresistant ovarian cancer, comprising the steps of:

a) obtaining a sample of an ovarian cancer cell;

b) extracting total RNA of the sample;

c) amplifying at least one miRNA from the sample;

d) determining a miRNA expression profile of the sample; and e) comparing the miRNA expression profile of the tumor sample to a miRNA signature consisting of one or more of: miR-484, miR-642 and miR-271, wherein replication of the miRNA signature within the miRNA expression profile sample indicates that the ovarian cancer cells are resistant to chemotherapeutic treatment. In certain embodiments, the ovarian cancer comprises serous ovarian cancer.

In another broad aspect, there is provided herein a microRNA signature comprising one or more miRNAs selected from the group consisting of hsa-miR-484, hsa-miR-642 and hsa-miR-217, wherein a decreased expression of these miRNAs in an ovarian cell indicates that the ovarian cell is an ovarian cancer cell.

In certain embodiments, a statistically significant change in the expression of any one of these miRNAs indicates that the ovarian cancer cell is resistant to chemotherapeutic intervention.

In another broad aspect, there is provided herein a set of oligo- or polynucleotides for diagnosing ovarian cancer comprising the sequences of a set of miRNAs selected from: miR-484, miR-642 and miR-217, and/or the complements thereof.

These and other objectives and advantages of the present invention, some of which are specifically described and others that are not, will become apparent from the detailed description and claims that follow.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Definitions

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The terms "miR," "mir" and "miRNA" generally refer to microRNA, a class of small RNA molecules that are capable of modulating RNA translation (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002, each of which is incorporated by reference herein).

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Control: A "control" refers to a sample or standard used for comparison with an experimental sample, such as a tumor sample obtained from a patient.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences, which are known in the art.

MicroRNA (miRNA): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of mi in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miRNA, or both.

Subject: As used herein, the term "subject" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

In some embodiments of the present methods, use of a control is desirable. In that regard, the control may be a non-cancerous cell/tissue sample obtained from the same patient, or a cell/tissue sample obtained from a healthy subject, such as a healthy tissue donor. In another example, the control is a standard calculated from historical values. Tumor samples and non-cancerous cell/tissue samples can be obtained according to any method known in the art. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The level of at least one miR gene product can be measured in cells of a biological sample obtained from the subject. For example, a tissue sample can be removed from a subject suspected of having ovarian cancer, by conventional biopsy techniques. In another embodiment, a blood sample can be removed from the subject, and white blood cells can be isolated for DNA extraction by standard techniques. The blood or tissue sample is preferably obtained from the subject prior to initiation of radiotherapy, chemotherapy or other therapeutic treatment. A corresponding control tissue or blood sample, or a control reference sample, can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "up-regulated" or "increased"). As used herein, expression of a miR gene product is increased when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated" or "decreased"). As used herein, expression of a miR gene is decreased when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

An alteration (i.e., an increase or decrease) in the level of a miR gene product in the sample obtained from the subject, relative to the level of a corresponding miR gene product in a control sample, is indicative of the presence of ovarian cancer in the subject. In one embodiment, the level of at least one miR gene product in the test sample is greater than the level of the corresponding miR gene product in the control sample. In another embodiment, the level of at least one miR gene product in the test sample is less than the level of the corresponding miR gene product in the control sample.

In a certain embodiment, the at least one miR gene product is selected from the groups as shown in the Tables and Figures herein.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in the Tables herein and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), J. Mol. Biol. 113:237-251 or by the random priming method of Fienberg et al. (1983), Anal. Biochem. 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N-(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in the Tables herein, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set (or signature) of oligonucleotide (e.g., oligodeoxynucleotide) probes that are specific for a set of miR genes.

Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in ovarian cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancer cells, and within cancer cell types, different prognosis states (for example, good or poor long term survival prospects) may be determined. By comparing expression profiles of ovarian cells in different states, information regarding which genes are important (including both up- and down-regulation of genes) in each of these states is obtained. The identification of sequences that are differentially expressed in cancer cells or normal cells, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the miR or disease expression profile or convert a poor prognosis profile to a better prognosis profile.

Accordingly, the invention provides methods of diagnosing whether a subject has, or is at risk for developing, cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample, wherein an alteration in the signal of at least one miRNA is indicative of the subject either having, or being at risk for developing, ovarian cancer. In one embodiment, the microarray comprises miRNA-specific probe oligonucleotides for human miRNAs.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., ovarian cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, e.g., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with ovarian cancer, comprising measuring the level of at least one miR gene product, which is associated with a particular prognosis in ovarian cancer (e.g., a good or positive prognosis, a poor or adverse prognosis), in a test sample from the subject. According to these methods, an alteration in the level of a miR gene product that is associated with a particular prognosis, in the test sample, as compared to the level of a corresponding miR gene product in a control sample, is indicative of the subject having ovarian cancer with a particular prognosis. In one embodiment, the miR gene product is associated with an adverse (i.e., poor) prognosis. Examples of an adverse prognosis include, but are not limited to, low survival rate and rapid disease progression.

In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of ovarian cancer. Therefore, altering the level of the miR gene product (e.g., by decreasing the level of a miR that is up-regulated in ovarian cancer cells, by increasing the level of a miR that is down-regulated in ovarian cancer cells) will ameliorate the symptoms of chemoresistant ovarian cancer.

Accordingly, the present invention encompasses methods of treating ovarian in a subject, wherein at least one miR gene product is deregulated (e.g., down-regulated, up-regulated) in the cells (e.g., ovarian cancer cells) of the subject. In one embodiment, the level of at least one miR gene product in a test sample (e.g., ovarian cancer sample) is greater than the level of the corresponding miR gene product in a control sample. In another embodiment, the level of at least one miR gene product in a test sample (e.g., ovarian cancer sample) is less than the level of the corresponding miR gene product in a control sample. When the at least one isolated miR gene product is down-regulated in the ovarian cancer cells, the method comprises administering an effective amount of the at least one isolated miR gene product, or an isolated variant or biologically-active fragment thereof, such that proliferation of cancer cells in the subject is inhibited. For example, when a miR gene product is down-regulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in the Tables herein) that is down-regulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with ovarian (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with ovarian cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, hormonal therapy, radiation therapy and combinations (e.g., chemoradiation).

Hormonal therapy is an option for patients who cannot tolerate or are not helped by chemotherapy. Hormonal therapy drugs include tamoxifen (Nolvadex®), and aromatase inhibitors such as letrozole (Femara®), anastrozole (Arimidex®), and exemestane (Aromasin®).

MicroRNA-based treatments and diagnostics can improve treatments for ovarian cancer and may involve combinations of therapies. In treating ovarian cancer, a platinum-based drug, such as carboplatin (Paraplatin®) or cisplatin (Platinol®) may be used. Other treatments may include a taxane, such as paclitaxel (Taxol®) or docetaxel (Taxotere®). Currently, paclitaxel is the drug most often used as initial therapy in combination with a platinum drug.

Other drugs used may be: gemcitabine (Gemzar®), doxorubicin (Adriamycin®, Doxil®), etoposide (Vepesid®), vinorelbine (Navelbine®), xabepilone (Ixempra®) and other epithelone drugs, bevacizumab (Avastin®), and phenoxodiol.

Embodiments of the invention may be used to select appropriate drugs and tailor the treatment of patients based on predictions and indications of the responsiveness of the tumor to selected treatments. For example, bevacizumab (Avastin®) targets vascular endothelial growth factor (VEGF), a protein involved in cancer cell growth. The VEGFB and VEGFR2 pathways are influenced by miR-484 and miR-296-5p. MicroRNA measurements can be used to predict drug efficacy and chemoresistance.

When the at least one isolated miR gene product is up-regulated in the cancer cells, the method comprises administering to the subject an effective amount of a compound that inhibits expression of the at least one miR gene product, such that proliferation of ovarian cancer cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, for example, ovarian cancer, including preventing or delaying the onset of the disease symptoms, and/or lessening the severity or frequency of symptoms of the disease or condition. The terms "subject" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from ovarian cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating ovarian cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), J. Virol. 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), Gene Therap. 2:301-310; Eglitis (1988), Biotechniques 6:608-614; Miller (1990), Hum. Gene Therap. 1:5-14; and Anderson (1998), Nature 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), Nat. Biotech. 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., ovarian cancer). One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in the Tables herein. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), Science 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), Nucl. Acids Res. 23:2092-96; Hammann et al. (1999), Antisense and Nucleic Acid Drug Dev. 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a cancer (e.g., ovarian cancer). As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibiting compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The miR gene products or miR gene expression-inhibiting compounds can be administered to a subject by any means suitable for delivering these compounds to cancer cells of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Mirus Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors (e.g., ovarian cancers), will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating ovarian cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in ovarian cancer cells relative to suitable control cells.

Description

Despite advances in detection and cytotoxic therapies a very low percentage of patients with advance stage disease survive five years after the initial diagnosis. The high mortality of this disease is mainly due to resistance to the available therapies.

Considering the poor prognosis of ovarian neoplasms, mainly due to late diagnosis and low response to chemotherapy, the inventors have now identified predictive markers of therapeutic response and new molecular target/s to increase sensitivity to treatment.

Described herein is a molecular signature of miRs that is useful to identify those patients who will respond to conventional chemotherapy and those who will effectively benefit from the addition of anti-angiogeneic compounds, thereby also reducing the costs of the therapies and improve the efficacy of the drugs.

Moreover, the data demonstrates that blockage of VEGF by the use of an anti-VEGFA antibody alone is not useful in ovarian cancer patients unless VEGFB signaling is also blocked. Alternatively, small compounds such as functionalized nanoparticles targeting the VEGFR1 and 2 receptors, can be employed as effective therapy in this patients changing the course of prognosis and treatment of ovarian cancer.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Methods

After the Institutional Review Board approved the study and all patients gave their informed consent, the inventors obtained 198 specimens of invasive serous carcinoma of the ovary. Data on clinical outcome were obtained from patients' records. Response to initial chemotherapy was classified according to the RECIST guideline as complete response (CR), partial response (PR), stable disease (SD) and progressive disease (PD).

miR Expression Profiling and Data Validation.

miR expression profiling was performed on the training set (86 samples) using TaqMan® Array Human MicroRNA Set v2.0, containing a total of 676 unique assay. Differential expressed miRs were validated on the validation set (112 samples) using the TaqMan® MicroRNA assay.

Statistical Analysis.

TaqMan Low Density Array cards (TLDA) and RT-PCR data were analysed using the comparative CT ($\Delta\Delta C_T$) method for relative quantitation of gene expression on Data Assist ver.1.2 (Applied Biosystems, Foster City, Calif.). For each sample the mean miRNA expression value was calculated as the average of Ct values smaller than 35. Samples were labeled based either on their response to first chemotherapy or other clinical parameters. One-way anova test was applied to identify differentially expressed miRNA using R software. Global median normalization was used for the expression analysis of the TLDA cards. miR-16 and miR-191, two among the most invariable miRNAs in the training set, were used as endogenous controls for normalization of the RT-PCR in the validation set. All data were expressed as the mean±SEM. Statistically significant differences between non-responders vs. responders (control) were determined by using the non-paired Student's two-tailed t-test. A value of P<0.05 was considered statistically significant. Centroid analysis was performed using Cluster combined with Java TreeView for graphical output.

Generation of Ovarian Carcinoma Cell Lines Expressing miR-484 and miR-296.

Lentivirus expressing miR-484 was produced in 293FT cell lines (Invitrogen), using the System Biosciences (SBI, USA) miR Precursor Constructs, which contain dual expression of the specific miR and the copEGFP fluorescent marker, for simple identification and monitoring of cells positive for transfection and transduction.

In Vivo Analysis of Ovarian Carcinoma Cell Lines Growth and Susceptibility to Carboplatin+Taxol Treatment.

Two approaches were used to evaluate the effects of miR-484 expression on in vivo chemosensitivity: 1) MDAH-2774 cells scrambled-miR (right flank) or miR-484 (left flank) and SKOV-3 scrambled-miR (right flank) or miR-484 (left flank) were injected and treated with intraperitoneal administration of Carboplatin (15 mg/kg) plus Taxol (5 mg/kg) twice a week, for 3 weeks. Tumor growth was follow by caliper measurement and/or by GFP visualization using the Ivis Lumina, Caliper Lifesciences. 2) Direct intratumoral delivery of lentiviruses expressing scrambled-miR (right flank) or miR484 (left flank) associated with carboplatin (15 mg/kg) plus taxol (5 mg/kg) intraperitoneal treatment.

RNA Extraction Procedure.

Total RNA for low-density array analysis was isolated from paraffin embedded tissue (FFPE) using High Pure FFPE RNA Micro Kit (Roche Applied Science Mannheim Germany) according to manufacturer protocol. Following extraction, total RNA was quantified using NanoDrop Spectrophotometer (Thermo Fisher Scientific Inc., USA).

MicroRNA Expression Profiling Using TaqMan® Array Human microRNA Set Cards v2.0.

MiR expression profiling was performed on the training set using TaqMan® Array Human MicroRNA Set v2.0, a preconfigured 2 micro fluidic card set, A and B, containing 676 unique assays specific to human microRNAs. In addition, each array contained four control assays, three selected candidate endogenous control assays and one negative control assay. This array set required the use of Megaplex™ RT Primers, Human Pool Set v2.0 for microRNA reverse transcription. All sample concentrations were adjusted to the lowest limiting sample (15 ng/ul). In order to increase sensitivity, the optional preamplification step was included using Megaplex™ PreAmp Primers, Human Pool Set v2.0 prior to real-time PCR.

miR Reverse Transcription.

For miRNA cDNA synthesis, RNA was reverse transcribed using the miRNA reverse transcription kit (Applied Biosystems) in combination with the stem-loop Megaplex™ Primer Pools for the TaqMan Array Human A and B Card (Applied Biosystems), allowing simultaneous reverse transcription of 676 miRNAs and endogenous controls. Briefly, separately for each card A and B, 3 ul of total RNA (45 ng/ul) was supplemented with Megaplex RT primers (10×), dNTPs (100 mM), MultiScribe Reverse Transcriptase (50 U/µl), RT buffer (10×), $MgCl_2$ (25 mM), and RNase inhibitor (20 U/ul) in a total reaction volume of 7.5 µl. After a 5 minute incubation on ice, the following RT protocol was used: 40 cycles of 16 C for 2 min, 42 C for 10 min and 50 C for 1 s, followed by a final reverse transcriptase inactivation at 85 C for 5 min).

Preamplification of cDNA.

For each card A and B, Megaplex RT product (2.5 µl) was preamplified using Applied Biosystems' TaqMan PreAmp Master Mix (10×) and Megaplex PreAmp Primers (10×) in a 25 µl PreAmp reaction. The preamplification cycling conditions were as follows: 95 C for 10 min, 55 C for 2 min and 72 C for 2 min followed by 12 cycles of 95 C for 15 s and 60 C for 4 min.

Real-Time qPCR.

For each card A and B, the 25 ul PreAmp reaction was diluted with 75 µl of 0.1×TE pH8.0. PCR amplification reactions were prepared in a total volume of 900 µl for each card, containing 450 µl of TaqMan 2× Universal PCR Master Mix, w/o UNG (Applied Biosystems), 441 of Nuclease-free water, and 9 µl diluted PreAmp product. 100 µl of the PCR reaction mix were loaded into each port of card A and B, respectively. Card A and B were centrifuged in special buckets. Two one-minute spins at 1200 rpm were performed. The arrays A and B were sealed and loaded separately on ABI Prism 7900HT Sequence detection system (Applied Biosystems). Cycling conditions were as follows: 50 C for 2 min, 94.5 C for 10 min followed by 40 cycles of 97 C for 30 s and 59.7 C for 1 min. All PCR reactions were performed on the ABI Prism 7900HT Sequence detection system (Applied Biosystems). Raw Ct values were calculated using the SDS software v.2.1 using automatic baseline settings and a threshold of 0.2.

TaqMan® Array Human MicroRNA Set Cards v2.0 Data Validation.

Differentially expressed miRs were validated on the validation set using the TaqMan MicroRNA Assays. The single tube TaqMan MicroRNA Assays were used to detect and quantify mature microRNAs on Applied Biosystems Real-Time PCR instruments. All reagents, primers and probes were obtained from Applied Biosystems (Applied Biosystems, Foster City, Calif.). Normalization was performed with RNU44 and RNU48). Reverse Transcriptase Reactions and Real-Time PCR were performed according to the manufacturers. All RT reactions, including no-template controls and RT minus controls, were run in a GeneAmp PCR 9700 Thermocycler (Applied Biosystems). Gene expression levels were quantified using the ABI Prism 7900HT Sequence detection system (Applied Biosystems). Comparative real-time PCR was performed in triplicate, including no-template controls. Relative expression was calculated using the comparative $C_t$ method.

Real Time PCR for Mature miRNAs in Cells and in CM.

Total RNA was isolated with Trizol (Invitrogen) from cells and with High Pure miRNA Isolation Kit (Roche) in accordance with manufacturer's instructions for liquid samples. Mature miRs were assessed by the single-tube TaqMan MicroRNA Assay. miR expression was normalized in cells to RNU44 and RNU48. All retrotranscriptase (RT) reactions, including no-template controls and RT minus controls, were run in a GeneAmp PCR 9600 Thermocycler (Applied Biosystems).

Each sample was tested in triplicate unless otherwise specified. MicroRNAs from medium samples were isolated. After DNase treatment (Ambion), RNA concentrations were determined with a NanoDrop (Thermo Scientific). In serum samples were normalized to U6snRNA (Applied Biosystems), as indicated. Since U6 is inconsistent, the expression levels of target miRNAs were directly normalized to total RNA (the inventors tested before the absence of miR-296-5p and miR-484 in not conditioned medium).

miRNA Overexpression and Western Blot.

For overexpression of miR-296 and miR-484, 100 nM of pre-miR-296, pre-miR-484 and pre-negative control-2 (Ambion) was transfected into HEK293 and HUVE cells using Lipofectamine 2000 (Invitrogen). After 24 hr, cells were harvested and lysed in RIPA buffer containing protease inhibitor cocktail (Roche Diagnostic). Protein concentrations of total cell lysates were measured using a Bradford Protein Assay Dye Reagent Concentrate (Bio-Rad), and 35 µg of cell lysates was resolved on SDS-PAGE gels (Bio-Rad) and transferred to nitrocellulose followed by visualization with ECL detection reagents (Denville Scientific). The following primary antibodies were used: mouse monoclonal anti-Hgs (1:1000, Enzo Life Science), rabbit polyclonal anti-VEGF Receptor 2 (1:1000, Cell Signaling Technology), mouse monoclonal anti-VEGF-B (1:200, Santa Cruz Biotechnology), mouse monoclonal anti-a-Tubulin (1:2000, Sigma).

Luciferase miRNA Target Reporter Assay.

The 3' UTR of the human HGS, and VEGFB genes were PCR amplified using the following primers:

```
HGS Fw
                                          (SEQ ID NO: 1)
5'-GCT CTA GAC CCA GGC CAT GCT CAC GTC CGG AGT

AAC ACT AC-3'
and

HGS Rw
                                          (SEQ ID NO: 2)
5'-GCT CTA GAG AAA TAC ATT TTA TTA TCG CTG TAC

CAT TCT GGG G-3';
```

```
VEGFB Fw
                                        (SEQ ID NO: 3)
5'-TCT AGA GTG CCG GAA GCT GCG AAG GTG-3'
and VEGFB Rw
                                        (SEQ ID NO: 4)
5'-TCT AGA CAG GGT TGG GGG TCA CAG TTC-3'
``` and inserted into pGL3 control vector (Promega) by using Xba1 site immediately downstream from the stop codon of firefly luciferase, giving rise to the p3'UTR-HGS, and p3'UTR-VEGFB plasmids. These constructs were used to generate the p3'-UTRmut-HGS primers:

```
                                        (SEQ ID NO: 5)
Fw: 5'-CAC AAT GAC ACC TCC CCG AGC CTC TGC AGG

GGC CTC TCT CGG CAG CCA CA-3';

(SEQ ID NO: 6)
Rw: 5'-GCT CGG GGA GGT GTC ATT GTG ACA CCA CAG

CCA GCT CAC AGT GCG GCC AG-3',
``` and
p3'-UTRmut-VEGFB plasmids primers:

```
                                        (SEQ ID NO: 7)
Fw: 5'-AGT GGG GGA ACA AAG AGG TAA AAA ACA GCC

AAG C-3';

(SEQ ID NO: 8)
Rw: 5'-GCT TGG CTG TTT TTT ACC TCT TTG TTC CCC

CAC T-3'
``` using a QuikChange site-directed mutagenesis kit (Stratagene, San Diego, Calif.).

HEK293 cells were cotransfected with 1 µg of p3'UTR-HGS, or p3'UTR-VEGFB and with p3'UTRmut-HGS, or p3'UTRmut-VEGFB plasmids and 0.1 µg of a *Renilla* luciferase expression construct pRL-TK (Promega) and 100 nM miRNA or control precursors by using Lipofectamine 2000 (Invitrogen). Cells were harvested 24 h post-transfection and assayed with Dual Luciferase Assay (Promega) according to the manufacturer's instructions. Three independent experiments were performed in triplicate.

Immunohistochemistry and assessment of vascular density.

Tumor sections (2 µm thick) were cut and for formalin fixed paraffin embedded sample deparaffinization was achieved trough graded alcohols. Primary antibody against CD34 was applied following manufacturer's instruction. Vascular density (CD34+) was assessed using the Chalkley eyepiece method. Whole tumor sections were scanned at low magnification under a conference microscope by two observers. Three areas with the highest vascular density (vascular hot-spots) were identified. At high magnification (×400) a 25-point Chalkley-Eyepiece graticule was applied to each hot-spot and oriented to permit the maximum number of points to hit on or within blood vessels. The mean value of the three counts represents the vascular density of the tumor.

Generation of Ovarian Carcinoma Cell Lines Expressing miR-484.

Lentiviruses expressing miR-484 were produced in 293FT cell lines (Invitrogen), by calcium phosphate transfection. To this purpose, the System Biosciences (SBI, USA) miR Precursor Constructs were used, containing dual expression of the specific miR and the copGFP fluorescent marker, for simple identification and monitoring of cells positive for transfection and transduction. Conditioned media containing viruses was harvested 72 hours after transfection, and used to transduce epithelial ovarian cancer cell lines (EOC). In particular, SKOV-3 and MDAH-2774 were transduced with viruses expressing either GFP alone (called hereafter empty vector) or GFP and precursor of miR-484, and then monitored for their fluorescence expression.

In Vitro Susceptibility to Carboplatin+Taxol Treatment of Ovarian Carcinoma Cell Lines Expressing miR-484.

To determine the $IC_{50}$ of EOC cell lines, MDAH 2774, SKOV-3, TOV21G, TOV112D, OVCAR8 and IGROV were plated in 96 wells plates (in sextuplicate) at the density of 1000 cells/well, and 24 hours later treated with increasing doses of carboplatin (CBDCA) (ranging from 1 to 150 mg/ml) or taxol (TAX) (ranging from 1 to 200 nM) for 6 hours in serum free medium. After drugs removal, cells were washed in PBS and incubated in the presence of serum for additionally 4 days. Cells viability was assessed using MTS assay (SIGMA) following manufacturer instructions. The reported $IC_{50}$ values represent the mean of at least 3 independent experiments. For the evaluation of miR-484 effects on in vitro drug sensitivity parental, scramble and miR-484 expressing cells were plated in 96 wells plates (1000 cells/well) and treated with the indicated doses of CBDCA and TAX. Viability was evaluated after 4 days as described above.

Tube Formation Assay on HUVEC Cells Stimulated with Conditioned Media Harvested from Ovarian Carcinoma Cell Lines Expressing miR-484.

Wells from a 48-well plate were filled with 125 ml of matrigel (BD, non growth factor reduced 8-10 ug/ul) and let solidify at 37° C. for 1 hour. HUVEC cells (ATCC, $1\times10^5$) resuspended in 200 ml of medium were then layered onto the matrigel layer and monitored over the time for the formation of tube-like structures. Time-lapse video microscopy (Leica) was used to create a movie of this process, collecting images every 5 minutes for up to 20 hours. Media used to resuspend endothelial cells were 1—complete medium for endothelial cells, used as positive control, 2—Serum reduced medium (2%), used as negative control, 3—conditioned medium (plus 2% serum) from SKOV-7 or MDAH-2774 transduced with scrambled-miR or miR-484.

In Vivo Analysis of Ovarian Carcinoma Cell Lines Expressing miR-484 Growth and Susceptibility to Carboplatin+Taxol Treatment.

Athymic female nude mice (8/group) were subcutaneously injected on both dorsal flanks with 100 ul of PBS containing $1.5\times10^6$ MDAH-2774 cells scrambled-miR (right flank) or miR-484 (left flank).

Same was carried out with SKOV-3, except that $2.2\times10^6$ cells have been injected. When tumor masses became visible treatment with CBDCA (15 mg/kg) and Tax (5 mg/kg) was started. Drugs were delivered diluted in 200 ul of PBS and intraperitoneally injected twice a week, for 4 weeks. Tumor masses were measured with a caliper twice a week, for 4 weeks. Moreover, exploiting the expression of GFP fluorescent marker by the ovarian cancer cells utilized, mice have been anesthetized and tumor masses imaged by the Ivis Lumina, Caliper Lifesciences, once a week, for 4 weeks. Mice were then sacrificed and tumor masses excised and included in OCT for further analyses.

Results miR Expression in Serous Ovarian Carcinomas Related to Chemoresistance.

Figure 1B:
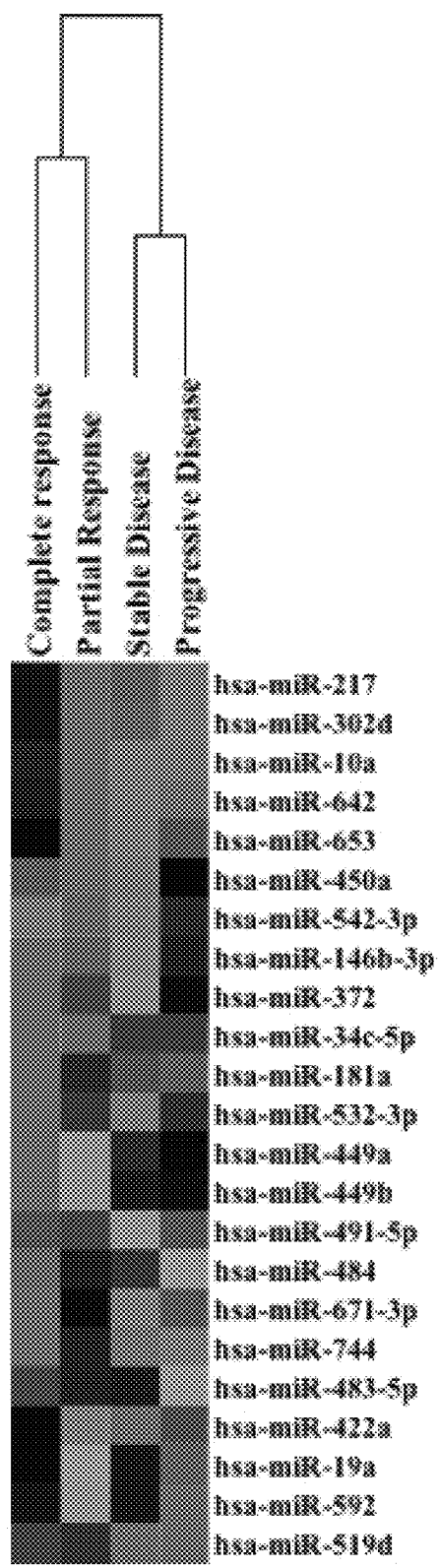

To determine whether miRs are useful to predict serous ovarian carcinoma (EOC) chemoresistance, the expression of 676 miRs was analyzed. As shown in FIG. 1A, a response signature with 23 differentially expressed miRs capable to discriminate among the 4 different groups was identified. Cluster analysis of the centroids (FIG. 1B) shows that the EOC samples can be grouped in two major classes: complete and partial responders, further labeled as responders on one side and stable and progressive disease, labeled non-responders, on the other. These two classes are useful to further refine the response signature and define 12 miRNAs (FIG. 1C). Also, 112 EOC samples from a second patient cohort were used to validate the response miRNAs (FIG. 1D). Out of the 12 miRs initially identified, three miRs are shown to be down-regulated in non-responder tumors: miR-484 (p-value=0.0007), miR-642 (p-value=0.041) and miR-217 (p-value=0.046).

miR-484 Expression does not Alter In Vitro Sensitivity to Carboplatin and Taxol.

Figures 6A, 6B:
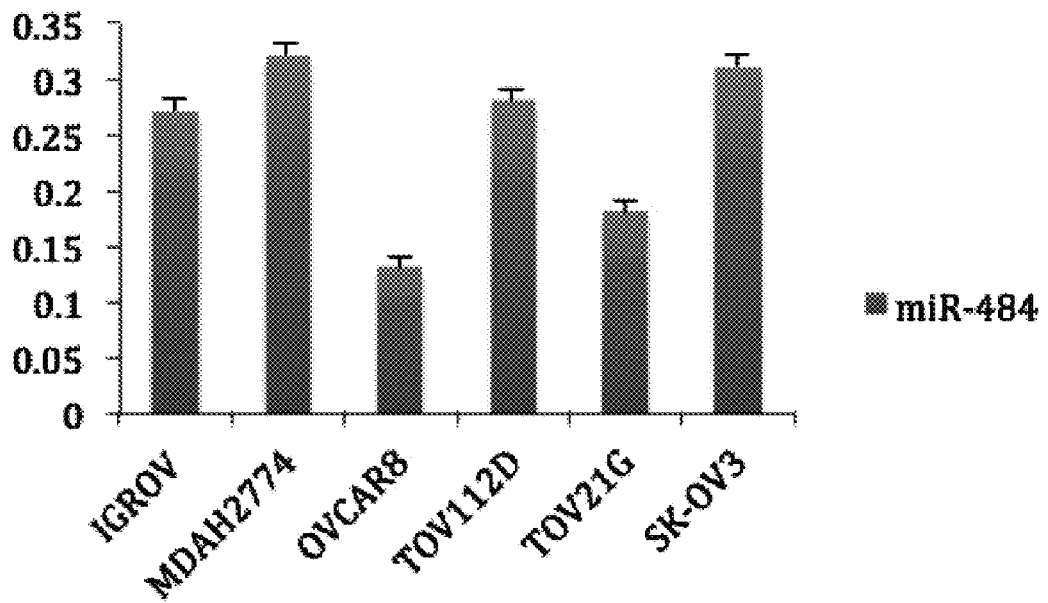
FIGS. 6A-6D.
Figure 6C:
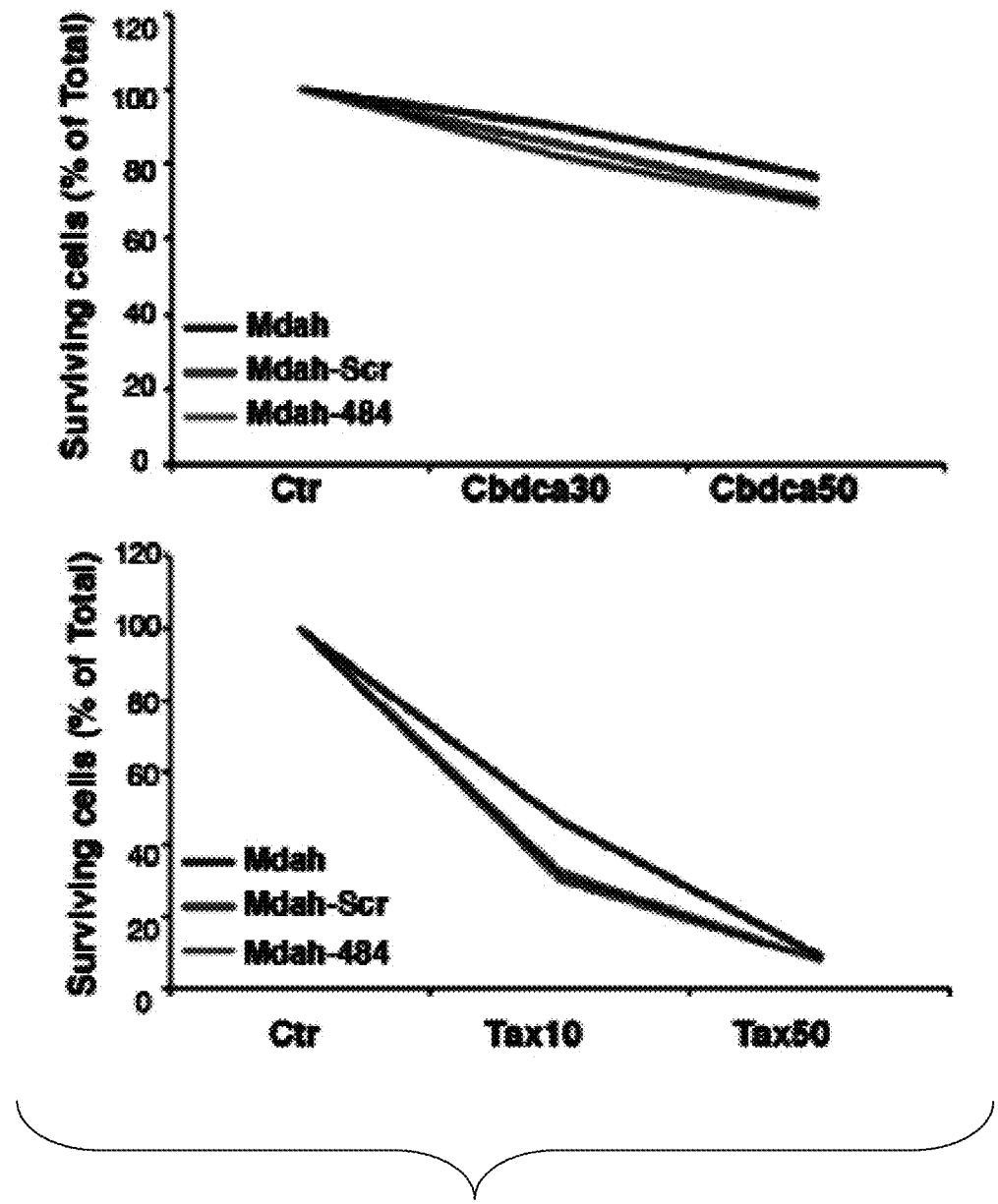
Figure 6D:
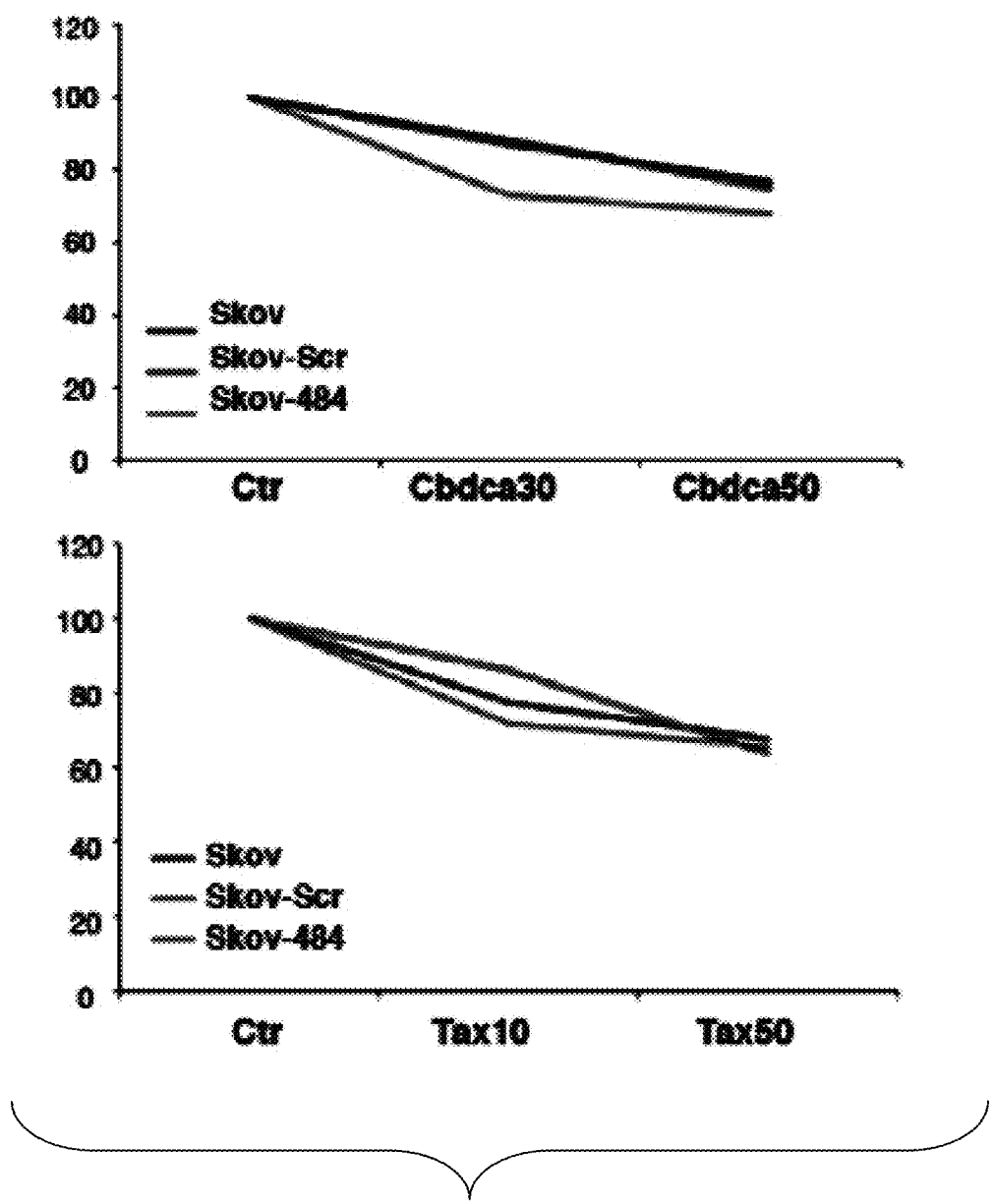
Figure 10B:
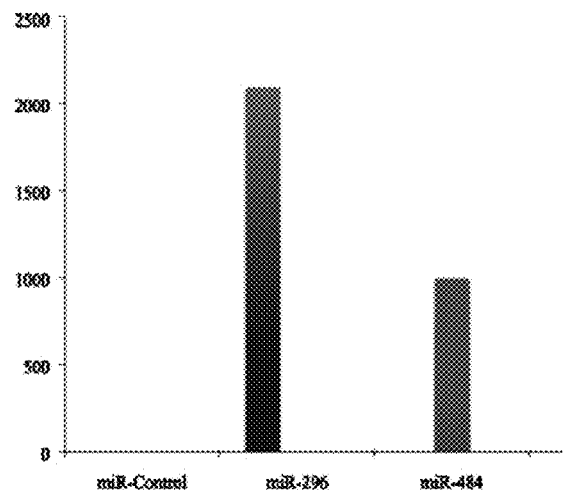
Figure 10C:
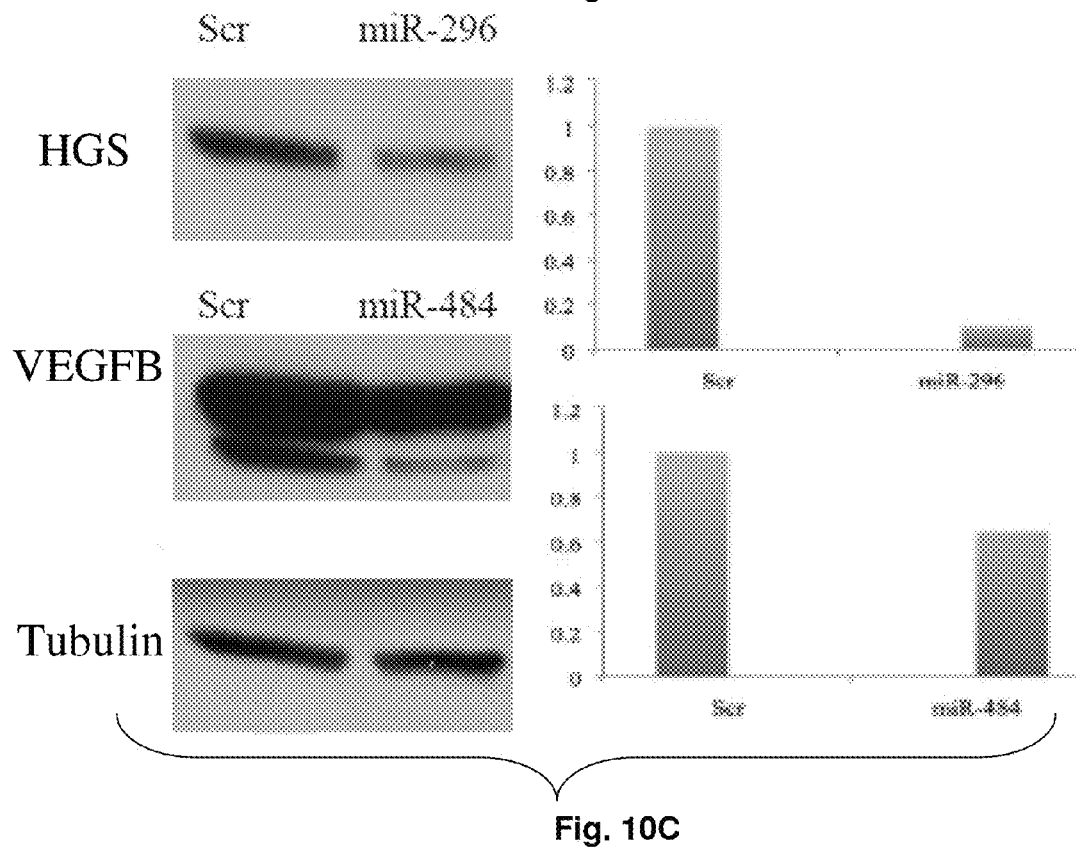
Figure 10D:
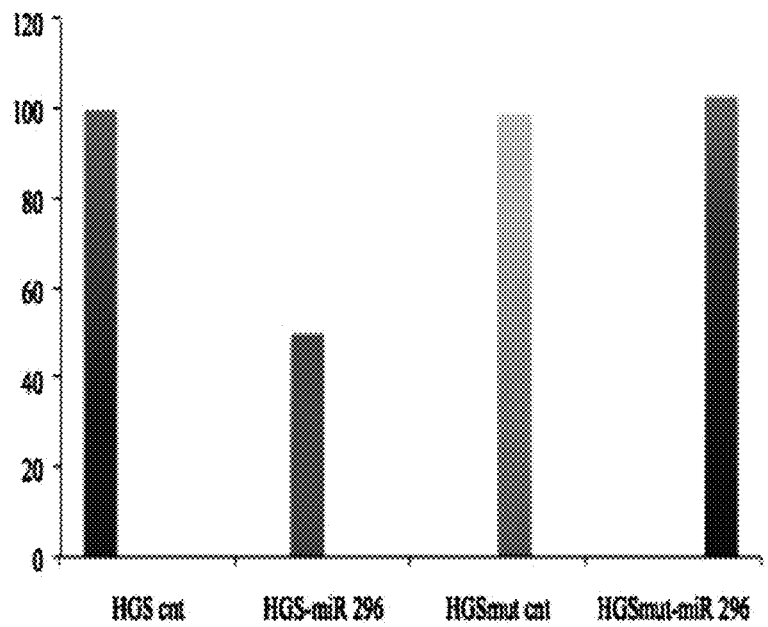
Figure 10E:
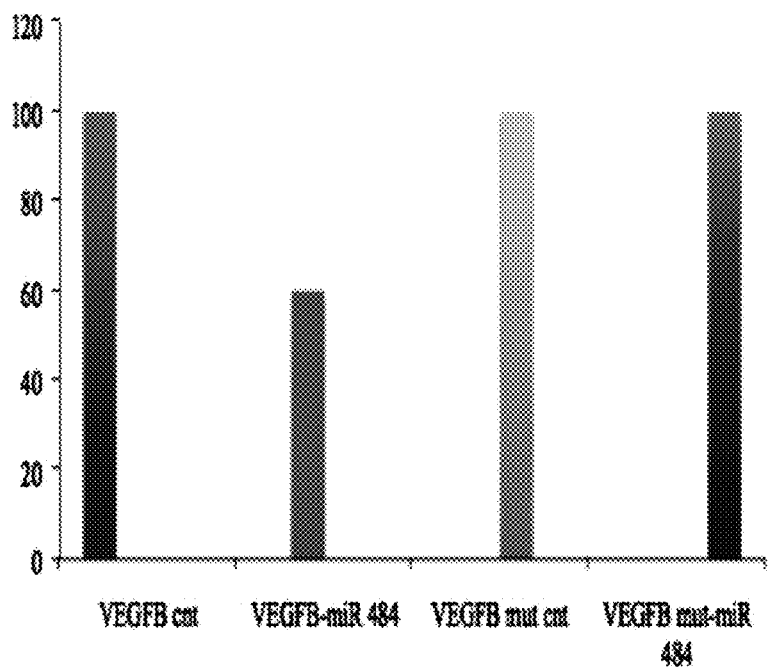
FIG. 10E. Luciferase assay vectors containing the 3'UTR of the wild-type VEGFB mRNA transfected with scramble miR (VEGFB cnt) or with miR-484 (VEGFB-miR 484) and vectors containing the mutated miR 484 binding site transfected with scramble miR (VEGFBmut cnt) or with miR-484 (VEGFBmut-miR 484).

The expression levels of miR-484 were evaluated in 6 different epithelial ovarian carcinoma cell lines (FIGS. 6A-6B). Despite treating the cells for 2 or 4 hours with increasing concentration of carboplatin (CBDCA) and taxol (Tax), their $IC_{50}$ was not related to the endogenous levels of miR-484, as evaluated 4 days later by MTS assay. Moreover, overexpression of miR-484 in both MDAH-2274 and SK-OV3 cell lines did not significantly affect their in vitro sensitivity to CBDCA and Tax (FIGS. 6C and 6D).

Role of miR-484 in the Acquisition of Chemoresistance.

Figure 2A:
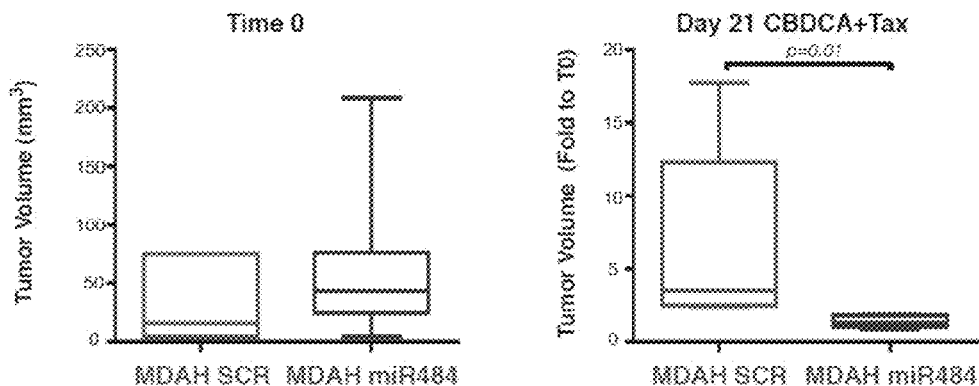
FIGS. 2A-2D.

Since levels of 484 were very similar among cell lines, MDAH-2774 and SK-OV3 cells over-expressing either control-miR (scramble) or miR-484 were sued to recapitulate in vivo the non-responder phenotype and to determine whether miR influence the chemosensitivity of ovarian cancer in a context-dependent manner. Lentiviral vectors encoding also the EGFP— protein were used in order to follow tumor growth in vivo. Cells ($1.5 \times 10^6$) were inoculated in nude mice subcutaneously into the left (miR-484-MDAH-2774) and right flank (EGFP-MDAH-2774) and allowed to grow for 15 days. At this time point in 6/8 mice the tumor volume formed by miR-484 expressing cells was larger than that observed in control EGFP-expressing cells, demonstrating that the growth of the primary tumor was not affected by the expression of the miR (FIG. 2A).

After CBDCA and Tax treatment, one mouse did not respond and was excluded from the study. Analysis of the other 7 mice demonstrated that control tumors increased their size about 6-fold with respect to day 0 at the end of the treatment (range 2.3-17.7). In the same mice miR-484 expressing tumors increased only 1.3 fold (range 0.8-1.8) demonstrating to be much more sensitive to the drugs than the controls (FIG. 2A).

Figure 2B:
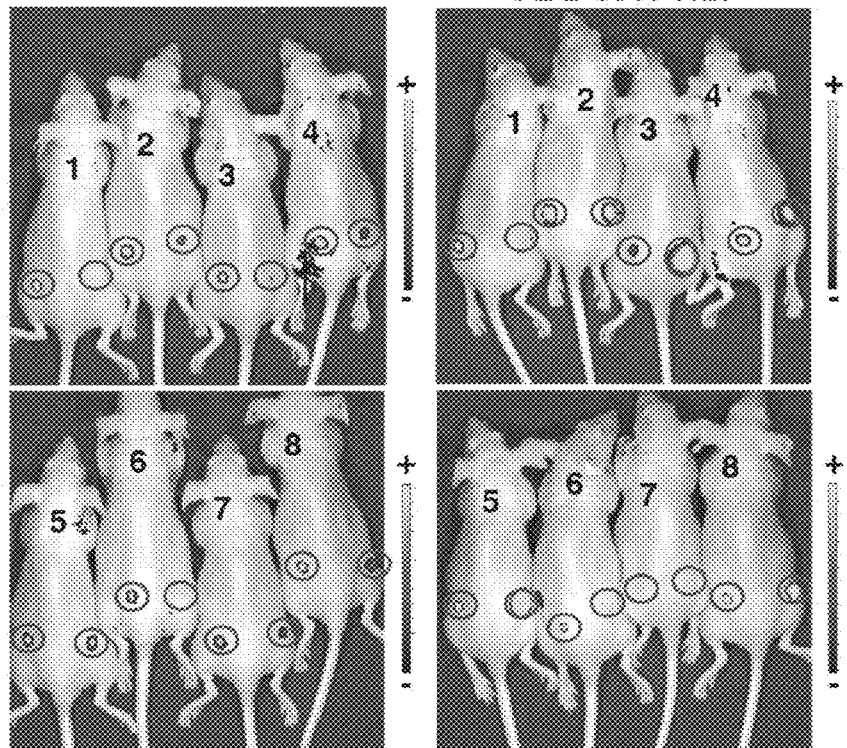
Figure 2C:
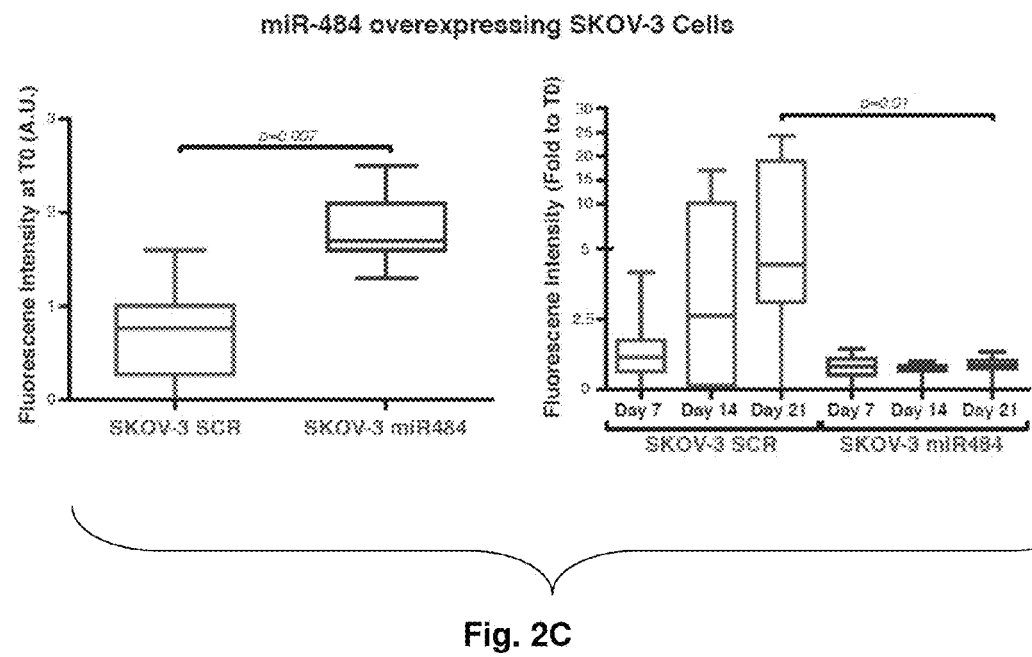
Figure 2D:
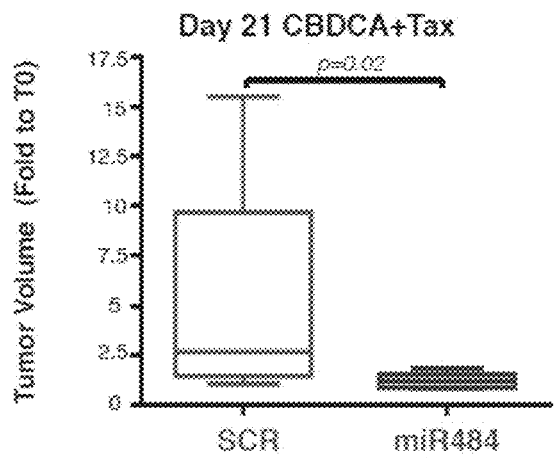

Using an in vivo imaging system able to detect the EGFP fluorescence, the analysis of SK-OV3 cells confirmed that the expression of miR-484 did not affect the growth of the primary tumor but significantly increased the sensitivity to treatment (FIGS. 2B and 2C).

Figure 3A:
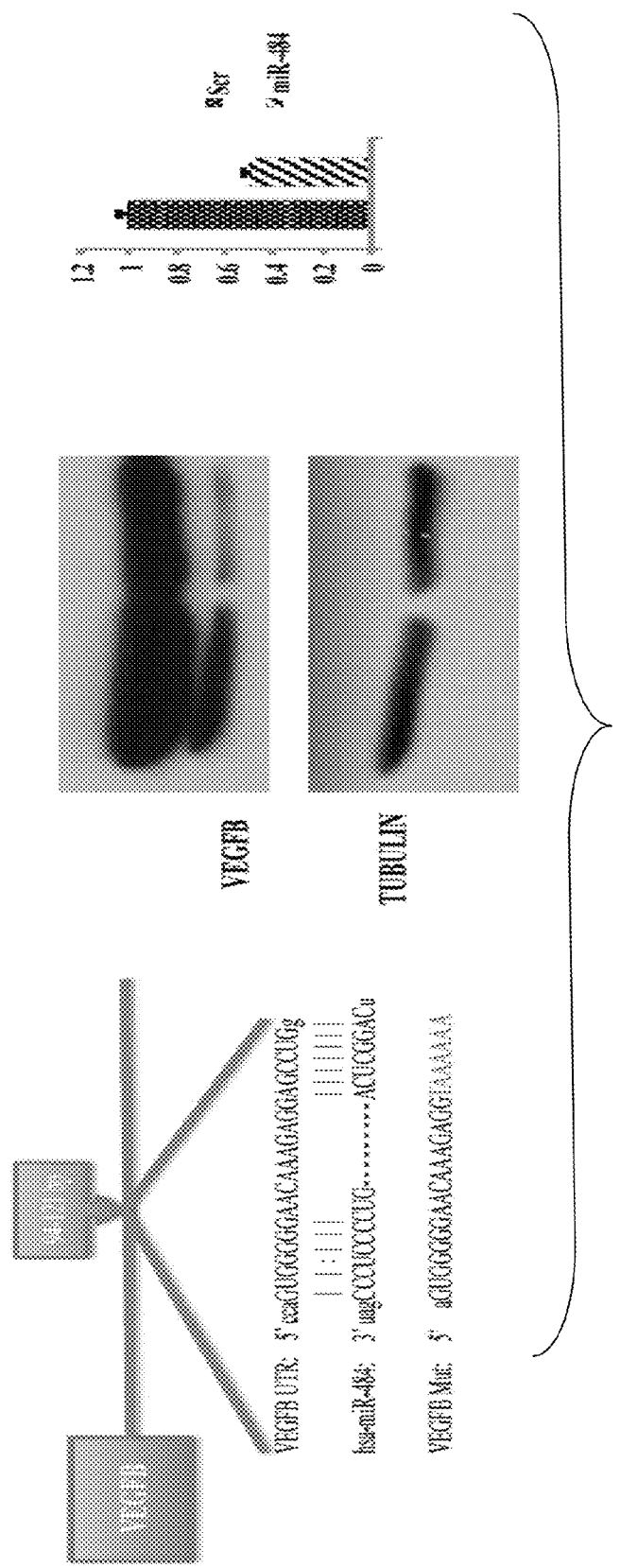
Figure 3B:
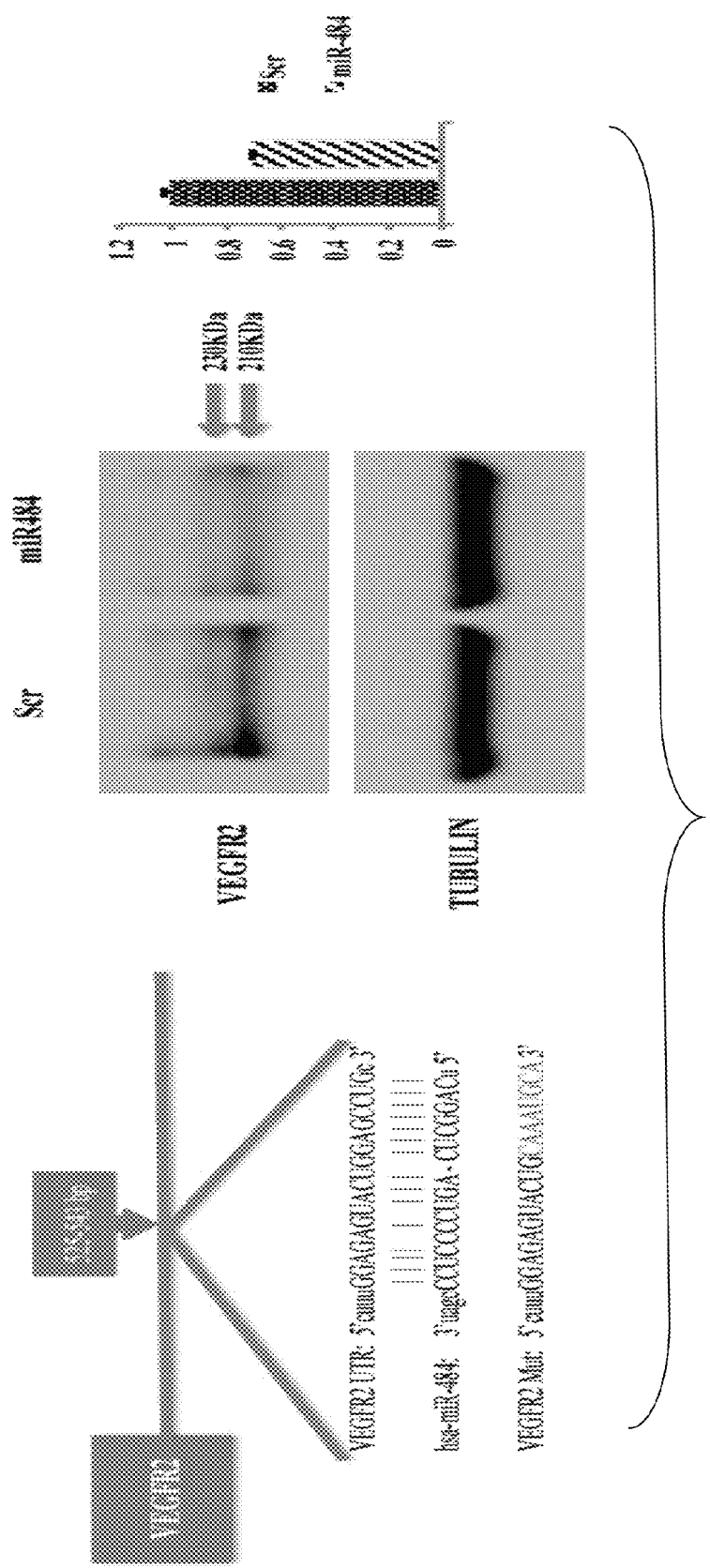

MDAH-2774 cells, which grew more rapidly in nude mice than SKOV-3, were used to examine whether in vivo administration of the miR could alter the sensitivity of EOC to CBDCA+Tax treatment. Parental MDAH-2774 cells were allowed to grow for 2 weeks in the flanks of nude mice, and then injected with lentivirus expressing EGFP-control miR in the right flank and with lentivirus expressing EGFP-miR-484 in the left flank. Two days later mice were treated biweekly for 3 weeks with CBDCA+Tax and the intratumoral injection of virus was repeated after one week. After 21 days tumor growth was evaluated. Strikingly, in 6/6 cases miF-484 increased drug sensitivity, demonstrating that its expression is able to modulate resistance to CDBCA and Tax in epithelial ovarian cancer in vivo (FIGS. 2A-2D).

miR-484 Regulates the Expression of Angiogenic Factors.

miR-484 is involved in the regulation of angiogenic factors. miR-484 targets the vascular endothelial growth factor B (VEGFB), which is able to directly stimulate endothelial-cell growth and migration and the vascular endothelial growth factor 2 (VEGFR2/KDR) that is implicated in all aspects of normal and pathological vascular-endothelial-cell biology. Luciferase and western blot analyses confirmed that miR-484 modulated the endogenous levels of VEGFB and VEGFR2, (FIGS. 3A-3C).

Figure 4C:
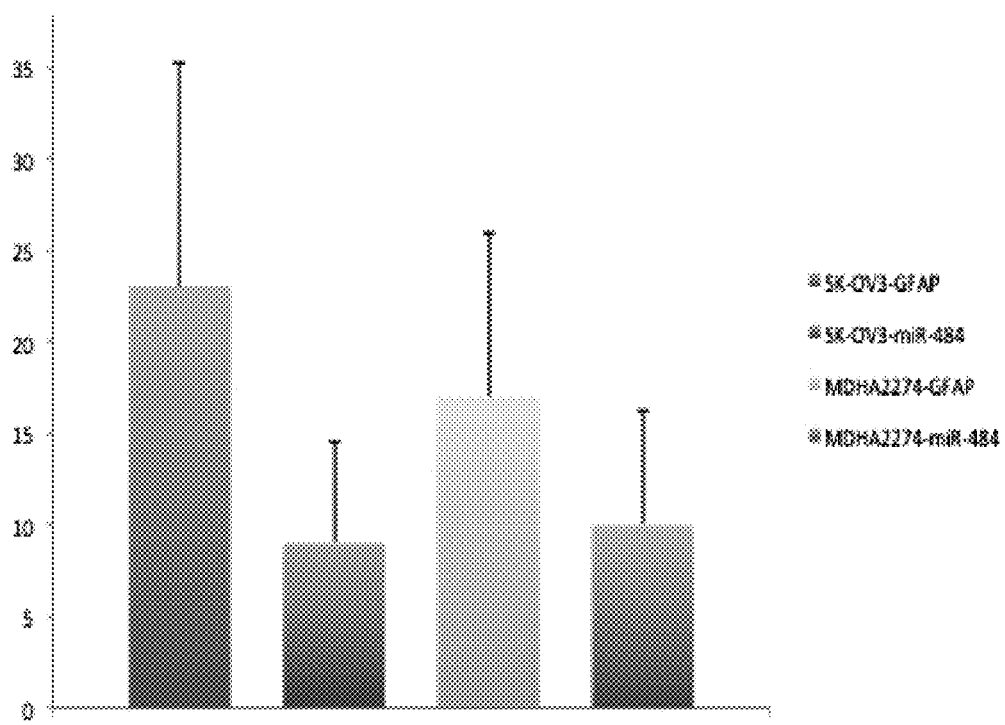

Vascular density was assessed using anti-CD34 antibody on 30 cases of human serous ovarian carcinoma (15 responders/15 non-responders) and 28 cases of mice xenograft tumors [14 from Sk-ov3 and 14 from MDAH-2774 (7 transduced with miR-484 and 7 with GFP)] and evaluated through the Chalkley eyepiece method. In human tumors the mean microvessel density was 30±1.17 (range 9-54) for responders and 68±1.6 (range 15-114) for non-responders (P=0.0000002), in mice it was 9±5.5 (range 1-18) for SK-OV3-miR 484, 23±12 (range 5-37) for SK-OV3-EGFP (p=0.0004) and 10±6.2 (range 4-22) for MDAH-2774-miR 484, 17±8.9 (range 5-28) for MDAH-2774-EGFP (p=0.0009) (FIGS. 4A-4C).

Figure 4D:
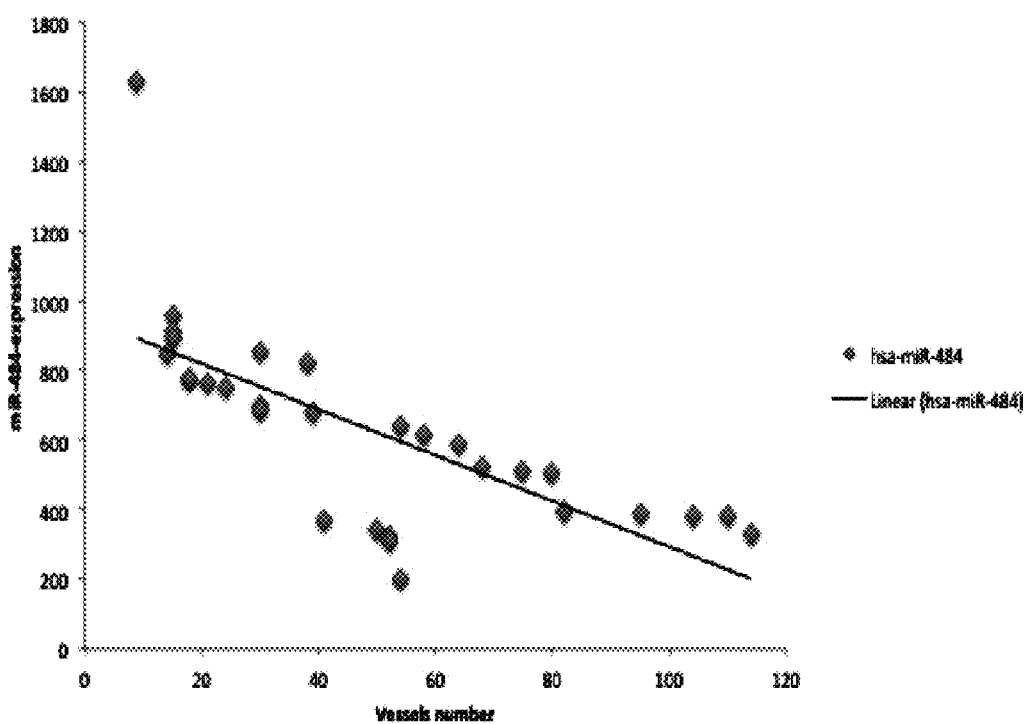

A spearman rank correlation test shows the strong relationship between vessels number and miR expression (r=−0.8, p=1.56E-07), showing that the sensitivity of these tumors is due to their microvessel asset driven by miR regulation (FIG. 4D).

To confirm, mir-484-mediated modulation of the vessel asset, MDAH-2774 or SK– OV3 cell lines stably transduced with miR-484 or scr-vector were analyzed by Western Blot for VEGFB expression. HUVEC cells were cultured in conditioned medium (CM) obtained from the transfected cells. Video time-lapse microscopy demonstrated that CM from scr-MDAH-2774 or SK-OV3 cells was able to induce the formation of tube like structures when HUVEC cells were cultured for 6 hours on 3D matrigel. This effect was impaired when CM from MDAH-2774 or SK-OV3 overexpressing miR-484 was used and abolished when cells were cultured in the presence of CM for 20 hrs (FIG. 7).

Overall, these data confirm that miR-484 expression in EOC cells is able to affect the ability of endothelial cells to form and sustain the formation of vascular like structures. While not wishing to be bound by theory, the inventors herein now believe that miR-484 regulation of VEGFB is possible on the neoplastic cells, but in order to regulate VEGFR2, the miR must exert its action directly on the tumor associated endothelial cells.

Figure 5A:
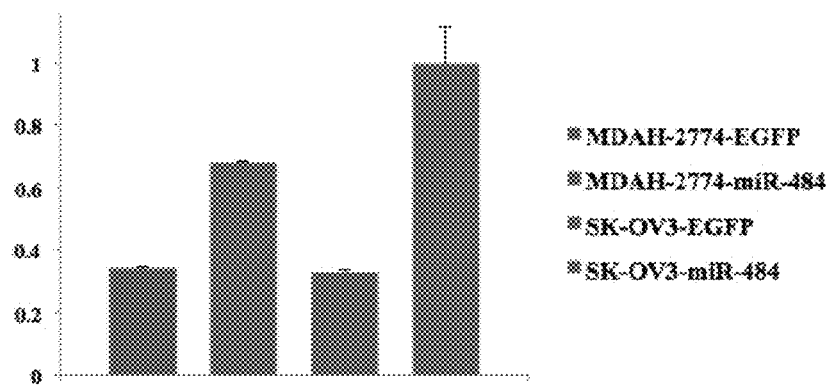
FIGS. 5A-5E.
Figure 5B:
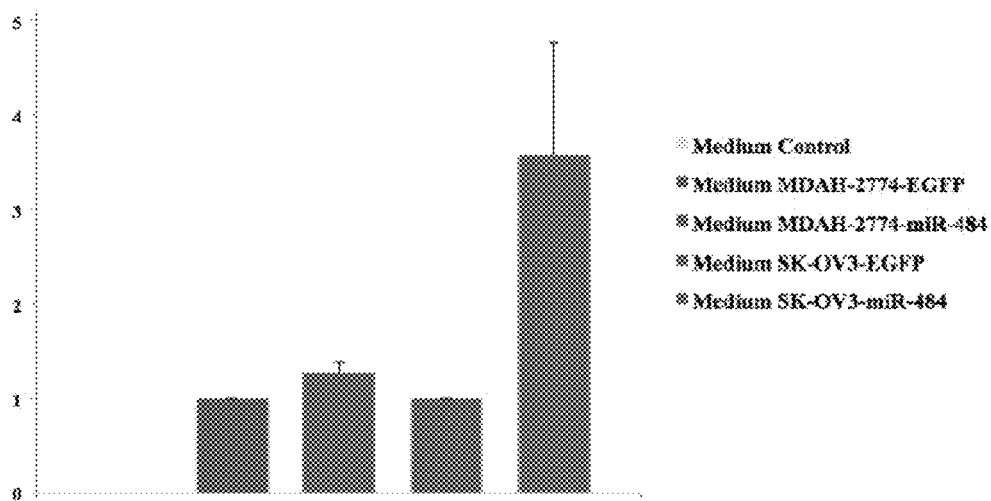
Figure 5C:
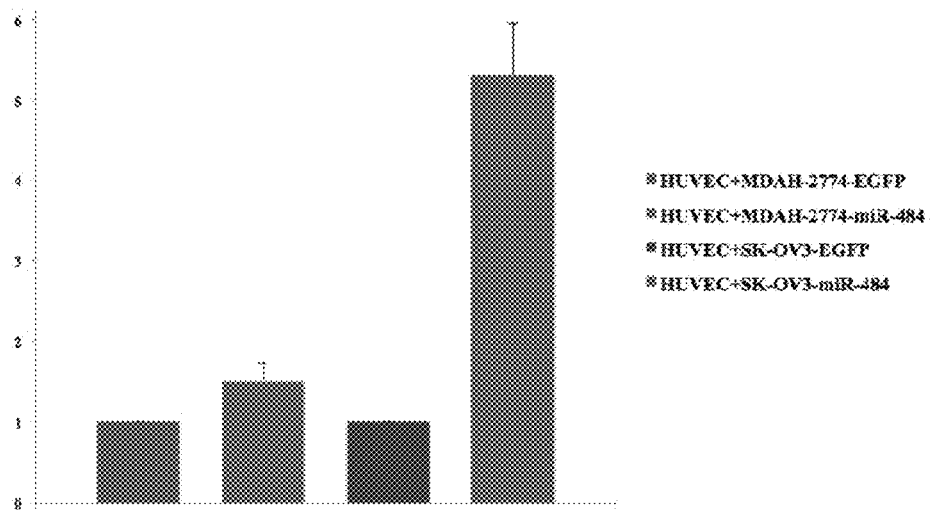
Figure 5D:
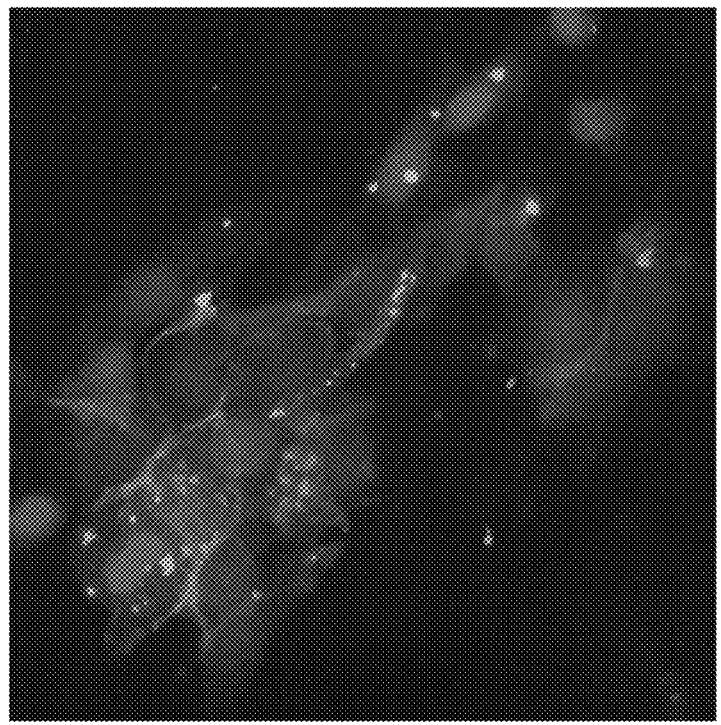

To determine whether miR-484 produced by EOC is released into the local microenvironment and then enters the endothelial cells where it can reach its target, HUVEC and ovarian cancer cells derived cell lines over-expressing miR-484-EGFP or scrambled miR-EGFP were co-cultured. Stable transfection of miR-484-EGFP in MDAH-2774 and SK-OV3 resulted in at least a 2-fold increase of its expression over controls (FIG. 5A).

miR-484 increased in the CM of ovarian cancer cells derived cell lines stable transfected (FIG. 5B). Levels of miR-484 increased from 0.2 to 5-fold with respect to control in HUVEC cells cultured in the presence of miR-484 overexpressing cell lines (FIG. 5C). The data demonstrate that direct contact between ovarian carcinoma derived cell lines and HUVEC cells is not necessary since the co-culture experiments were done by plating the cancer cells on the well and the HUVEC on the transwell (or vice versa with no significant differences). Collectively these data demonstrate that miR-484 is secreted by the neoplastic cells in the local microenvironment and enters HUVEC cells within 24 hours (FIG. 5D).

Figure 5E:
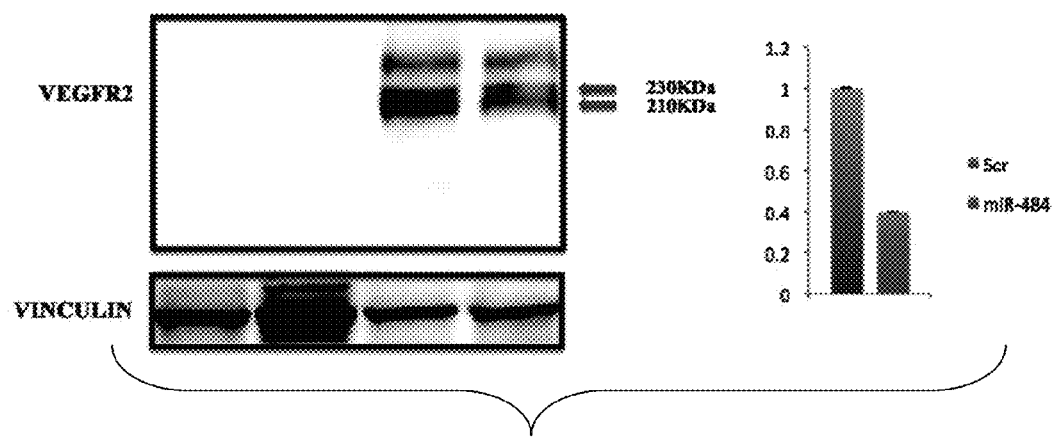

Moreover, when HUVEC were co-cultured with control and miR-484 over-expressing SK-OV3 for 24 hours, only the latter were able to significantly decrease the expression of VEGFR2 on endothelial cells (FIG. 5E).

Ovarian cancer cells, overexpressing miR-484, are less able to stimulate endothelial cell reorganization in vitro and neovascularization in mice. Cooperation between VEGFR1 and 2 signaling is necessary for ovarian cancer growth and drug sensitivity.

Example 2 miR Expression Signature in Responder Vs. Refractory Ovarian Carcinomas

To investigate whether miRs are predictive of ovarian carcinoma chemoresistance, the expression of 676 miRs in the training set were analyzed. Out of the 381 target miRs in Card A and 295 target miRs in Card B, 364 (96%) and 240 (81%) were amplified in at least one of the samples respectively. Only 17 from Card A and 55 from Card B were undetermined (Ct=40) across all samples. As shown in FIG. 9, 16 differentially expressed miRs capable to discriminate R from NR serous carcinomas were identified. No miRs were found statistically significant with respect to surgery outcome and/or tumor grade (data not shown). Differentially expressed miRs were then validated on the validation set. Out of the 16 miRs initially identified, three miRs are differentially expressed in the two groups, with two being down-regulated (miR-296-5p and miR-518e) and one being up-regulated (miR-484) in R tumors (FIG. 9). These three miRs are able and sufficient to discriminate between the two groups.

miR-296 and miR-484 Expression does not Alter In Vitro Sensitivity to CBDCA and Tax.

To obtain determine the role of miRs in the development of drug resistance, the expression levels of miR-484 and miR-296 were evaluated in 6 different epithelial ovarian carcinoma cell lines (EOC). While miR-484 was readily detectable in all cell lines, miR-296 was barely expressed in MDAH-2774 and TOV-112D. Despite treating the cells for 2 or 4 hours with increasing concentration of CBDCA and Tax, their $IC_{50}$ was not related to the endogenous levels of miR-484 or 296, as evaluated 4 days later by MTS assay. Moreover, overexpression of miR-484 and 296 in both MDAH-2274 and SKOV-3 cell lines did not significantly affect their in vitro sensitivity to CBDCA and Tax.

Role of miR-484 in the Acquisition of Chemoresistance.

Since miR-296 was expressed at very low-levels in the EOC, and levels of miR-484 were very similar among cell lines, the MDAH-2774 and SKOV-3 cells over-expressing either control-miR (scramble) or miR-484 were used to recapitulate in vivo the R phenotype and to determine whether miRs influence the chemosensitivity of ovarian cancer in a context-dependent manner. Lentiviral vectors encoding also the EGFP— protein were used in order to follow tumor growth in vivo. Cells ($1.5 \times 10^6$) were inoculated in nude mice subcutaneously into the left (miR-484-MDAH-2774) and right flank (EGFP-MDAH-2774) and allowed to grow for 15 days. At this time point in 6/8 mice the tumor volume formed by miR-484 expressing cells was larger than that observed in control EGFP-expressing cells, demonstrating that the growth of the primary tumor was not affected by the expression of the miR.

After CBDCA and Tax treatment, one mouse did not respond and was excluded from the study. Analysis of the other 7 mice demonstrated that control tumors increased their size about 6-fold with respect to day 0 at the end of the treatment (range 2.3-17.7). In the same mice miR-484 expressing tumors increased only 1.3 fold (range 0.8-1.8) demonstrating to be much more sensitive to the drugs than the controls. Using an in vivo imaging system able to detect the EGFP fluorescence, the analysis of SKOV-3 cells confirmed that the expression of miR-484 did not affect the growth of the primary tumor but significantly increased the sensitivity to treatment.

MDAH-2774 cells, which grew more rapidly in nude mice than SKOV-3, were used to determine whether in vivo administration of the miR could alter the sensitivity of EOC to CBDCA+Tax treatment. Parental MDAH-2774 cells were allowed to grow for 2 weeks in the flanks of nude mice, and then injected with lentivirus expressing EGFP-control miR in the right flank and with lentivirus expressing EGFP-miR-484 in the left flank. Two days later, mice were treated biweekly for 3 weeks with CBDCA+Tax and the intratumoral injection of virus was repeated after one week. After 21 days tumor growth was evaluated. Strikingly, in 6/6 cases mir-484 increased drug sensitivity, demonstrating that its expression is able to modulate resistance to CDBCA and Tax in epithelial ovarian cancer in vivo.

miR-484 and miR-296 Regulate the Expression of Angiogenic Factors.

miR-484 (and to a lesser extent miR-296) have a role in the chemosensitivity of EOC cells in vivo but not in vitro, showing that they act on the tumor microenvironment rather than in a cell autonomous manner. Both miRs are involved in the regulation of angiogenic factors. Luciferase and western blot analyses confirmed that miR-296 and miR-484 modulated the endogenous levels of HGS and VEGFB, respectively (FIGS. 10B-10E).

Figure 11A:
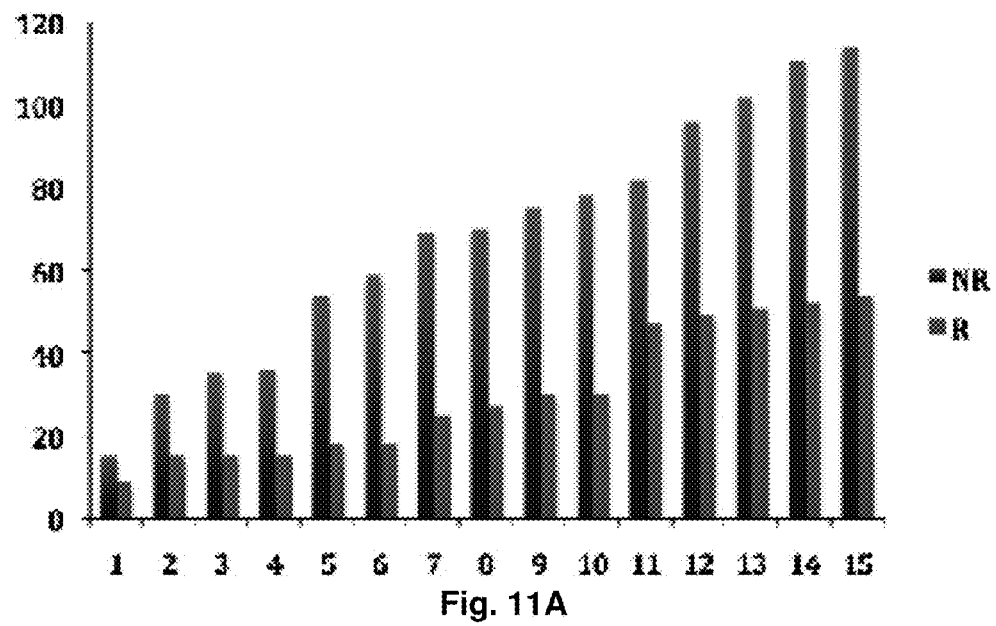
FIGS. 11A-11C.
Figure 11B:
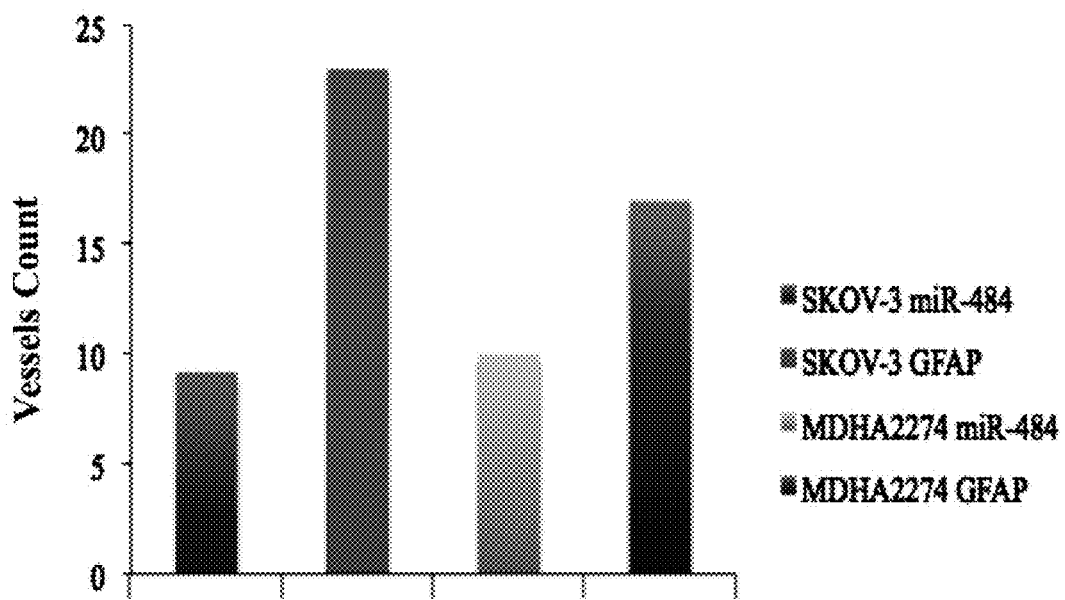
Figure 11C:
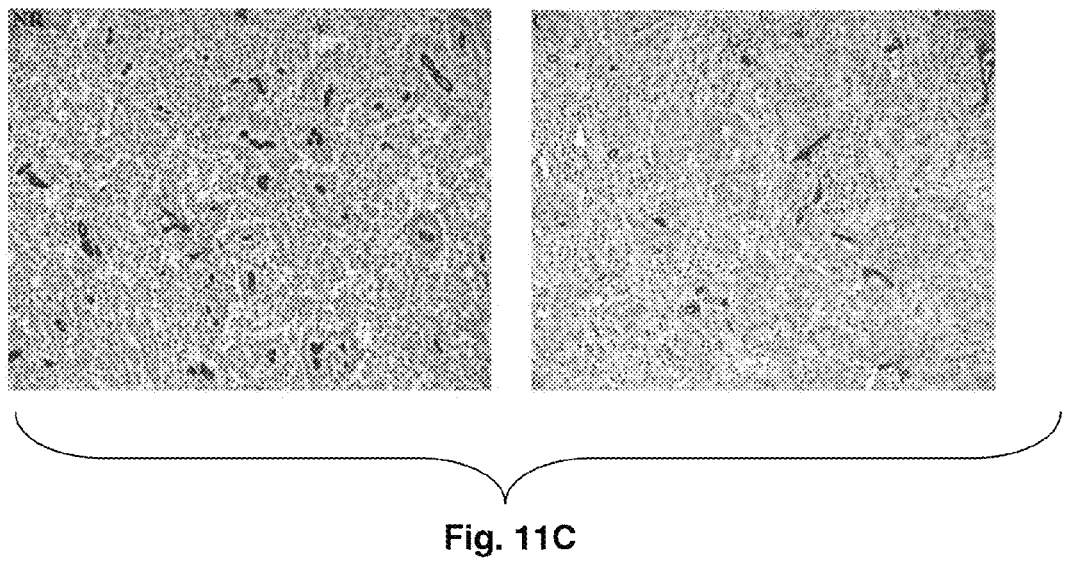

Vascular density was assessed using anti-CD34 antibody on 30 cases of human serous ovarian carcinoma (15 R/15 NR) and 28 cases of mice xenograft tumors [14 from Skov-3 and 14 from MDAH-2774 (7 transduced with miR-484 and 7 with GFP)] and evaluated through the Chalkley eyepiece method. In human tumors the mean microvessel density was 30 (range 9-54) for R and 68 (range 15-114) for NR (P=0.0000002), in mice it was 9 (range 1-18) for SKOV-3-miR 484, 23 (range 5-37) for SKOV-3-EGFP (p=0.04) and 10 (range 4-22) for MDAH-2774-miR 484, 17 (range 5-28) for MDAH-2774-EGFP (p=0.01) (FIGS. 11A-11C), demonstrating that the sensitivity of these tumors is due to their microvessel asset driven by miR regulation. In order to confirm miR-484-mediated modulation of the vessel asset, MDAH-2774 or SKOV-3 cell lines stably transduced with miR-484 or scr-vector were analyzed by western blot for VEGFB expression, that was down-regulated (data not shown). HUVEC cells where cultured in conditioned medium (CM) obtained from the transfected cells. Video time-lapse microscopy demonstrated that CM from scr-MDAH-2774 or SKOV-3 (data not shown) cells was able to induce the formation of tube like structures when HUVEC cells were cultured for 6 hours on 3D matrigel. This effect was impaired when CM from MDAH-2774 or SKOV-3 overexpressing miR-484 was used and abolished when cells were cultured in the presence of CM for 20 hrs. Overall, these data confirm that miR-484 expression in EOC cells is able to affect the ability of endothelial cells to form and sustain the formation of vascular like structures.

While miR-484 regulates the expression of VEGFB and consequently the amount of ligand secreted in the tumor microenvironment, miR-296, regulating the levels of the receptors must exert its action directly on the tumor associated endothelial cells. While not wishing to be bound by theory, the inventors herein now believe that miR-296 produced by EOC cells is released into the local microenvironment, especially following drug treatment, and then enters the endothelial cells where it targets the HGS, eventually modulating the VEGFR2 signaling. To confirm, HUVEC and EOC cells over-expressing miR-296-EGFP or scrambled miR-EGFP were co-cultured. Stable transfection of miR-296-EGFP in different EOC cells resulted in at least a 2-fold increase of its expression over controls. miR-296 was found in the CM of EOC cells over-expressing the miRs. Levels of miR 296 increased from 1 to 11-fold with respect to control in HUVEC cells cultured in the presence of miR 296 over-expressing EOC cells. These data demonstrate that direct contact between EOC and HUVEC cells is not necessary since the co-culture experiments were done by plating the EOC on the well and the HUVEC on the transwell (or vice versa with no significant differences). Collectively these data demonstrate that miR-296 is secreted by EOC cells in the local microenvironment and enters HUVEC cells within 24 hours. Moreover, when HUVEC were co-cultured with control and miR-296 over-expressing EOC cells on coverslips for 24 hours, only the latter were able to significantly increase the expression of VEGFR2 on endothelial cells. This was consistently reproduced in all cells tested.

Example 3

Kits

Any of the compositions described herein may be comprised in a kit. In a non-limiting example, reagents for isolating miRNA, labeling miRNA, and/or evaluating a miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the miRs described herein.

The components of the kits may be packaged either in aqueous media or in lyophilized form. The container device of the kits will generally include at least one vial, test tube, flask, bottle, syringe or other container device, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a device for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container device. The kits may also include components that facilitate isolation of the labeled miRNA. The kit may also include components that preserve or maintain the miRNA or that protect against its degradation. The components may be RNAse-free or protect against RNAses.

Also, the kits can generally comprise, in suitable device, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of a miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated. The kits can include a miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis. Also, the sample can be blood or tissue.

In one embodiment, the kit for the characterization of ovarian cancer includes at least one detection probe for miR-484, miR-642 and/or miR-217. In certain embodiments, the kit is in the form of, or comprises, an oligonucleotide array.

Also provided herein is a kit for diagnosing ovarian cancer and/or predicting chemotherapeutic resistance in an ovarian cancer, comprising:

a) a miR-484 quantitative kit including pairs of nucleotide primers and detection reagents for determining expression levels of miR-484, b) a miR-642 quantitative kit including pairs of nucleotide primers and detection reagents for determining expression levels of miR-642, c) a miR-217 quantitative kit including pairs of nucleotide primers and detection reagents for determining expression levels of miR-217, and d) a programmable object, which is provided for inputting the expression levels of the miR-484, the miR-642 and the miR-217 to perform the method for in vitro diagnosis of ovarian cancer.

Also provided herein is the use of the miR-484, miR-642 and/or miR-217 as diagnostic biomarkers in a kit. The expression levels of these diagnostic biomarkers can be detected in a biological sample from a patient using a capture agent, and then compared to the reference values for the same biomarkers in healthy subjects. The reference values to which the detected values are compared can be those established for patients positive for the disease, for patients negative for the disease, or both. A change in the expression level of the at least one, two and/or all of the biomarkers in a biological sample from the patient relative to the reference values indicates whether the patient is or is not afflicted with the disease.

The capture reagent can be any organic or inorganic chemical, biomolecule, or any fragment, homolog, analog, conjugate, or derivative thereof, that specifically interacts with the diagnostic biomarkers. In certain embodiments, the capture reagent is a protein or antibody that specifically detects the diagnostic biomarkers in a diagnostic biomarker panel. In other embodiments, the capture agent is an oligonucleotide that binds to biomarker oligonucleotide RNA or DNA. In yet certain other embodiments, the capture reagent can be coupled to a solid support. In yet certain embodiments, the biological samples from the patient are tissues, biological fluid, including, but not limited to, whole blood, plasma, serum, tears, saliva, mucous, cerebrospinal fluid, or urine.

Also, in certain embodiments, the method can further comprise a step of detecting an expression level of additional biomarkers in a biological sample from the patient. As used herein, the additional biomarkers include, but are not limited to diagnostic biomarkers, now known or later discovered, in the diagnostic panel, and evaluating changes in the detected expression levels of these biomarkers relative to the reference values for diagnosing a patient as having the disease.

In certain embodiments, the kit can comprise a capture reagent comprising a) one or more detectors specific for at least one diagnostic biomarker, wherein the biomarker is miR-484; b) a detection reagent, and c) instructions for using the kit to diagnose a patient as having ovarian cancer when the expression level of the at least the miR-484 diagnostic biomarker in a patient test sample is lower than the expression levels of the same biomarker in a control subject without ovarian cancer.

The kits can further comprise appropriate positive and negative controls against which a biological sample from a patient can be compared. The kits can further comprise ranges of reference values established for the expression of the disease patients positive for such disease, for patients negative for such disease, or both.

In certain embodiments, the present invention provides a diagnostic method, kit, and device to determine which patients with ovarian cancer are at least likely to respond to chemotherapeutic intervention and/or or adverse outcomes from the disease. A sample from the patient's body is subjected to an assay to detect at least one or more biomarkers associated with ovarian cancer. Each biomarker has a routinely determinable cut-off point that differentiates between ovarian cancer and controls through manual or computer-assisted determination.

In particular embodiments, a combination of biomarkers results greatly increases the accuracy of the diagnosis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example 4

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays. In certain embodiments, the miR gene product comprises one or more of the miRs described herein.

Microarrays

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

In certain embodiments, the nucleic acid hybridization is performed using a solid phase nucleic acid biochip array, in particular a microarray or in situ hybridization or wherein the nucleic acid amplification method is realtime PCR (RT-PCR) or quantitative realtime PCR (qRT-PCR).

In certain embodiments, the kit comprises a solid-phase nucleic acid biochip array, in particular a microarray, or a set of beads for miRNA determination.

In certain embodiments, the kit comprises a device for performing a nucleic acid detection based on hybridization and optionally amplification such as PCR, RT-PCR or qRT-PCR.

Also described herein are sets of oligo- or polynucleotides for diagnosing cancer comprising the sequences of at least 2, preferably at least 3, 5, 10 or all of the indicated miRNAs, and/or the complement of such sequences.

Methods

Also described herein are methods for the assessment of a clinical condition related to cancer of a patient. In one embodiment, a method for in vitro diagnosis of ovarian cancer, comprises:

a) obtaining a sample from a subject;

b) determining expression levels of one or more miRNAs as ovarian cancer biomarkers and an internal control RNA;

c) computing relative expression levels of the one or more miRNAs as ovarian biomarkers;

d) computing a prediction model by using one or more variables, wherein the variables include relative expression levels of the one or more miRNAs as ovarian biomarkers and, optionally, one or more risk factors of ovarian cancer; and, e) computing a disease risk probability by the prediction model, wherein the subject is diagnosed as ovarian if the disease risk probability is greater than 0.5.

In certain embodiments, in a method for in vitro diagnosis of ovarian cancer, one or more miRNAs as ovarian cancer biomarkers are obtained from a method for selecting a miRNA for use as a disease diagnostic biomarker, which comprising:

a) obtaining samples from subjects, wherein the subjects are composed of people suffering from the disease and people not suffering from the disease;

b) determining expression levels of candidate miRNAs and an internal control RNA in the samples;

c) computing relative expression levels of the candidate miRNAs;

d) computing a prediction model with one or more variables, wherein the variables include relative expression levels of one or more candidate miRNAs and, optionally one or more risk factors of the disease; and e) computing a disease risk probability, sensitivity and specificity by the prediction model, wherein the one or more candidate miRNAs with the highest sensitivity and the highest specificity are selected to be the disease diagnosis biomarker. In certain embodiments, the risk factors are risk factors of ovarian cancer. In certain embodiments, the one or more miRNAs are selected from the group consisting of miR-484, miR-642 and miRNA-217.

In certain embodiments, the one or more miRNAs are used as a reference parameter for evaluating effect of an ovarian cancer treatment and screening a drug against ovarian cancer.

In certain embodiments, the miR-484 has a significantly different expression level between an ovarian cancer patient and normal healthy subjects.

In certain embodiments, the expression levels of one or more miRNAs and internal control RNA are determined by quantitative real-time RT-PCR and expressed as a cycle threshold (Ct).

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

Citation of any documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method of diagnosing an ovarian cancer that is resistant to chemotherapeutic intervention in a subject, comprising:
 a) measuring, by microarray assay, miR-484, miR-642 and miR-217 expression levels in a sample of ovarian tissue from the subject, as compared to control expression levels, and
 b) detecting and quantifying the microarray assay of step a) to determine the levels of miR-484, miR-642 and miR-217 signature, and
 c) determining chemoresistant ovarian cancer in the subject if the subject has decreased miR-484, miR-642 and miR-217 expression levels compared to the control expression levels,
 wherein the chemoresistant ovarian cancer is resistant to therapeutic intervention from a chemotherapeutic agent selected from one or more of: a platinum-based drug, carboplatin, cisplatin, a taxane, paclitaxel, docetaxel, gemcitabine, doxorubicin, etoposide, vinorelbine, xabepilone, an epithelone drug, bevacizumab, and/or phenoxodiol, wherein step (a) comprises:
  1) reverse transcribing miR-484, miR-642 and miR-217 RNA from the sample to provide a set of target oligodeoxynucleotides;
  2) hybridizing the target oligodeoxynucleotides to a microarray comprising miR-484, miR-642 and miR-217 miRNA-specific probe oligonucleotides to provide a hybridization profile for the test sample; and
  3) comparing the profile of step (2) to control.

2. A method of claim 1, wherein step a) further includes identifying expression levels of: miR-592, miR-302d, miR-491, miR-483-5p, miR-653, miR-181a, miR-671-3p, miR-19a and/or miR-744, as compared to control expression levels.

3. A method of claim 1, wherein step a) further includes identifying expression levels of: miR-296-5p and/or miR-518e, as compared to control expression levels.

4. A method of claim 1, wherein step 3) comprises comparing the sample hybridization profile to a hybridization profile generated from a control sample.

5. A method of claim 1, wherein step 3) comprises comparing the sample hybridization profile to a database, statistics, or a table of miR levels associated with non-cancerous samples.

6. The method of claim 1, wherein the ovarian cancer is serous epithelial ovarian carcinoma.

7. A method of determining whether a human subject has a poor survival prognosis for an ovarian cancer, comprising:
 a) measuring, by microarray assay, the expression levels of a miR-484 gene product signature in a sample of ovarian tissue from the human subject, the miR gene product signature consisting of miR gene products: miR-484, mir-642 and miR-217; and
 b) detecting and quantifying the microarray assay of step a) to determine the levels of miR-484, miR-642 and miR-217 signature, and
 c) determining the poor survival prognosis of the human subject when a decrease in the expression levels of the miR gene products in the sample, relative to corresponding expression levels of miR gene products in a control sample of cancer-free ovarian tissue, is indicative of the human subject having a poor survival prognosis for ovarian cancer, wherein step (a), comprises:
  1) reverse transcribing miR-484, miR-642 and miR-217 RNA from the sample to provide a set of target oligodeoxynucleotides;
  2) hybridizing the target oligodeoxynucleotides to a microarray comprising miR-484, miR-642 and miR-217 miRNA-specific probe oligonucleotides to provide a hybridization profile for the test sample; and
  3) comparing the profile of step (2) to control.

8. The method of claim 7, wherein the step (b) of determining the survival prognosis of the subject distinguishes serous ovarian cancer from other ovarian cancers.

9. The method of claim 7, wherein the step (b) of determining the survival prognosis of the subject predicts response to chemotherapeutic intervention from a chemotherapeutic agent selected from one or more of: a platinum-based drug, carboplatin, cisplatin, a taxane, paclitaxel, docetaxel, gemcitabine, doxorubicin, etoposide, vinorelbine, xabepilone, an epithelone drug, bevacizumab (Avastin®) and/or phenoxodiol.

* * * * *

SEQUENCE LISTING

```
<160> NUMBER OF SEQ ID NOS: 15

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctctagacc caggccatgc tcacgtccgg agtaacacta c                          41
```

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctctagaga aatacatttt attatcgctg taccattctg ggg                        43

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctagagtgc cggaagctgc gaaggtg                                          27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctagacagg gttgggggtc acagttc                                          27

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacaatgaca cctccccgag cctctgcagg ggcctctctc ggcagccaca                 50

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctcggggag gtgtcattgt gacaccacag ccagctcaca gtgcggccag                 50

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtgggggaa caaagaggta aaaaacagcc aagc                                  34

<210> SEQ ID NO 8

```
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcttggctgt tttttacctc tttgttcccc cact                               34

<210> SEQ ID NO 9
<211> LENGTH: 21
<212> TYPE: RNA
<213> ORGANISM: Homo sapiens

<400> SEQUENCE: 9 agggccccc cucaauccug u                                              21

<210> SEQ ID NO 10
<211> LENGTH: 21
<212> TYPE: RNA
<213> ORGANISM: Homo sapiens

<400> SEQUENCE: 10
cugcgaguga gggggggccu u                                             21

<210> SEQ ID NO 11
<211> LENGTH: 22
<212> TYPE: RNA
<213> ORGANISM: Homo sapiens

<400> SEQUENCE: 11
ucaggcucag uccccucccg au                                            22

<210> SEQ ID NO 12
<211> LENGTH: 27
<212> TYPE: RNA
<213> ORGANISM: Homo sapiens

<400> SEQUENCE: 12 ccagugggg aacaaagagg agccugg                                        27

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agugggggaa caaagaggta aaaaa                                         25

<210> SEQ ID NO 14
<211> LENGTH: 23
<212> TYPE: RNA
<213> ORGANISM: Homo sapiens

<400> SEQUENCE: 14
cuuuggagag uacuggagcc ugc                                           23

<210> SEQ ID NO 15
```

```
<211> LENGTH: 23
<212> TYPE: RNA
<213> ORGANISM: Homo sapiens

<400> SEQUENCE: 15
cuuuggagag uacugcaaau gca                                          23
```